United States Patent
Kadow et al.

(10) Patent No.: US 10,106,504 B2
(45) Date of Patent: Oct. 23, 2018

(54) PYRIDIN-3-YL ACETIC ACID DERIVATIVES AS INHIBITORS OF HUMAN IMMUNODEFICIENCY VIRUS REPLICATION

(71) Applicant: ViiV Healthcare UK (No. 5) Limited, Brentford, Middlesex (GB)

(72) Inventors: John F. Kadow, Wallingford, CT (US); B. Narasimhulu Naidu, Wallingford, CT (US); Yong Tu, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/749,133

(22) PCT Filed: Aug. 18, 2016

(86) PCT No.: PCT/IB2016/054944
§ 371 (c)(1),
(2) Date: Jan. 31, 2018

(87) PCT Pub. No.: WO2017/029631
PCT Pub. Date: Feb. 23, 2017

(65) Prior Publication Data
US 2018/0222864 A1    Aug. 9, 2018

Related U.S. Application Data

(60) Provisional application No. 62/207,560, filed on Aug. 20, 2015.

(51) Int. Cl.
| | | |
|---|---|---|
| C07D 213/55 | (2006.01) |
| C07D 405/14 | (2006.01) |
| C07D 405/04 | (2006.01) |
| C07D 487/04 | (2006.01) |
| C07D 491/052 | (2006.01) |
| A61K 31/5365 | (2006.01) |
| A61K 31/4433 | (2006.01) |
| A61K 31/4418 | (2006.01) |
| A61P 31/18 | (2006.01) |
| A61K 31/519 | (2006.01) |
| A61K 31/506 | (2006.01) |
| C07D 401/04 | (2006.01) |
| C07D 491/06 | (2006.01) |
| A61K 31/4741 | (2006.01) |
| A61K 31/4725 | (2006.01) |

(52) U.S. Cl.
CPC ........ *C07D 213/55* (2013.01); *A61K 31/4418* (2013.01); *A61K 31/4433* (2013.01); *A61K 31/4725* (2013.01); *A61K 31/4741* (2013.01); *A61K 31/506* (2013.01); *A61K 31/519* (2013.01); *A61K 31/5365* (2013.01); *A61P 31/18* (2018.01); *C07D 401/04* (2013.01); *C07D 405/04* (2013.01); *C07D 405/14* (2013.01); *C07D 487/04* (2013.01); *C07D 491/06* (2013.01)

(58) Field of Classification Search
CPC .. C07D 213/55; C07D 405/14; C07D 405/04; C07D 487/04; C07D 491/052
See application file for complete search history.

(56) References Cited

FOREIGN PATENT DOCUMENTS

| WO | WO 2010/130034 A1 | 11/2010 |
| WO | WO 2013/157622 A1 | 10/2013 |
| WO | WO 2015/126726 A1 | 8/2015 |

*Primary Examiner* — Bruck Kifle
(74) *Attorney, Agent, or Firm* — Robert H. Brink; Edward R. Gimmi; William R. Majarian

(57) ABSTRACT

Disclosed are compounds of Formula I, including pharmaceutically acceptable salts, pharmaceutical compositions comprising the compounds, methods for making the compounds and their use in inhibiting HIV integrase and treating those infected with HIV or AIDS.

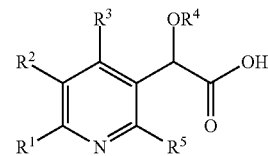

21 Claims, No Drawings

PYRIDIN-3-YL ACETIC ACID DERIVATIVES AS INHIBITORS OF HUMAN IMMUNODEFICIENCY VIRUS REPLICATION

CROSS REFERENCE TO RELATED INVENTION

This application is a § 371 of International Application No. PCT/IB2016/054944, filed 18 Aug. 2016, which claims the benefit of U.S. Provisional Application No. 62/207,560, filed 20 Aug. 2015.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2013 point to close to 3.4 million new infections in that year alone. In the same year there were approximately 1.6 million deaths associated with HIV and AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity, i.e., cobicistat, available from Gilead Sciences, Inc. under the tradename TYBOST™ (cobicistat) tablets, has recently been approved for use in combinations with certain antiretroviral agents (ARVs) that may benefit from boosting.

In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See, for example, the following patent applications: WO2007131350, WO2009062285, WO2009062288, WO2009062289, WO2009062308, WO2010130034, WO2010130842, WO2011015641, WO2011076765, WO2012033735, WO2013123148, WO2013134113, WO2014164467, WO2014159959, and WO2015126726.

What is now needed in the art are additional compounds which are novel and useful in the treatment of HIV. Additionally, these compounds may desireably provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

By virtue of the present invention, it is now possible to provide compounds that are novel and are useful in the treatment of HIV. Additionally, the compounds may provide advantages for pharmaceutical uses, for example, with regard to one or more of their mechanism of action, binding, inhibition efficacy, target selectivity, solubility, safety profiles, or bioavailability.

The invention also provides pharmaceutical compositions comprising the compounds of the invention, including pharmaceutically acceptable salts thereof, and a pharmaceutically acceptable carrier, excipient, and/or diluent.

In addition, the invention provides methods of treating HIV infection comprising administering a therapeutically effective amount of the compounds of the invention to a patient.

In addition, the invention provides methods for inhibiting HIV integrase.

Also provided in accordance with the invention are methods for making the compounds of the invention.

The present invention is directed to these, as well as other important ends, hereinafter described.

DESCRIPTION OF THE INVENTION

Unless specified otherwise, these terms have the following meanings.

"Alkyl" means a straight or branched saturated hydrocarbon comprised of 1 to 10 carbons, and preferably 1 to 6 carbons.

"Alkenyl" means a straight or branched alkyl group comprised of 2 to 10 carbons with at least one double bond and optionally substituted with 0-3 halo or alkoxy group.

"Alkynyl" means a straight or branched alkyl group comprised of 2 to 10 carbons, preferably 2 to 6 carbons, containing at least one triple bond and optionally substituted with 0-3 halo or alkoxy group.

"Aryl" mean a carbocyclic group comprised of 1-3 rings that are fused and/or bonded and at least one or a combination of which is aromatic. The non-aromatic carbocyclic portion, where present, will be comprised of $C_3$ to $C_7$ alkyl group. Examples of aromatic groups include, but are not limited to, indanyl, indenyl, naphthyl, phenyl, tetrahydronaphthyl and cyclopropylphenyl. The aryl group can be attached to the parent structure through any substitutable carbon atom in the group.

"Arylalkyl" is a $C_1$-$C_5$ alkyl group attached to 1 to 2 aryl groups and linked to the parent structure through the alkyl moiety. Examples include, but are not limited to, —($CH_2$)-Ph with n=1-5, —CH($CH_3$)Ph, —CH(Ph)$_2$.

"Aryloxy" is an aryl group attached to the parent structure by oxygen.

"Cycloalkyl" means a monocyclic ring system composed of 3 to 7 carbons.

"Halo" includes fluoro, chloro, bromo, and iodo.

"Haloalkyl" and "haloalkoxy" include all halogenated isomers from monohalo to perhalo.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heterocyclyl or heterocyclic" means a cyclic group of 1-3 rings comprised of carbon and at least one other atom selected independently from oxygen, nitrogen and sulfur. The rings could be bridged, fused and/or bonded, through a direct or spiro attachment, with the option to have one or a combination thereof be aromatic. Examples include, but are not limited to, azaindole, azaindoline, azetidine, benzimidazole, bezodioxolyl, benzoisothiazole, benzothiazole, benzothiadiazole, benzothiophene, benzoxazole, carbazole, chroman, dihalobezodioxolyl, dihydrobenzofuran, dihydrobenzo[1,4]oxazine, 1,3-dihydrobenzo[c]thiophene 2,2-dioxide, 2,3-dihydrobenzo[d]isothiazole 1,1-dioxide, 3,4-dihydro-2H-pyrido[3,2-b][1,4]oxazine, 2,3-dihydro-1H-pyrrolo[3,4-c]pyridine and its regioisomeric variants, 6,7-dihydro-5H-pyrrolo[2,3-b]pyrazine and its regioisomeric variants, furanylphenyl, imidazole, imidazo[1,2-a]pyridine, indazole, indole, indoline, isoquinoline, isoquinolinone, isothiazolidine 1,1-dioxide, morpholine, 2-oxa-5-azabicyclo[2.2.1]heptane, oxadiazole-phenyl, oxazole, phenylaztidine, phenylindazole, phenylpiperidine, phenylpiperizine, phenyloxazole, phenylpyrrolidine, piperidine, pyridine, pyridinylphenyl, pyridinylpyrrolidine, pyrimidine, pyrimidinylphenyl, pyrrazole-phenyl, pyrrolidine, pyrrolidin-2-one, 1H-pyrazolo[4,3-c]pyridine and its regioisomeric variants, pyrrole, 5H-pyrrolo[2,3-b]pyrazine, 7H-pyrrolo[2,3-d]pyrimidine and its regioisomeric variants, quinazoline, quinoline, quinoxaline, tetrahydroisoquinoline, 1,2,3,4-tetrahydro-1,8-naphthyridine, tetrahydroquinoline, 4,5,6,7-tetrahydrothieno[3,2-c]pyridine, 1,2,5-thiadiazolidine 1,1-dioxide, thiophene, thiophenylphenyl, triazole, or triazolone. Unless otherwise specifically set forth, the heterocyclic group can be attached to the parent structure through any suitable atom in the group that results in a stable compound.

It is understood that a subset of the noted heterocyclic examples encompass regioisomers. For instance, "azaindole" refers to any of the following regioisomers: 1H-pyrrolo[2,3-b]pyridine, 1H-pyrrolo[2,3-c]pyridine, 1H-pyrrolo[3,2-c]pyridine, and 1H-pyrrolo[3,2-b]pyridine. In addition the "regioisomer variants" notation as in, for example, "5H-pyrrolo[2,3-b]pyrazine and its regioisomeric variants" would also encompass 7H-pyrrolo[2,3-d]pyrimidine, 7H-pyrrolo[2,3-c]pyridazine, 1H-pyrrolo[2,3-d]pyridazine, 5H-pyrrolo[3,2-c]pyridazine, and 5H-pyrrolo[3,2-d]pyrimidine. Similarly, 6,7-dihydro-5H-pyrrolo[2,3-b]pyrazine and its regioisomeric variants would encompass 6,7-dihydro-5H-pyrrolo[2,3-d]pyrimidine and 6,7-dihydro-5H-pyrrolo[2,3-c]pyridazine. It is also understood that the lack of "regioisomeric variants" notation does not in any way restrict the claim scope to the noted example only.

"Heterocyclylalkyl" is a heterocyclyl moiety attached to the parent structure through $C_1$-$C_5$ alkyl group. Examples include, but are not limited to, —($CH_2$)$_n$—$R^Z$ or —CH($CH_3$)—($R^Z$) where n=1-5 and that $R^Z$ is chosen from benzimidazole, imidazole, indazole, isooxazole, phenylpyrazole, pyridine, quinoline, thiazole, triazole, triazolone, oxadiazole.

Terms with a hydrocarbon moiety (e.g. alkoxy) include straight and branched isomers for the hydrocarbon portion with the indicated number of carbon atoms.

Bonding and positional bonding relationships are those that are stable as understood by practitioners of organic chemistry.

Parenthetic and multiparenthetic terms are intended to clarify bonding relationships to those skilled in the art. For example, a term such as ((R)alkyl) means an alkyl substituent further substituted with the substituent R.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

"Combination," "coadministration," "concurrent" and similar terms referring to the administration of a compound of Formula I with at least one anti-HIV agent mean that the components are part of a combination antiretroviral therapy or highly active antiretroviral therapy ("HAART") as understood by practitioners in the field of AIDS and HIV infection.

"Therapeutically effective" means the amount of agent required to provide a benefit to a patient as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus.

"Treatment," "therapy," "regimen," "HIV infection," "ARC," "AIDS" and related terms are used as understood by practitioners in the field of AIDS and HIV infection.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

In an aspect of the invention, there is provided a compound of Formula I:

wherein:
$R^1$ is selected from hydrogen, alkyl, hydroxyalkyl, alkoxyalkyl, (alkoxy)alkoxyalkyl, ((alkoxy)alkoxy)alkoxyalkyl, (oxetanyl)alkyl, (tetrahydropyranyl)alkyl, ((oxetanyl)oxy)alkyl, ((tetrahydropyranyl)oxy)alkyl, ((oxetanyl)alkoxy)alkyl, ((tetrahydropyranyl)alkoxy)alkyl, (($R^7$)($R^8$)N)alkyl, or ($R^7$)($R^8$)N;
$R^2$ is phenyl substituted with 0-1 ($Ar^1$)alkoxy substituents and also substituted with 0-3 substituents selected from halo, alkyl, haloalkyl, alkoxy, and haloalkoxy;
or $R^2$ is tetrahydroisoquinolinyl substituted with 1 $R^6$ substituent and also with 0-3 substituents selected from halo, alkyl, haloalkyl, alkoxy, and haloalkoxy;
or $R^2$ is chromanyl substituted with 0-3 substituents selected from halo, alkyl, haloalkyl, alkoxy, and haloalkoxy;
$R^3$ is selected from cycloalkyl, cycloalkenyl, phenyl, chromanyl, chromenyl, oxazinyl, or dihydropyranoquinolinyl, and is substituted with 0-3 substituents selected from halo, alkyl, haloalkyl, alkoxy, haloalkoxy, and ($Ar^1$)alkoxy;
$R^4$ is selected from alkyl or haloalkyl;
$R^5$ is alkyl;
$R^6$ is selected from hydrogen, alkyl, ($Ar^1$)alkyl, benzyloxycarbonyl, or $Ar^2$;
$R^7$ is selected from hydrogen, alkyl, alkoxyalkyl, or (tetrahydropyranyl)alkyl;
$R^8$ is selected from hydrogen, alkyl, or alkoxyalkyl;
$Ar^1$ is phenyl substituted with 0-3 substituents selected from halo, alkyl, haloalkyl, alkoxy, and haloalkoxy; and
$Ar^2$ is selected from pyridinyl, pyridazinyl, pyrimidinyl, pyridazinyl, or pyrazolopyrimidinyl, and is substituted with 0-3 substituents selected from halo, alkyl, haloalkyl, alkoxy, and haloalkoxy;
or a pharmaceutically acceptable salt thereof.

In an aspect of the invention, $R^1$ is alkyl.

In an aspect of the invention, $R^1$ is selected from hydroxyalkyl, alkoxyalkyl, (alkoxy)alkoxyalkyl, ((alkoxy)alkoxy)alkoxyalkyl, (oxetanyl)alkyl, (tetrahydropyranyl)alkyl, ((oxetanyl)oxy)alkyl, ((tetrahydropyranyl)oxy)alkyl, ((oxetanyl)alkoxy)alkyl, ((tetrahydropyranyl)alkoxy)alkyl, (($R^7$)($R^8$)N)alkyl, or ($R^7$)($R^8$)N.

In an aspect of the invention, $R^2$ is phenyl substituted with 0-1 ($Ar^1$)alkoxy substituents.

In an aspect of the invention, $R^2$ is tetrahydroisoquinolinyl substituted with 1 $R^6$ substituent and also with 0-3 substituents selected from halo, alkyl, haloalkyl, alkoxy, and haloalkoxy.

In an aspect of the invention, $R^2$ is tetrahydroisoquinolinyl substituted with 1 $R^6$ substituent.

In an aspect of the invention, $R^2$ is chromanyl substituted with 0-3 substituents selected from halo, alkyl, haloalkyl, alkoxy, and haloalkoxy.

In an aspect of the invention, $R^6$ is ($Ar^1$)alkyl or $Ar^2$.

In an aspect of the invention, there is provided a compound of Formula I:

wherein:
$R^1$ is selected from hydrogen, alkyl, hydroxyalkyl, alkoxyalkyl, (alkoxy)alkoxyalkyl, ((alkoxy)alkoxy)alkoxyalkyl, (oxetanyl)alkyl, (tetrahydropyranyl)alkyl, ((oxetanyl)oxy)alkyl, ((tetrahydropyranyl)oxy)alkyl, ((oxetanyl)alkoxy)alkyl, ((tetrahydropyranyl)alkoxy)alkyl, (($R^7$)($R^8$)N)alkyl, or ($R^7$)($R^8$)N;
$R^2$ is phenyl substituted with 0-1 ($Ar^1$)alkoxy substituents and also substituted with 0-3 substituents selected from halo, alkyl, haloalkyl, alkoxy, and haloalkoxy; $R^3$ is selected from cycloalkyl, cycloalkenyl, phenyl, chromanyl, chromenyl, oxazinyl, or dihydropyranoquinolinyl, and is substituted with 0-3 substituents selected from halo, alkyl, haloalkyl, alkoxy, haloalkoxy, and ($Ar^1$)alkoxy;
$R^4$ is selected from alkyl or haloalkyl;
$R^5$ is alkyl;
$R^6$ is selected from hydrogen, alkyl, ($Ar^1$)alkyl, benzyloxycarbonyl, or $Ar^2$;
$R^7$ is selected from hydrogen, alkyl, alkoxyalkyl, or (tetrahydropyranyl)alkyl;
$R^8$ is selected from hydrogen, alkyl, or alkoxyalkyl;
$Ar^1$ is phenyl substituted with 0-3 substituents selected from halo, alkyl, haloalkyl, alkoxy, and haloalkoxy; and
$Ar^2$ is selected from pyridinyl, pyridazinyl, pyrimidinyl, pyridazinyl, or pyrazolopyrimidinyl, and is substituted with 0-3 substituents selected from halo, alkyl, haloalkyl, alkoxy, and haloalkoxy;
or a pharmaceutically acceptable salt thereof.

In an aspect of the invention, there is provided a compound of Formula I:

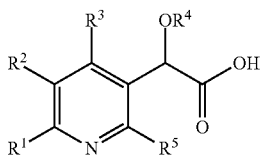

wherein:
$R^1$ is selected from hydrogen, alkyl, hydroxyalkyl, alkoxyalkyl, (alkoxy)alkoxyalkyl, ((alkoxy)alkoxy)alkoxyalkyl, (oxetanyl)alkyl, (tetrahydropyranyl)alkyl, ((oxetanyl)oxy)alkyl, ((tetrahydropyranyl)oxy)alkyl, ((oxetanyl)alkoxy)alkyl, ((tetrahydropyranyl)alkoxy)alkyl, $((R^7)(R^8)N)$alkyl, or $(R^7)(R^8)N$;
$R^2$ is tetrahydroisoquinolinyl substituted with 1 $R^6$ substituent and also with 0-3 substituents selected from halo, alkyl, haloalkyl, alkoxy, and haloalkoxy;
$R^3$ is selected from cycloalkyl, cycloalkenyl, phenyl, chromanyl, chromenyl, oxazinyl, or dihydropyranoquinolinyl, and is substituted with 0-3 substituents selected from halo, alkyl, haloalkyl, alkoxy, haloalkoxy, and $(Ar^1)$alkoxy;
$R^4$ is selected from alkyl or haloalkyl;
$R^5$ is alkyl;
$R^6$ is selected from hydrogen, alkyl, $(Ar^1)$alkyl, benzyloxycarbonyl, or $Ar^2$;
$R^7$ is selected from hydrogen, alkyl, alkoxyalkyl, or (tetrahydropyranyl)alkyl;
$R^8$ is selected from hydrogen, alkyl, or alkoxyalkyl;
$Ar^1$ is phenyl substituted with 0-3 substituents selected from halo, alkyl, haloalkyl, alkoxy, and haloalkoxy; and
$Ar^2$ is selected from pyridinyl, pyridazinyl, pyrimidinyl, pyridazinyl, or pyrazolopyrimidinyl, and is substituted with 0-3 substituents selected from halo, alkyl, haloalkyl, alkoxy, and haloalkoxy;
or a pharmaceutically acceptable salt thereof.

In an aspect of the invention, there is provided a compound of Formula I:

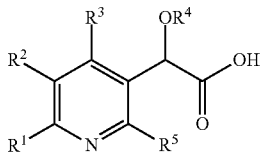

wherein:
$R^1$ is selected from hydrogen, alkyl, hydroxyalkyl, alkoxyalkyl, (alkoxy)alkoxyalkyl, ((alkoxy)alkoxy)alkoxyalkyl, (oxetanyl)alkyl, (tetrahydropyranyl)alkyl, ((oxetanyl)oxy)alkyl, ((tetrahydropyranyl)oxy)alkyl, ((oxetanyl)alkoxy)alkyl, ((tetrahydropyranyl)alkoxy)alkyl, $((R^7)(R^8)N)$alkyl, or $(R^7)(R^8)N$;
$R^2$ is chromanyl substituted with 0-3 substituents selected from halo, alkyl, haloalkyl, alkoxy, and haloalkoxy;
$R^3$ is selected from cycloalkyl, cycloalkenyl, phenyl, chromanyl, chromenyl, oxazinyl, or dihydropyranoquinolinyl, and is substituted with 0-3 substituents selected from halo, alkyl, haloalkyl, alkoxy, haloalkoxy, and $(Ar^1)$alkoxy;
$R^4$ is selected from alkyl or haloalkyl;
$R^5$ is alkyl;
$R^6$ is selected from hydrogen, alkyl, $(Ar^1)$alkyl, benzyloxycarbonyl, or $Ar^2$;
$R^7$ is selected from hydrogen, alkyl, alkoxyalkyl, or (tetrahydropyranyl)alkyl;
$R^8$ is selected from hydrogen, alkyl, or alkoxyalkyl;
$Ar^1$ is phenyl substituted with 0-3 substituents selected from halo, alkyl, haloalkyl, alkoxy, and haloalkoxy; and
$Ar^2$ is selected from pyridinyl, pyridazinyl, pyrimidinyl, pyridazinyl, or pyrazolopyrimidinyl, and is substituted with 0-3 substituents selected from halo, alkyl, haloalkyl, alkoxy, and haloalkoxy;
or a pharmaceutically acceptable salt thereof.

For a particular compound of Formula I, the scope of any instance of a variable substituent, including $R^1$, $R^2$, $R^3$, $R^4$, $R^5$, $R^6$, $R^7$, $R^8$, $Ar^1$ and $Ar^2$ can be used independently with the scope of any other instance of a variable substituent. As such, the invention includes combinations of the different aspects.

In an aspect of the invention, there is provided a composition useful for treating HIV infection comprising a therapeutic amount of a compound of Formula I and a pharmaceutically acceptable carrier. In an aspect of the invention, the composition further comprises a therapeutically effective amount at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier. In an aspect of the invention, the other agent is dolutegravir.

In an aspect of the invention, there is provided a method for treating HIV infection comprising administering a therapeutically effective amount of a compound of Formula I, or a pharmaceutically acceptable salt thereof, to a patient in need thereof. In an aspect of the invention, the method further comprises administering a therapeutically effective amount of at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. In an aspect of the invention, the other agent is dolutegravir. In an aspect of the invention, the other agent is administered to the patient prior to, simultaneously with, or subsequently to the compound of Formula I.

Preferred compounds in accordance with the present invention include the following:
(2S)-2-(4,5-Bis(8-fluoro-5-methylchroman-6-yl)-2,6-dimethylpyridin-3-yl)-2-(tert-butoxy)acetic acid;
(S)-2-(tert-Butoxy)-2-(4-(4-chlorophenyl)-5-(4-((4-methoxybenzyl)oxy)phenyl)-2,6-dimethylpyridin-3-yl) acetic acid;
(S)-2-(tert-Butoxy)-2-(5-(4-((4-methoxybenzyl)oxy)phenyl)-2,6-dimethyl-4-(p-tolyl)pyridin-3-yl)acetic acid;
(S)-2-(4,5-Bis(4-((4-methoxybenzyl)oxy)phenyl)-2,6-dimethylpyridin-3-yl)-2-(tert-butoxy)acetic acid;
(S)-2-(tert-Butoxy)-2-(5-(4-((4-fluorobenzyl)oxy)phenyl)-2,6-dimethyl-4-(p-tolyl)pyridin-3-yl)acetic acid;
(2S)-2-(tert-Butoxy)-2-(4-(8-fluoro-5-methylchroman-6-yl)-5-(4-(4-fluorophenethoxy)phenyl)-2,6-dimethylpyridin-3-yl)acetic acid;
(2S)-2-(tert-Butoxy)-2-(5-(4-ethoxyphenyl)-4-(8-fluoro-5-methylchroman-6-yl)-2,6-dimethylpyridin-3-yl)acetic acid;

(S)-2-(4,5-Bis(4-(4-fluorophenethoxy)phenyl)-2,6-dimethylpyridin-3-yl)-2-(tert-butoxy)acetic acid;

(S)-2-(tert-Butoxy)-2-(4-(chroman-6-yl)-5-(4-(4-fluorophenethoxy)phenyl)-2,6-dimethylpyridin-3-yl)acetic acid;

(S)-2-(tert-Butoxy)-2-(4-(chroman-6-yl)-6-((dimethylamino)methyl)-5-(4-(4-fluorophenethoxy)phenyl)-2-methylpyridin-3-yl)acetic acid;

(S)-2-(tert-Butoxy)-2-(4-(chroman-6-yl)-5-(4-(4-fluorophenethoxy)phenyl)-2-methyl-6-((((tetrahydro-2H-pyran-4-yl)methyl)amino)methyl)pyridin-3-yl)acetic acid;

(S)-2-(tert-Butoxy)-2-(4-(chroman-6-yl)-5-(4-(4-fluorophenethoxy)phenyl)-6-(((2-methoxyethyl)amino)methyl)-2-methylpyridin-3-yl)acetic acid;

(S)-2-(tert-Butoxy)-2-(4-(chroman-6-yl)-5-(4-(4-fluorophenethoxy)phenyl)-2-methyl-6-((methyl((tetrahydro-2H-pyran-4-yl)methyl)amino)methyl)pyridin-3-yl)acetic acid;

(S)-2-(tert-Butoxy)-2-(4-(chroman-6-yl)-5-(4-(4-fluorophenethoxy)phenyl)-6-(hydroxymethyl)-2-methylpyridin-3-yl)acetic acid;

(S)-2-(tert-Butoxy)-2-(4-(chroman-6-yl)-5-(4-(4-fluorophenethoxy)phenyl)-2-methyl-6-(((tetrahydro-2H-pyran-4-yl)oxy)methyl)pyridin-3-yl)acetic acid;

(S)-2-(tert-Butoxy)-2-(4-(chroman-6-yl)-5-(4-(4-fluorophenethoxy)phenyl)-2-methyl-6-((oxetan-3-ylmethoxy)methyl)pyridin-3-yl)acetic acid;

(S)-2-(tert-Butoxy)-2-(4-(chroman-6-yl)-6-(((2-ethoxyethoxy)methyl)-5-(4-(4-fluorophenethoxy)phenyl)-2-methylpyridin-3-yl)acetic acid;

(S)-2-(tert-Butoxy)-2-(4-(chroman-6-yl)-6-((2-(2-ethoxyethoxy)ethoxy)methyl)-5-(4-(4-fluorophenethoxy)phenyl)-2-methylpyridin-3-yl)acetic acid;

(S)-2-(5-(2-(((Benzyloxy)carbonyl)-1,2,3,4-tetrahydroisoquinolin-6-yl)-4-(chroman-6-yl)-2,6-dimethylpyridin-3-yl)-2-(tert-butoxy)acetic acid;

(S)-2-(tert-Butoxy)-2-(4-(chroman-6-yl)-5-(2-(4-fluorobenzyl)-1,2,3,4-tetrahydroisoquinolin-6-yl)-2,6-dimethylpyridin-3-yl)acetic acid;

(S)-2-(tert-Butoxy)-2-(4-(chroman-6-yl)-2,6-dimethyl-5-(1,2,3,4-tetrahydroisoquinolin-6-yl)pyridin-3-yl)acetic acid;

(S)-2-(tert-Butoxy)-2-(4-(chroman-6-yl)-2,6-dimethyl-5-(2-methyl-1,2,3,4-tetrahydroisoquinolin-6-yl)pyridin-3-yl)acetic acid;

(S)-2-(tert-Butoxy)-2-(4-(chroman-6-yl)-5-(2-(2-fluorobenzyl)-1,2,3,4-tetrahydroisoquinolin-6-yl)-2,6-dimethylpyridin-3-yl)acetic acid;

(S)-2-(tert-Butoxy)-2-(4-(chroman-6-yl)-5-(2-(3-fluorobenzyl)-1,2,3,4-tetrahydroisoquinolin-6-yl)-2,6-dimethylpyridin-3-yl)acetic acid;

(S)-2-(tert-Butoxy)-2-(4-(chroman-6-yl)-5-(2-(2-fluoro-6-methylbenzyl)-1,2,3,4-tetrahydroisoquinolin-6-yl)-2,6-dimethylpyridin-3-yl)acetic acid;

(S)-2-(tert-Butoxy)-2-(4-(chroman-6-yl)-5-(2-(2-fluoro-3-methylbenzyl)-1,2,3,4-tetrahydroisoquinolin-6-yl)-2,6-dimethylpyridin-3-yl)acetic acid;

(S)-2-(tert-Butoxy)-2-(5-(2-(2-chlorobenzyl)-1,2,3,4-tetrahydroisoquinolin-6-yl)-4-(chroman-6-yl)-2,6-dimethylpyridin-3-yl)acetic acid;

(S)-2-(tert-Butoxy)-2-(4-(chroman-6-yl)-5-(2-(2,4-dimethylbenzyl)-1,2,3,4-tetrahydroisoquinolin-6-yl)-2,6-dimethylpyridin-3-yl)acetic acid;

(S)-2-(tert-Butoxy)-2-(5-(2-(2-chloro-6-methylbenzyl)-1,2,3,4-tetrahydroisoquinolin-6-yl)-4-(chroman-6-yl)-2,6-dimethylpyridin-3-yl)acetic acid;

(S)-2-(tert-Butoxy)-2-(4-(chroman-6-yl)-5-(2-(2-fluorophenethyl)-1,2,3,4-tetrahydroisoquinolin-6-yl)-2,6-dimethylpyridin-3-yl)acetic acid;

(S)-2-(tert-Butoxy)-2-(4-(chroman-6-yl)-5-(2-(3-(4-fluorophenyl)propyl)-1,2,3,4-tetrahydroisoquinolin-6-yl)-2,6-dimethylpyridin-3-yl)acetic acid;

(S)-2-(tert-Butoxy)-2-(4-(chroman-6-yl)-2-methyl-6-((methyl((tetrahydro-2H-pyran-4-yl)methyl)amino)methyl)-5-(2-(1-methyl-1H-pyrazolo[3,4-d]pyrimidin-4-yl)-1,2,3,4-tetrahydroisoquinolin-6-yl)pyridin-3-yl)acetic acid;

(S)-2-(tert-Butoxy)-2-(4-(chroman-6-yl)-2-methyl-6-((methyl((tetrahydro-2H-pyran-4-yl)methyl)amino)methyl)-5-(2-(6-methylpyrimidin-4-yl)-1,2,3,4-tetrahydroisoquinolin-6-yl)pyridin-3-yl)acetic acid;

(S)-2-(tert-Butoxy)-2-(4-(chroman-6-yl)-5-(2-(2-fluoro-6-methylbenzyl)-1,2,3,4-tetrahydroisoquinolin-6-yl)-2-methyl-6-((methyl((tetrahydro-2H-pyran-4-yl)methyl)amino)methyl)pyridin-3-yl)acetic acid;

(S)-2-(tert-Butoxy)-2-(5-(2-(2-chloro-6-methylbenzyl)-1,2,3,4-tetrahydroisoquinolin-6-yl)-4-(chroman-6-yl)-2-methyl-6-((methyl((tetrahydro-2H-pyran-4-yl)methyl)amino)methyl)pyridin-3-yl)acetic acid;

(S)-2-(tert-Butoxy)-2-(4-(4,4-difluorochroman-6-yl)-5-(4-(4-fluorophenethoxy)phenyl)-2,6-dimethylpyridin-3-yl)acetic acid;

(S)-2-(tert-Butoxy)-2-(4-(4,4-difluorochroman-6-yl)-5-(2-(2-fluorobenzyl)-1,2,3,4-tetrahydroisoquinolin-6-yl)-2,6-dimethylpyridin-3-yl)acetic acid;

(2S)-2-(tert-Butoxy)-2-(4-(8-fluoro-5-methylchroman-6-yl)-5-(2-(2-fluorobenzyl)-1,2,3,4-tetrahydroisoquinolin-6-yl)-2,6-dimethylpyridin-3-yl)acetic acid;

(2S)-2-(tert-Butoxy)-2-(4-(8-fluoro-5-methylchroman-6-yl)-5-(2-(2-fluoro-6-methylbenzyl)-1,2,3,4-tetrahydroisoquinolin-6-yl)-2,6-dimethylpyridin-3-yl)acetic acid;

(2S)-2-(tert-Butoxy)-2-(4-(8-fluoro-5-methylchroman-6-yl)-2,6-dimethyl-5-(2-(2-methylbenzyl)-1,2,3,4-tetrahydroisoquinolin-6-yl)pyridin-3-yl)acetic acid;

(S)-2-(tert-Butoxy)-2-(5-(2-(2-fluoro-6-methylbenzyl)-1,2,3,4-tetrahydroisoquinolin-6-yl)-2,6-dimethyl-4-(p-tolyl)pyridin-3-yl)acetic acid;

(S)-2-(tert-Butoxy)-2-(5-(2-(2-fluorobenzyl)-1,2,3,4-tetrahydroisoquinolin-6-yl)-2,6-dimethyl-4-(p-tolyl)pyridin-3-yl)acetic acid;

(2S)-2-(tert-Butoxy)-2-(4-(2,3-dihydropyrano[4,3,2-de]quinolin-7-yl)-5-(4-(4-fluorophenethoxy)phenyl)-2,6-dimethylpyridin-3-yl)acetic acid;

(S)-2-(tert-Butoxy)-2-(4-(chroman-6-yl)-5-(4-(2,4-difluorophenethoxy)phenyl)-2,6-dimethylpyridin-3-yl)acetic acid;

(S)-2-(tert-Butoxy)-2-(4-(chroman-6-yl)-5-(4-(2-fluorophenethoxy)phenyl)-2,6-dimethylpyridin-3-yl)acetic acid;

(S)-2-(tert-Butoxy)-2-(4-(4,4-dimethylcyclohex-1-en-1-yl)-5-(4-(4-fluorophenethoxy)phenyl)-2,6-dimethylpyridin-3-yl)acetic acid;

(S)-2-(tert-Butoxy)-2-(4-(8-fluoro-2H-chromen-6-yl)-5-(4-(4-fluorophenethoxy)phenyl)-2,6-dimethylpyridin-3-yl)acetic acid;

(S)-2-(tert-Butoxy)-2-(4-(8-fluorochroman-6-yl)-5-(4-(4-fluorophenethoxy)phenyl)-2,6-dimethylpyridin-3-yl)acetic acid;

(S)-2-(tert-Butoxy)-2-(5-(2-(2-fluoro-6-methylbenzyl)-1,2,3,4-tetrahydroisoquinolin-6-yl)-4-(8-fluorochroman-6-yl)-2,6-dimethylpyridin-3-yl)acetic acid;

(S)-2-(tert-Butoxy)-2-(5-(2-(4-fluoro-2-methylbenzyl)-1,2,
3,4-tetrahydroisoquinolin-6-yl)-4-(8-fluorochroman-6-
yl)-2,6-dimethylpyridin-3-yl)acetic acid;
(S)-2-(tert-Butoxy)-2-(5-(2-(2-chloro-6-methylbenzyl)-1,2,
3,4-tetrahydroisoquinolin-6-yl)-4-(8-fluorochroman-6-
yl)-2,6-dimethylpyridin-3-yl)acetic acid;
(S)-2-(tert-Butoxy)-2-(4-(8-fluorochroman-6-yl)-2,6-dim-
ethyl-5-(2-(6-methylpyrimidin-4-yl)-1,2,3,4-tetrahy-
droisoquinolin-6-yl)pyridin-3-yl)acetic acid;
(S)-2-(tert-Butoxy)-2-(4-(8-fluorochroman-6-yl)-2,6-dim-
ethyl-5-(2-(1-methyl-1H-pyrazolo[3,4-d]pyrimidin-4-yl)-
1,2,3,4-tetrahydroisoquinolin-6-yl)pyridin-3-yl)acetic
acid;
(S)-2-(tert-Butoxy)-2-(4-(chroman-6-yl)-2,6-dimethyl-5-(2-
(1-methyl-1H-pyrazolo[3,4-d]pyrimidin-4-yl)-1,2,3,4-
tetrahydroisoquinolin-6-yl)pyridin-3-yl)acetic acid;
(S)-2-(tert-Butoxy)-2-(4-(chroman-6-yl)-2,6-dimethyl-5-(2-
(6-methylpyrimidin-4-yl)-1,2,3,4-tetrahydroisoquinolin-
6-yl)pyridin-3-yl)acetic acid;
(S)-2-(tert-Butoxy)-2-(4-(chroman-6-yl)-5-(2-(4-fluoro-2-
methylbenzyl)-1,2,3,4-tetrahydroisoquinolin-6-yl)-2,6-
dimethylpyridin-3-yl)acetic acid;
(S)-2-(tert-Butoxy)-2-(4-(chroman-6-yl)-5-(2-(2-methoxy-
pyrimidin-4-yl)-1,2,3,4-tetrahydroisoquinolin-6-yl)-2,6-
dimethylpyridin-3-yl)acetic acid;
(S)-2-(tert-Butoxy)-2-(4-(chroman-6-yl)-5-(2-(2,6-dimeth-
ylpyrimidin-4-yl)-1,2,3,4-tetrahydroisoquinolin-6-yl)-2,
6-dimethylpyridin-3-yl)acetic acid;
(S)-2-(6-Amino-4-(chroman-6-yl)-5-(4-(4-fluoro-
phenethoxy)phenyl)-2-methylpyridin-3-yl)-2-(tert-bu-
toxy)acetic acid;
(S)-2-(6-Amino-4-(chroman-6-yl)-5-(2-(4-fluoro-2-methyl-
benzyl)-1,2,3,4-tetrahydroisoquinolin-6-yl)-2-methyl-
pyridin-3-yl)-2-(tert-butoxy)acetic acid;
(S)-2-(6-Amino-4-(chroman-6-yl)-5-(2-(3-fluoro-2-methyl-
benzyl)-1,2,3,4-tetrahydroisoquinolin-6-yl)-2-methyl-
pyridin-3-yl)-2-(tert-butoxy)acetic acid;
(S)-2-(6-Amino-4-(chroman-6-yl)-5-(2-(2-fluoro-6-methyl-
benzyl)-1,2,3,4-tetrahydroisoquinolin-6-yl)-2-methyl-
pyridin-3-yl)-2-(tert-butoxy)acetic acid;
(S)-2-(6-Amino-5-(2-(2-chloro-6-methylbenzyl)-1,2,3,4-
tetrahydroisoquinolin-6-yl)-4-(chroman-6-yl)-2-methyl-
pyridin-3-yl)-2-(tert-butoxy)acetic acid;
(S)-2-(6-Amino-4-(chroman-6-yl)-5-(2-(2-methoxypyrimi-
din-4-yl)-1,2,3,4-tetrahydroisoquinolin-6-yl)-2-methyl-
pyridin-3-yl)-2-(tert-butoxy)acetic acid;
(S)-2-(6-Amino-4-(chroman-6-yl)-5-(2-(2,6-dimethylpy-
rimidin-4-yl)-1,2,3,4-tetrahydroisoquinolin-6-yl)-2-
methylpyridin-3-yl)-2-(tert-butoxy)acetic acid;
(S)-2-(tert-Butoxy)-2-(4-(chroman-6-yl)-5-(4-(4-fluoro-
phenethoxy)phenyl)-2-methyl-6-(3-(tetrahydro-2H-
pyran-4-yl)propyl)pyridin-3-yl)acetic acid;
(S)-2-(tert-Butoxy)-2-(4-(chroman-6-yl)-2-methyl-5-(2-(6-
methylpyrimidin-4-yl)-1,2,3,4-tetrahydroisoquinolin-6-
yl)-6-(3-(tetrahydro-2H-pyran-4-yl)propyl)pyridin-3-yl)
acetic acid;
(S)-2-(tert-Butoxy)-2-(4-(chroman-6-yl)-5-(2-(2-fluoro-6-
methylbenzyl)-1,2,3,4-tetrahydroisoquinolin-6-yl)-2-
methyl-6-(3-(tetrahydro-2H-pyran-4-yl)propyl)pyridin-3-
yl)acetic acid; and
pharmaceutically acceptable salts thereof.

The compounds of the invention herein described may typically be administered as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms, including capsules, tablets, lozenges, and powders, as well as liquid suspensions, syrups, elixirs, and solutions. Compositions are made using available formulation techniques, and excipients (such as binding and wetting agents) and vehicles (such as water and alcohols) which are generally used for compositions. See, for example, Remington's Pharmaceutical Sciences, 17th edition, Mack Publishing Company, Easton, Pa. (1985).

Solid compositions which are normally formulated in dosage units and compositions providing from about 1 to 1000 milligram ("mg") of the active ingredient per dose are typical. Some examples of dosages are 1 mg, 10 mg, 100 mg, 250 mg, 500 mg, and 1000 mg. Generally, other antiretroviral agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 milligram per milliliter ("mg/mL"). Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other antiretroviral agents used clinically. Typically, the daily dose will be about 1-100 milligram per kilogram ("mg/kg") body weight daily. Generally, more compound is required orally and less parenterally. The specific dosing regimen, however, will be determined by a physician using sound medical judgment.

The compounds of this invention desireably have activity against HIV. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, HIV capsid inhibitors, anti-infectives, and immunomodulators, such as, for example, PD-1 inhibitors, PD-L1 inhinitors, antibodies, and the like. In these combination methods, the compound of Formula I will generally be given in a daily dose of about 1-100 mg/kg body weight daily in conjunction with other agents. The other agents generally will be given in the amounts used therapeutically. The specific dosing regimen, however, will be determined by a physician using sound medical judgment.

Examples of nucleoside HIV reverse transcriptase inhibitors include abacavir, didanosine, emtricitabine, lamivudine, stavudine, tenofovir, zalcitabine, and zidovudine.

Examples of non-nucleoside HIV reverse transcriptase inhibitors include delavirdine, efavirenz, etrivirine, nevirapine, and rilpivirine.

Examples of HIV protease inhibitors include amprenavir, atazanavir, darunavir, fosamprenavir, indinavir, lopinavir, nelfinavir, ritonavir, saquinavir and, tipranavir.

An example of an HIV fusion inhibitor is enfuvirtide or T-1249.

An example of an HIV entry inhibitor is maraviroc.

Examples of HIV integrase inhibitors include dolutegravir, elvitegravir, or raltegravir.

An example of an HIV attachment inhibitor is fostemsavir.

An example of an HIV maturation inhibitor is BMS-955176, having the following structure:

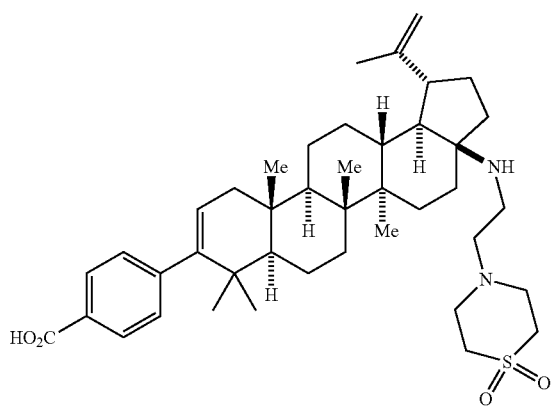

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| Drug Name | Manufacturer | Indication |
|---|---|---|
| ANTIVIRALS | | |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |

-continued

| Drug Name | Manufacturer | Indication |
|---|---|---|
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/ Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDs in development |
| CMX-157 Lipid conjugate of nucleotide tenofovir | Chimerix | HIV infection AIDs |
| GSK1349572 Integrase inhibitor TIVICAY ® dolutegravir | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |

-continued

| Drug Name | Manufacturer | Indication |
|---|---|---|
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |

-continued

| Drug Name | Manufacturer | Indication |
|---|---|---|
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Methods of Synthesis

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced. Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compounds I-1 and I-6 are commercially available or synthesized by reactions well known in the art. Treatment of compound I-1 with bromine provided the dibromo intermediates I-2 which was converted to the chloropyridine I-3 by reacting with POCl$_3$. Intermediate I-3 conveniently transformed to ketoester I-5 using conditions well-known to those skilled in the art, including reacting I-3 with Grignard reagent in the presence of catalytic copper(I) bromide dimethylsulfide complex followed by alkyl 2-chloro-2-oxoacetate. Chiral Lewis acid such as I-6 mediated reduction of ketoester I-5 with catecholborane furnished chiral alcohol I-7. Treatment of hydrochloride salt of I-7 with excess sodium iodide in reflux acetonitrile would furnish iodo intermediate I-8. Tertiary butylation of alcohol I-8 by well-known conditions, including but not limited to tertiary-butyl acetate and perchloric acid, gave intermediate I-9. Intermediates I-9 are conveniently transformed to intermediates I-11 using conditions well-known in the art, including but not limited to the Suzuki coupling between intermediates I-9 and boronic derivatives Ar$^1$B(OR)$_2$ followed Ar$^2$B(OR)$_2$. The boronate or boronic acid coupling reagents, well-known in the art, are commercially available or are prepared by reactions well-known to those skilled in the art. Hydrolysis of intermediate I-11 by using conditions well-known to those skilled in the art furnished carboxylic acid I-12.

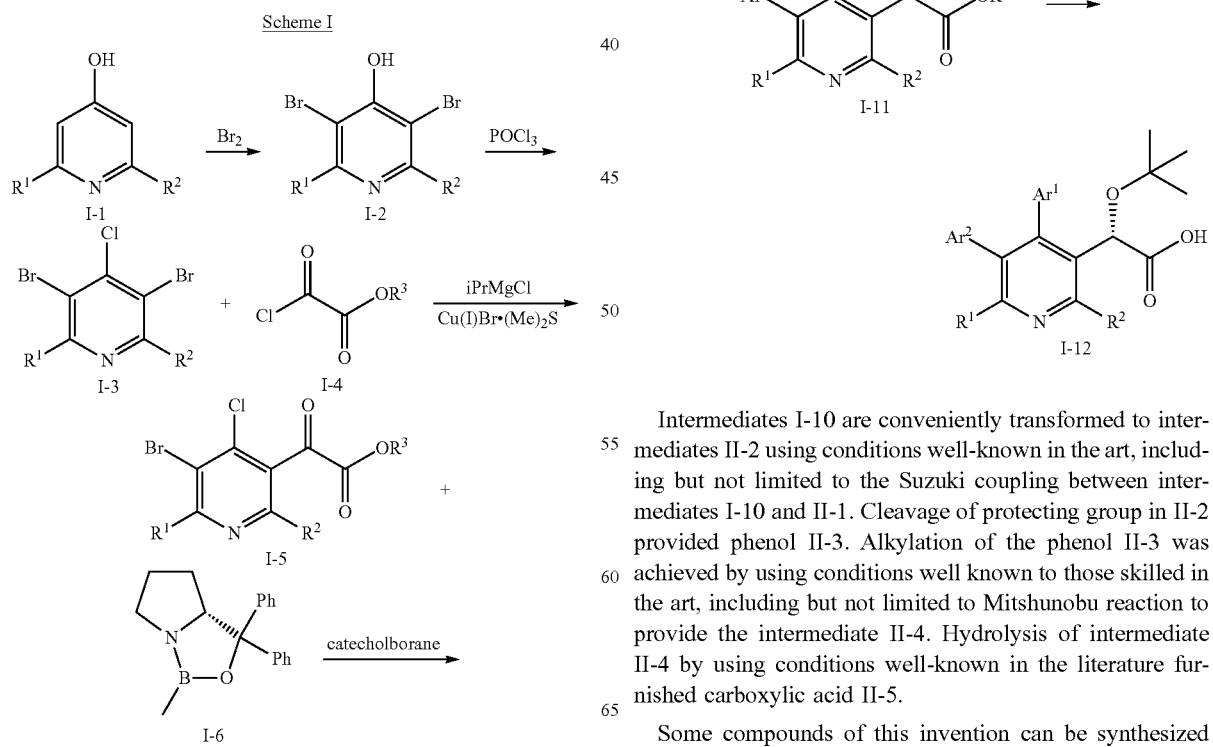

Scheme I

Intermediates I-10 are conveniently transformed to intermediates II-2 using conditions well-known in the art, including but not limited to the Suzuki coupling between intermediates I-10 and II-1. Cleavage of protecting group in II-2 provided phenol II-3. Alkylation of the phenol II-3 was achieved by using conditions well known to those skilled in the art, including but not limited to Mitsunobu reaction to provide the intermediate II-4. Hydrolysis of intermediate II-4 by using conditions well-known in the literature furnished carboxylic acid II-5.

Some compounds of this invention can be synthesized according to Scheme II.

Scheme II

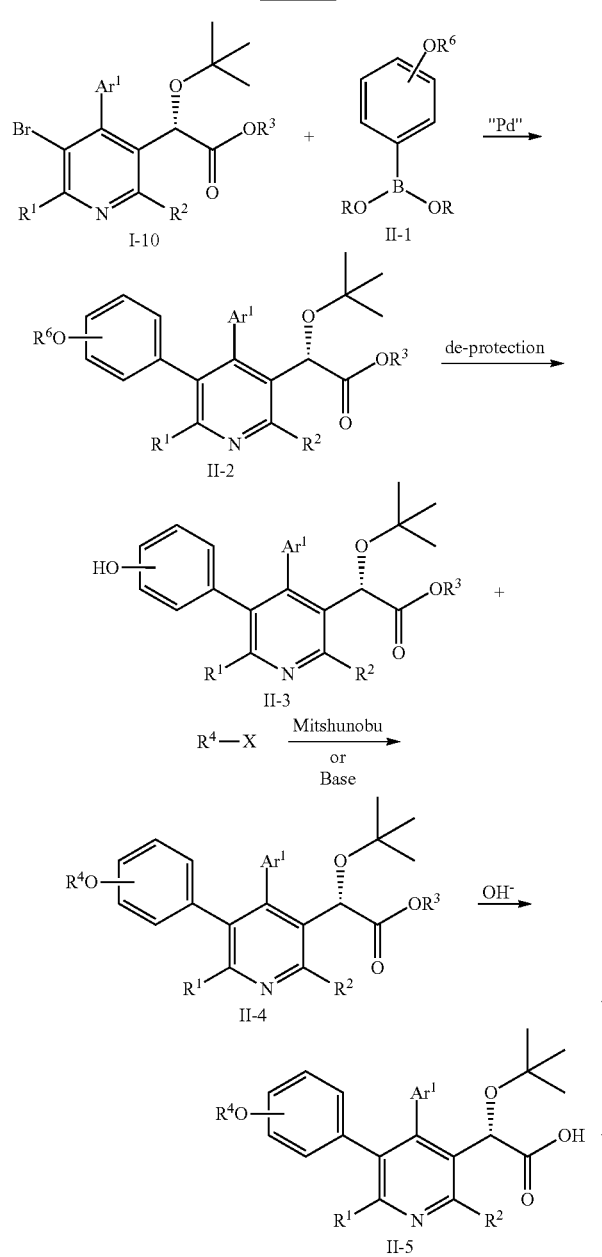

Some compounds of this invention can be synthesized according to Scheme III.

Scheme III

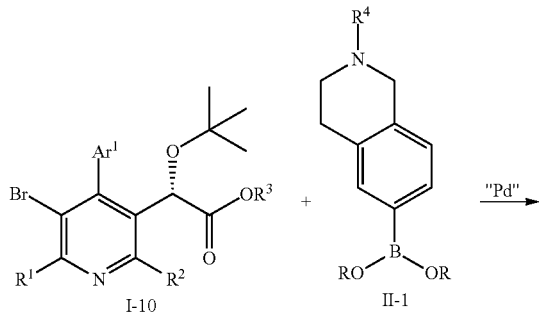

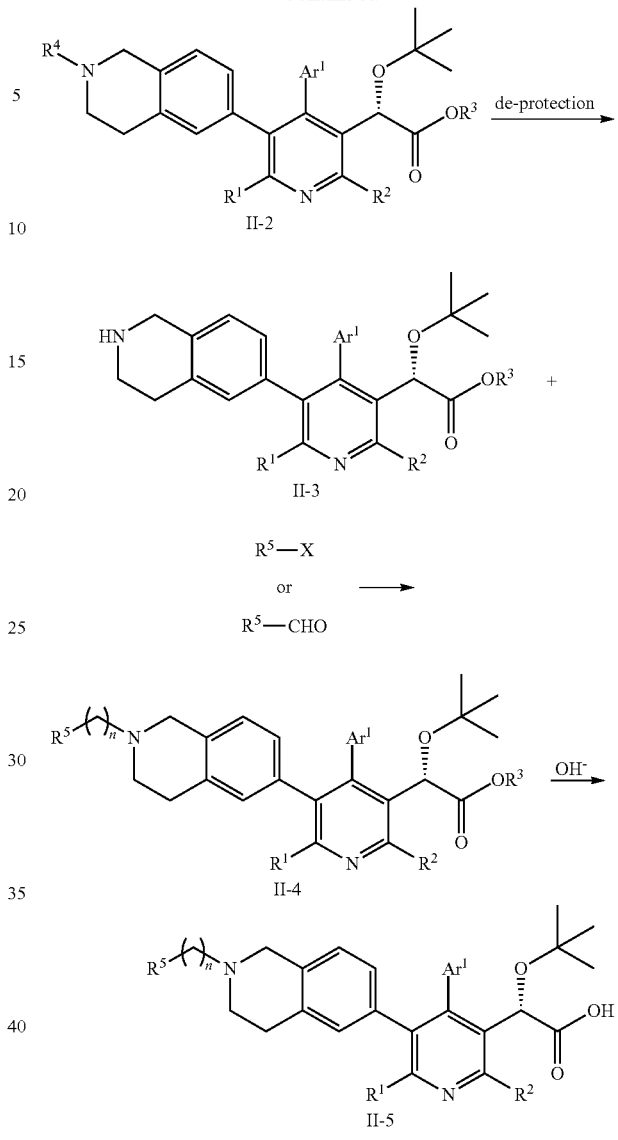

Some compounds of this invention can be synthesized according to Scheme IV. In Scheme IV, pyridine IV-1, can be produced using methods similar to those described in the previous schemes. This intermediate can be carried on to the final product according to a variety of paths. In one, the C2 and C6 alkyl groups can be oxidized to furnish intermediates IV-3 and/or IV-4 which can be further transformed to final compounds IV-9 or IV-10 by several paths.

Scheme IV

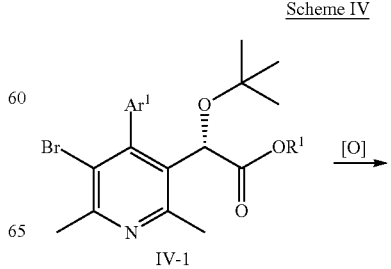

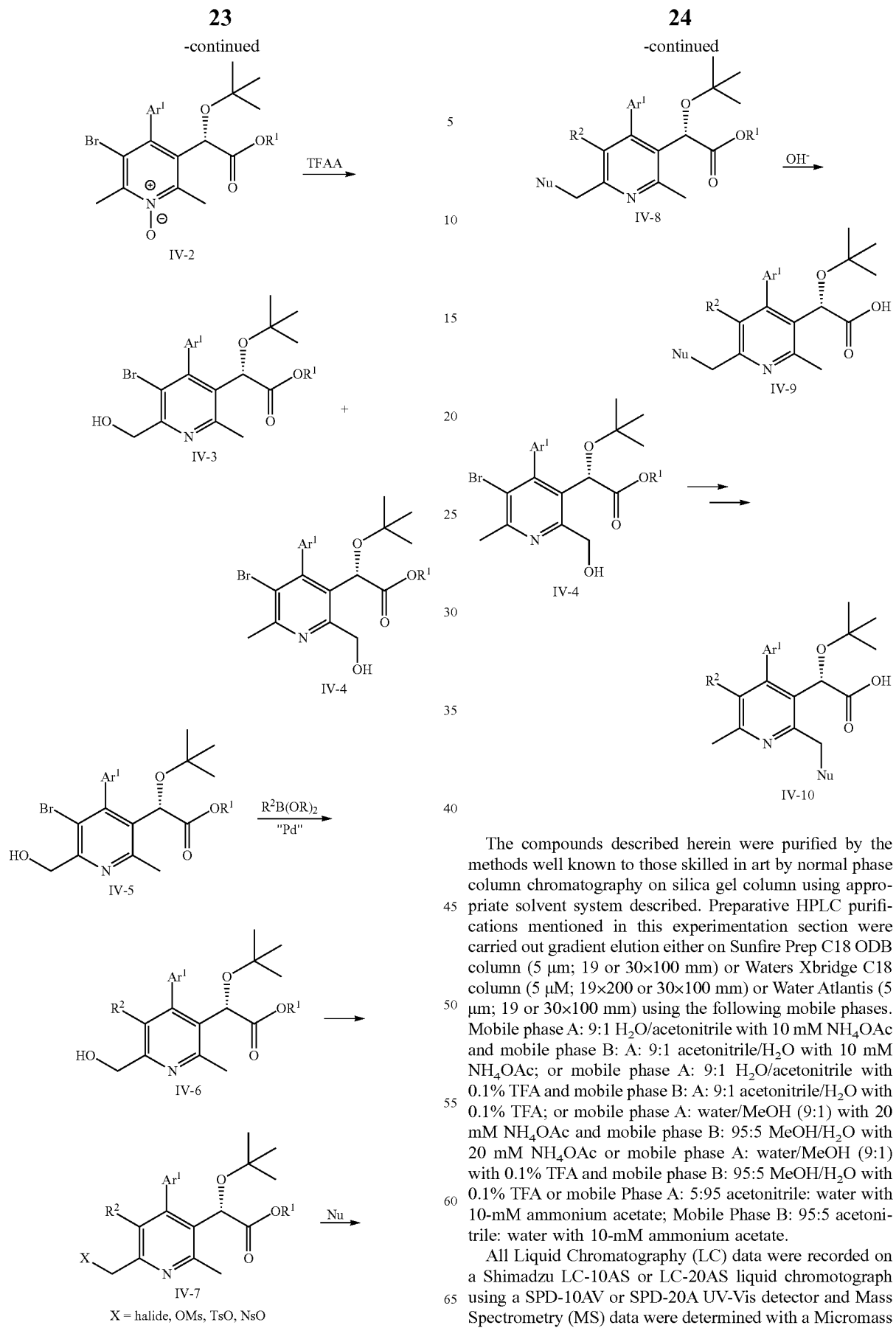

The compounds described herein were purified by the methods well known to those skilled in art by normal phase column chromatography on silica gel column using appropriate solvent system described. Preparative HPLC purifications mentioned in this experimentation section were carried out gradient elution either on Sunfire Prep C18 ODB column (5 μm; 19 or 30×100 mm) or Waters Xbridge C18 column (5 μM; 19×200 or 30×100 mm) or Water Atlantis (5 μm; 19 or 30×100 mm) using the following mobile phases. Mobile phase A: 9:1 H$_2$O/acetonitrile with 10 mM NH$_4$OAc and mobile phase B: A: 9:1 acetonitrile/H$_2$O with 10 mM NH$_4$OAc; or mobile phase A: 9:1 H$_2$O/acetonitrile with 0.1% TFA and mobile phase B: A: 9:1 acetonitrile/H$_2$O with 0.1% TFA; or mobile phase A: water/MeOH (9:1) with 20 mM NH$_4$OAc and mobile phase B: 95:5 MeOH/H$_2$O with 20 mM NH$_4$OAc or mobile phase A: water/MeOH (9:1) with 0.1% TFA and mobile phase B: 95:5 MeOH/H$_2$O with 0.1% TFA or mobile Phase A: 5:95 acetonitrile: water with 10-mM ammonium acetate; Mobile Phase B: 95:5 acetonitrile: water with 10-mM ammonium acetate.

All Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

Compounds purified by preparative HPLC were diluted in methanol (1.2 mL) or DMF and purified using a Shimadzu LC-8A or LC-10A automated preparative HPLC system.

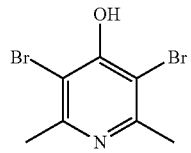

3,5-Dibromo-2,6-dimethylpyridin-4-ol

A 3-neck R.B-flask equipped with mechanical stirrer, addition funnel and condenser is charged with 2,6-dimethylpyridin-4-ol (100 g, 812 mmol), CH$_2$Cl$_2$ (1000 mL) and MeOH (120 mL). To the resulting light brown or tan solution was added tert-BuNH$_2$ (176 ml, 1665 mmol), cooled in water bath maintained between 5-10° C. (ice-water) and added drop wise Br2 (84 ml, 1624 mmol) over 70 min. After the addition was complete cold bath was removed and stirred for 1.5 h at rt. Then, the light orange slurry was filtered and the filter cake was washed with ether (250 mL) and dried to afford 3,5-dibromo-2,6-dimethylpyridin-4-ol, hydrobromide (280.75 g, 776 mmol, 96% yield) as white solid which was used in the next step without further purification. $^1$H NMR (500 MHz, DMSO-d$_6$) δ 12.08 (br. s., 1H), 2.41 (s, 6H). LCMS (M+H)=281.9.

Alternative Procedure:

Bromine (72.8 mL, 1.4 mol) was added via addition funnel over 60 min to a mechanically stirred cold (ice-water bath) solution of 2,6-dimethylpyridin-4-ol (87 g, 706 mmol) and 4-methylmorpholine (156 mL, 1.4 mol) in dichloromethane (1 L) and methanol (100 mL) and then stirred for 2 h at rt. Additional bromine (~15 mL) was added based on monitoring by LCMS. The product was filtered, washed with ether, and dried under vacuum to give 3,5-dibromo-2, 6-dimethylpyridin-4-ol 176.8 g (88%).

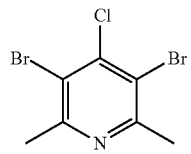

3,5-Dibromo-4-chloro-2,6-dimethyl-pyridine

Triethylamine (28.8 mL, 206 mmol) was added to a nitrogen purged solution of 3,5-dibromo-2,6-dimethylpyridin-4-ol (58 g, 206 mmol) and phosphorous oxychloride (57.7 mL, 619 mmol) in chloroform (450 mL) and stirred for 1 h at rt, then 3 h at 80° C. The reaction was removed from heating and immediately concentrated under house vacuum; then under high vacuum. The appearance was a cream colored solid, which was azeotroped with toluene (2×100 mL); treated with ice (200 g) for 10 min and carefully neutralized with NaHCO$_3$ (powder), and 1N NaOH solution, and extracted with DCM (2×400 mL). The combined organic layers were dried (MgSO$_4$), concentrated, and a beige solid was obtained that was washed with hexanes and dried under high vacuum to give 3,5-dibromo-4-chloro-2,6-dimethyl-pyridine 52.74 g (85.1%). Concentration of the hexanes gave 3.5 g of less pure product. $^1$H NMR (500 MHz, CDCl$_3$) δ 2.59 (s, 6H). LCMS (M+H)=300.0.

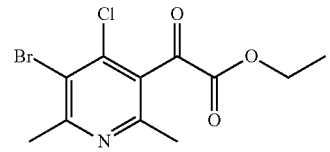 [SMILES: CCOC(=O)C(=O)c1c(C)nc(C)c(Br)c1Cl]

Ethyl 2-(5-bromo-4-chloro-2,6-dimethylpyridin-3-yl)-2-oxoacetate

To a stirred mixture of 3,5-dibromo-4-chloro-2,6-dimethylpyridine (14.94 g, 49.9 mmol) and Cu(I)Br Me$_2$S (0.513 g, 2.495 mmol) in THF (50 mL) was added dropwise 2M iPrMgCl/THF (26.2 ml, 52.4 mmol) at −60° C. over 5 min. Then, the resulting dark reaction mixture was warmed to −15° C. over min 30 min and stirred for 30 min. Then, this reaction mixture was rapidly transferred via cannula to a solution of ethyl 2-chloro-2-oxoacetate (6.14 ml, 54.9 mmol) in THF (50 mL) maintained at −50° C. The resulting reaction mixture was stirred (1.5 h) while warming to 0° C. Then, taken up in to Et$_2$O (200 mL), washed with 1:1 sat Na$_2$CO$_3$/1M NH$_4$Cl (3×50 mL), dried (MgSO$_4$), filtered and concentrated to give brown viscous oil. Flash chromatography using 2.5, 5 and 7.5% EtOAc/Hex afforded ethyl 2-(5-bromo-4-chloro-2,6-dimethylpyridin-3-yl)-2-oxoacetate (14.37 g, 44.8 mmol, 90% yield) as white solid. $^1$H NMR (400 MHz, CDCl$_3$) δ 4.42 (q, J=7.0 Hz, 2H), 2.76 (s, 3H), 2.46 (s, 3H), 1.41 (t, J=7.2 Hz, 3H). LCMS (M+H)= 322.1.

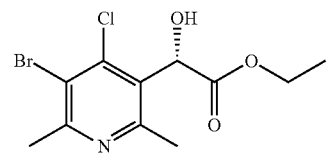

(S)-Ethyl 2-(5-bromo-4-chloro-2,6-dimethylpyridin-3-yl)-2-hydroxyacetate

To a stirred solution of ethyl 2-(5-bromo-4-chloro-2,6-dimethylpyridin-3-yl)-2-oxoacetate (3.21 g, 10 mmol) and (R)-1-methyl-3,3-diphenylhexahydropyrrolo[1,2-c][1,3,2] oxazaborole (0.554 g, 2.000 mmol) in toluene (30 mL) was added dropwise catecholborane (3.00 ml, 14.00 mmol) at −30° C. over 5 min. Then, slowly warmed to −15° C. and left at this temperature overnight (15 h). Then, diluted with EtOAc (150 mL) and sat Na$_2$CO$_3$ (50 mL). The mixture was vigorously stirred for 15 min, aq layer separated and org layer washed with sat Na$_2$CO$_3$ (2×50 mL) by vigarously stirring for 15 min, dried (MgSO$_4$), filtered, concentrated and purified by flash chromatography using 10, 20, 25 and 30% EtOAc/Hex to afford (S)-ethyl 2-(5-bromo-4-chloro-2, 6-dimethylpyridin-3-yl)-2-hydroxyacetate (3.2 g, 9.92 mmol, 99% yield) as pale amber color viscous oil. $^1$H NMR (400 MHz, CDCl$_3$) δ 5.70 (d, J=2.8 Hz, 1H), 4.24-4.33 (m, 2H), 3.56 (d, J=3.3 Hz, 1H), 2.71 (s, 3H), 2.57 (s, 3H), 1.25 (t, J=7.2 Hz, 3H). LCMS (M+H)=324.05.

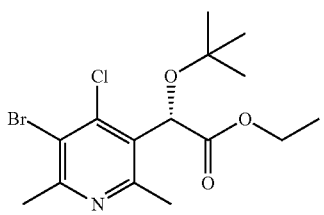 [SMILES: CCOC(=O)[C@@H](OC(C)(C)C)c1c(C)nc(C)c(Br)c1Cl]

(S)-Ethyl 2-(5-bromo-4-chloro-2,6-dimethylpyridin-3-yl)-2-(tert-butoxy)acetate

To a stirred mixture of (S)-ethyl 2-(5-bromo-4-chloro-2,6-dimethylpyridin-3-yl)-2-hydroxyacetate (2.927 g, 9.07 mmol) and t-BuOAc (49.0 ml, 363 mmol) in $CH_2Cl_2$ (100 mL) was added 70% HClO4 (2.339 ml, 27.2 mmol) and sealed with septa. After 2.5 h, the reaction mixture diluted with ether (100 mL) and washed with sat. $Na_2CO_3$ (3×25 mL), org layer dried ($MgSO_4$), filtered, concentrated and purified by flash chromatography using 5, 10, 30 and 40% EtOAc/Hex to afford desired (S)-ethyl 2-(5-bromo-4-chloro-2,6-dimethylpyridin-3-yl)-2-(tert-butoxy)acetate (2.4762 g, 6.54 mmol, 72.1% yield). LCMS (M+H)=378.2.

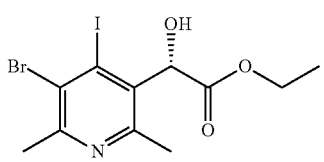 [SMILES: CCOC(=O)[C@@H](O)c1c(C)nc(C)c(Br)c1I]

(S)-Ethyl 2-(5-bromo-4-iodo-2,6-dimethylpyridin-3-yl)-2-hydroxyacetate

To a stirred solution of (S)-ethyl 2-(5-bromo-4-chloro-2,6-dimethylpyridin-3-yl)-2-hydroxyacetate (0.367 g, 1.138 mmol) in ether (10 mL) was added dropwise 2M HCl/$Et_2O$ (2 ml, 4.00 mmol) and the resulting white slurry stirred for 30 min and concentrated to give white powder.

A mixture of above white solid and NaI (0.853 g, 5.69 mmol) in acetonitrile (10 mL) was heated at reflux for 16 h. Then, cooled, diluted with sat $Na_2CO_3$ (20 mL), extracted with $CH_2Cl_2$ (2×25 mL). The combined org layers dried ($MgSO_4$), filtered, concentrated and purified by flash chromatography using 20 and 30% EtOAc/Hex to afford (S)-ethyl 2-(5-bromo-4-iodo-2,6-dimethylpyridin-3-yl)-2-hydroxyacetate (0.438 g, 1.058 mmol, 93% yield) as white solid. $^1$H NMR (400 MHz, CDCl$_3$) δ 5.83 (d, J=2.5 Hz, 1H), 4.24-4.34 (m, 2H), 3.51 (d, J=2.5 Hz, 1H), 2.78 (s, 3H), 2.51 (s, 3H), 1.26 (t, J=7.2 Hz, 3H). LCMS (M+H)=416.1.

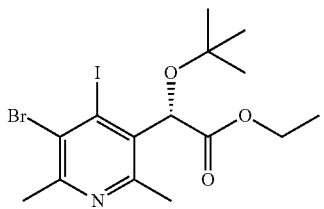 [SMILES: CCOC(=O)[C@@H](OC(C)(C)C)c1c(C)nc(C)c(Br)c1I]

(S)-ethyl 2-(5-bromo-4-iodo-2,6-dimethylpyridin-3-yl)-2-(tert-butoxy)acetate

A stirred cold (ice-water bath) mixture of (S)-ethyl 2-(5-bromo-4-iodo-2,6-dimethylpyridin-3-yl)-2-hydroxyacetate (2.69 g, 6.50 mmol) and 70% HClO$_4$ (0.614 ml, 7.15 mmol) in DCM (100 mL) was saturated with isobutylene by bubbling through the reaction mixture for 10 min. After 1 h, cold bath was removed, stirred for 15 h at rt and stirred with sat Na$_2$CO$_3$ (20 mL) for 10 min. Organic separated, dried (MgSO$_4$), filtered, concentrated and purified by flash chromatography using 5, 10, 30 and 40% EtOAc/Hex to afford desired (S)-ethyl 2-(5-bromo-4-iodo-2,6-dimethylpyridin-3-yl)-2-(tert-butoxy)acetate (02.4528 g, 5.22 mmol, 80% yield). $^1$H NMR (500 MHz, CDCl$_3$) δ 5.70 (br. s., 1H), 4.14-4.24 (m, 2H), 2.77 (br. s., 3H), 2.58 (br. s., 3H), 1.24 (br. s., 9H), 1.23 (t, J=7.2 Hz, 3H). LCMS (M+H)=472.1.

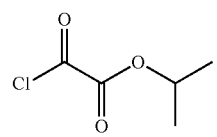

2-Chloro-2-oxoacetate

The propan-2-ol (38.2 mL, 499 mmol) was added drop wise over 15 min to a cold (0° C.), nitrogen purged solution of oxalyl chloride (101 g, 799 mmol) and the reaction was stirred at room temperature for 2.5 h. Then a reflux condenser was fitted and a slight vacuum was applied for about 1 h until HCl gas was removed (the HCl was trapped in by a sat'd solution of NaHCO$_3$). The reflux condenser was removed and the flask was fitted with a short path distillation head. Excess reagent was removed by distillation under house vacuum (oil bath heated to 65° C.), and then the temperature was raised to between 85-95° C. and the product was distilled (NOTE: The 1$^{st}$ fraction of ~5 mL was discarded) to provide isopropyl 2-chloro-2-oxoacetate 52.62 g (70%).

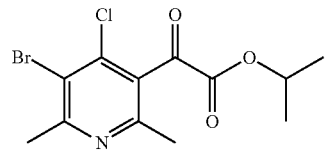 [SMILES: Cc1nc(C)c(C(=O)C(=O)OC(C)C)c(Cl)c1Br]

2-(5-Bromo-4-chloro-2,6-dimethylpyridin-3-yl)-2-oxoacetate

A solution of 2M isopropyl magnesium chloride (84 mL, 168 mmol) was added drop wise over 20 min to a cold (~70° C.), nitrogen purged solution of 3,5-dibromo-4-chloro-2,6-dimethylpyridine (48 g, 160 mmol) and copper(I)bromide-dimethyl sulfide complex (1.65 g, 8.02 mmol) in THF (240 mL), which was then allowed to warm to −10° C. over 60 min. The reaction mixture was transferred via cannula into a 1 L RB-flask containing isopropyl 2-chloro-2-oxoacetate (26.6 g, 176 mmol) in THF (160 mL) maintained at −60° C., and the reaction stirred an additional 2.5 h while being allowed to warm to −10° C. The reaction was quenched upon diluted with a mixture of 10% NH$_4$Cl solution (80 mL) in ether (320 mL). The organic layer was washed with 160 mL of sat'd NaHCO$_3$/10% NH$_4$Cl solution (1:1), brine, and dried (Na$_2$SO$_4$). The crude product was charged (DCM solution) to a 330 g ISCO silica gel cartridge and gradient eluted (5-20% EtOAc/hexanes) using an Isolera chromatography station gave isopropyl 2-(5-bromo-4-chloro-2,6-dimethylpyridin-3-yl)-2-oxoacetate 40.38 g (76%). ¹H NMR (500 MHz, CDCl₃) δ 5.28-5.21 (m, 1H), 2.77 (s, 3H), 2.47 (s, 3H), 1.40 (d, J=6.3 Hz, 6H). LCMS (M+H)=336.04.

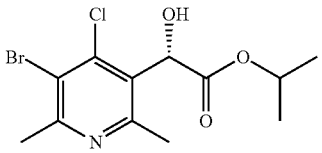

(S)-Isopropyl 2-(5-bromo-4-chloro-2,6-dimethyl-pyridin-3-yl)-2-hydroxyacetate

To a stirred solution of isopropyl 2-(5-bromo-4-chloro-2,6-dimethylpyridin-3-yl)-2-oxoacetate (24.2 g, 72.3 mmol) and (R)-1-methyl-3,3-diphenylhexahydropyrrolo[1,2-c][1,3,2]oxazaborole (10 mL, 10.00 mmol) in toluene (30 mL) was added dropwise catecholborane (22 mL, 103 mmol) at −30° C. over 5 min. Then, the reaction mixture was slowly warmed to −15° C. and left at this temperature overnight (15 h). The reaction mixture was diluted with EtOAc (150 mL) and satd. Na₂CO₃ (50 mL). The mixture was vigarously stirred for 15 min, aq. layer was separated and organic layer washed with satd. Na₂CO₃ (2×50 mL) by vigorously stirring for 15 min, dried (MgSO₄), filtered, concentrated and purified by flash chromatography to afford (S)-isopropyl 2-(5-bromo-4-chloro-2,6-dimethylpyridin-3-yl)-2-hydroxyacetate (21.5 g, 63.9 mmol, 88% yield) as pale amber color viscous oil. ¹H NMR (400 MHz, CDCl₃) δ 5.15 (dt, J=12.5, 6.3 Hz, 1H), 2.71 (s, 3H), 2.56 (s, 3H), 1.26 (d, J=6.5 Hz, 3H), 1.20 (d, J=6.3 Hz, 3H). LCMS (M+H)=336.2.

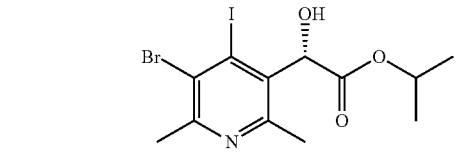 [SMILES: Cc1nc(C)c([C@H](O)C(=O)OC(C)C)c(I)c1Br]

(S)-Isopropyl 2-(5-bromo-4-iodo-2,6-dimethylpyridin-3-yl)-2-hydroxyacetate

To a stirred solution of (S)-isopropyl 2-(5-bromo-4-chloro-2,6-dimethylpyridin-3-yl)-2-hydroxyacetate (21.5 g, 63.9 mmol) in ether (50 mL) was added dropwise 2M HCl/Et₂O (2 ml, 4.00 mmol) at 0° C. and the resulting white slurry stirred at rt for 30 min and concentrated to give white powder.

The above white solid and NaI (20 g, 133 mmol) in anhydrous MeCN (100 mL) was heated at reflux for 2 days. Then, cooled, diluted with satd. Na₂CO₃ (20 mL), extracted with CH₂Cl₂ (2×100 mL). The combined org layers was dried (MgSO₄), filtered, concentrated and purified by flash chromatography using (EtOAc/Hex: 20 to 30%) to afford (S)-isopropyl 2-(5-bromo-4-iodo-2,6-dimethylpyridin-3-yl)-2-hydroxyacetate (24.3 g, 56.8 mmol, 89% yield) as a white solid. ¹H NMR (500 MHz, CDCl₃) δ 5.80 (d, J=2.5 Hz, 1H), 5.21-5.03 (m, 1H), 3.52 (br. s., 1H), 2.79 (s, 3H), 2.52 (s, 3H), 1.29 (d, J=6.3 Hz, 3H), 1.22 (d, J=6.3 Hz, 3H). LCMS (M+H)=430.1.

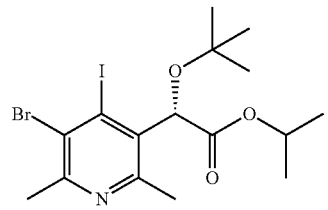 [SMILES: Cc1nc(C)c([C@H](OC(C)(C)C)C(=O)OC(C)C)c(I)c1Br]

(S)-Isopropyl 2-(5-bromo-4-iodo-2,6-dimethylpyridin-3-yl)-2-(tert-butoxy)acetate A stirred ice-cold yellow mixture of (S)-isopropyl 2-(5-bromo-4-iodo-2,6-dimethylpyridin-3-yl)-2-hydroxyacetate (24.3 g, 56.8 mmol) and 70% HClO₄ (7.32 mL, 85 mmol) in dichloromethane (100 mL) was saturated with isobutylene gas by bubbling through the reaction mixture. After 2 h, cold bath was removed, sealed and the tubid reaction mixture was stirred at rt for 4 days. The reaction mixture was neutralized with satd. Na₂CO₃, organic layer was separated and aqueous layer was extracted with CH₂Cl₂. The combined organic layers dried (MgSO₄), filtered, concentrated and purified by flash chromatography to afford (S)-isopropyl 2-(5-bromo-4-iodo-2,6-dimethylpyridin-3-yl)-2-(tert-butoxy)acetate (21.5 g, 44.4 mmol, 78% yield) as white solid. ¹H NMR (500 MHz, CDCl₃) δ 5.66 (s, 1H), 5.10-5.01 (m, 1H), 2.77 (s, 3H), 2.58 (s, 3H), 1.28-1.22 (m, 12H), 1.16 (d, J=6.1 Hz, 3H). LCMS (M+H)=485.5.

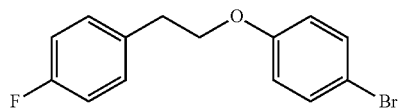 [SMILES: Fc1ccc(CCOc2ccc(Br)cc2)cc1]

1-Bromo-4-(4-fluorophenethoxy)benzene

To a stirred solution of 4-bromophenol (81.7 g, 472 mmol), 2-(4-fluorophenyl)ethanol (79 g, 567 mmol) and Ph₃P (149 g, 567 mmol) in THF (100 mL) cooled in an ice-water bath was added drop wise DEAD (93 ml, 590 mmol) over 20 min. Note: The reaction is exothermic and efficient cooling is highly recommended before initiating large scale reaction. After 1 h, cold bath was removed and stirred overnight (17 h) at rt. Then, the reaction mixture was concentrated, the resulting residue triturated with hexanes, filtered and the filter cake washed with 10% ether/hexanes (2-lit). The filtrate was concentrated and purified by flash chromatography (silica gel column 3"×11") using 4-lit hexanes and 2-lit 2% EtOAc/Hex to afford 1-bromo-4-(4-fluorophenethoxy)benzene (142 g, 469 mmol, 99% yield) as colorless liquid (contaminated with ~2.5% Ph₃P by ¹HNMR). ¹H NMR (500 MHz, CDCl₃) δ 7.41-7.36 (m, 2H), 7.28-7.22 (m, 2H), 7.05-6.99 (m, 2H), 6.82-6.76 (m, 2H), 4.14 (t, J=6.9 Hz, 2H), 3.08 (t, J=6.9 Hz, 2H).

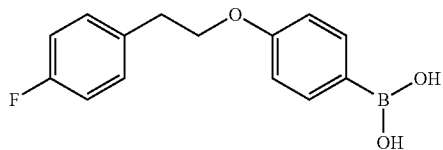 [SMILES: OB(O)c1ccc(OCCc2ccc(F)cc2)cc1]

(4-(4-Fluorophenethoxy)phenyl)boronic Acid

To a stirred solution of 1-bromo-4-(4-fluorophenethoxy)benzene (142 g, 469 mmol) in THF (1000 mL) was added 2M n-BuLi/cyclohexane (293 ml, 586 mmol) over 15 min at −78° C. After 1.5 h, triisopropyl borate (131 ml, 563 mmol) was added to the light pink reaction mixture over 5 min and stirred for 2 h at −78° C. Then, the reaction was quenched by careful addition of 3M HCl (375 mL), cold bath was replaced with water bath, stirred for 1 h, diluted with ether (500 mL), aq. layer separated and organic layer washed with water (2×200 mL). The combined aq. layers extracted with ether (200 mL) and combined ether layers washed with brine (100 mL), dried (MgSO$_4$), filtered and concentrated to 200 mL. To this was added 250 mL hexanes and concentrated to about 300 mL and allowed to stand at rt. The precipitated solid was triturated with hexanes and filtered to give white solid which was used in next step without purification. $^1$H NMR (500 MHz, CDCl$_3$) δ 8.18-8.15 (m, 2H), 7.32-7.28 (m, 2H), 7.07-7.00 (m, 4H), 4.26 (t, J=6.9 Hz, 2H), 3.14 (t, J=6.9 Hz, 2H).

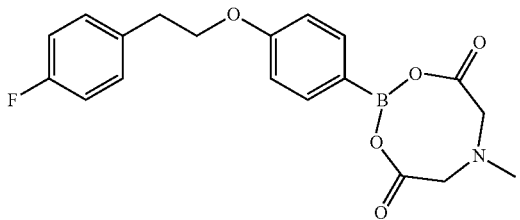 [SMILES: CN1CC(=O)OB(c2ccc(OCCc3ccc(F)cc3)cc2)OC(=O)C1]

2-(4-(4-Fluorophenethoxy)phenyl)-6-methyl-1,3,6,2-dioxazaborocane-4,8-dione

A slurry of (4-(4-fluorophenethoxy)phenyl)boronic acid (122 g, 469 mmol) and 2,2'-(methylazanediyl)diacetic acid (76 g, 516 mmol) in anhydrous toluene (500 mL) and DMSO (200 mL) was refluxed for 4 h. Then, cooled, diluted with EtOAc (500 mL), washed with water (5×200 mL), brine (2×100 mL), dried (MgSO$_4$), filtered and concentrated to give light orange foam which was purified by flash chromatography using 5-40% acetone/CH$_2$Cl$_2$ (5% increment per 2-lit) to afford 2-(4-(4-fluorophenethoxy)phenyl)-6-methyl-1,3,6,2-dioxazaborocane-4,8-dione (131.38 g, 354 mmol, 75% yield) as white solid. $^1$H NMR (500 MHz, CDCl$_3$) δ 7.43 (d, J=8.4 Hz, 2H), 7.28-7.24 (m, 2H), 7.04-6.99 (m, 2H), 6.92 (d, J=8.5 Hz, 2H), 4.17 (t, J=6.9 Hz, 2H), 4.00 (d, J=16.6 Hz, 2H), 3.76 (d, J=16.6 Hz, 2H), 3.08 (t, J=6.8 Hz, 2H), 2.54 (s, 3H). LCMS (M+H)=372.3.

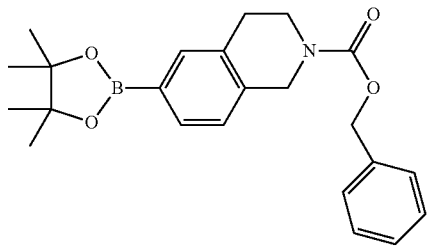 [SMILES: CC1(C)OB(c2ccc3c(c2)CCN(C(=O)OCc2ccccc2)C3)OC1(C)C]

Benzyl 6-(4,4,5,5-tetramethyl-1,3,2-dioxaborolan-2-yl)-3,4-dihydroisoquinoline-2(1H)-carboxylate A mixture of benzyl 6-bromo-3,4-dihydroisoquinoline-2 (1H)-carboxylate (8.16 g, 23.57 mmol), KOAc (7 g, 71.3 mmol) and 4,4,4',4',5,5,5',5'-octamethyl-2,2'-bi(1,3,2-dioxaborolane) (12 g, 47.3 mmol) in dioxane (50 mL) was purged with N2 for 15 min, and added Pd(Ph$_3$P)$_4$ (0.35 g, 0.303 mmol), further purged N2 for 5 min. The reaction mixture was stirred in 80° C. bath for 18 h. The mixture was diluted with EtOAc and washed water, brine, and, evaporated solvent and purified on Biotage 220 g column (0-50% EtOAc/Hex) to afford benzyl 6-(4,4,5,5-tetramethyl-1,3,2-dioxaborolan-2-yl)-3,4-dihydroisoquinoline-2(1H)-carboxylate as colorless viscous oil (7.8 g, 84%). $^1$H NMR (500 MHz, CDCl$_3$) δ 7.68-7.59 (m, 2H), 7.46-7.33 (m, 5H), 7.14 (d, J=15.6 Hz, 1H), 5.21 (s, 2H), 4.69 (s, 2H), 3.75 (br. s., 2H), 2.89 (br. s., 2H), 1.37 (s, 12H). LCMS (M+H)=394.4.

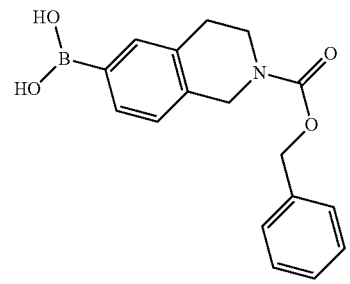 [SMILES: O=C(OCc1ccccc1)N1CCc2cc(B(O)O)ccc2C1]

(2-((Benzyloxy)carbonyl)-1,2,3,4-tetrahydroisoquinolin-6-yl)boronic Acid

To a solution of benzyl 6-(4,4,5,5-tetramethyl-1,3,2-dioxaborolan-2-yl)-3,4-dihydroisoquinoline-2(1H)-carboxylate (2.2 g, 5.59 mmol) in acetone (10 mL)/Water (5.00 mL) was added NaIO$_4$ (3.59 g, 16.78 mmol) and NH$_4$OAc (1.294 g, 16.78 mmol) and the resulting mixture was stirred at room temp for 16 h and another portion of NH$_4$OAc (1.294 g, 16.78 mmol) and NaIO$_4$ (3.59 g, 16.78 mmol) was added. The mixture was stirred at rt for 3 h and 1N HCl (15 mL) was added and the mixture was stirred for 1 h. The mixture was then diluted with EtOAc and washed with brine, dried (Na$_2$SO$_4$), filtered and concentrated to afford (2-((benzyloxy)carbonyl)-1,2,3,4-tetrahydroisoquinolin-6-yl)boronic acid (1.2 g, 3.86 mmol, 68.9% yield) as white solid.

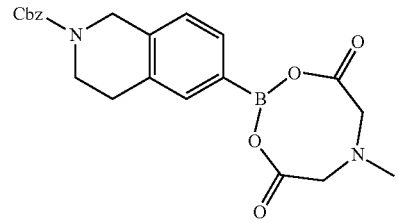 [SMILES: CN1CC(=O)OB(c2ccc3c(c2)CCN(C(=O)OCc2ccccc2)C3)OC(=O)C1]

Benzyl 6-(6-methyl-4,8-dioxo-1,3,6,2-dioxazaborocan-2-yl)-3,4-dihydroisoquinoline-2(1H)-carboxylate A mixture of (2-((benzyloxy)carbonyl)-1,2,3,4-tetrahydroisoquinolin-6-yl)boronic acid (41 g, 132 mmol) and 2,2'-(methylazanediyl)diacetic acid (19.39 g, 132 mmol) in anhydrous toluene (250 mL) and DMSO (100 mL) was refluxed for 20 h. The reaction mixture was cooled and partitioned between water and EtOAc. The aqueous layer was extracted with EtOAc (3×), the combined organic solution was washed with brine, dried (MgSO$_4$), concentrated and purified on ISCO 330 g column (3×; ~⅓ each time. EtOAc/hexane: 5 to 100%, then MeOH/EtOAc: 8%;) to afford benzyl 6-(6-methyl-4,8-dioxo-1,3,6,2-dioxazaborocan-2-yl)-3,4-dihydroisoquinoline-2(1H)-carboxylate as a white solid. LCMS (M+H)=423.3. $^1$H NMR (500 MHz, CDCl$_3$) δ 7.45-7.30 (m, 7H), 7.17 (br. s., 1H), 5.21 (s, 2H), 4.68 (s, 2H), 3.94 (d, J=16.2 Hz, 2H), 3.79 (d, J=16.4 Hz, 2H), 3.77-3.70 (m, 2H), 2.88 (br. s., 2H), 2.60 (s, 3H).

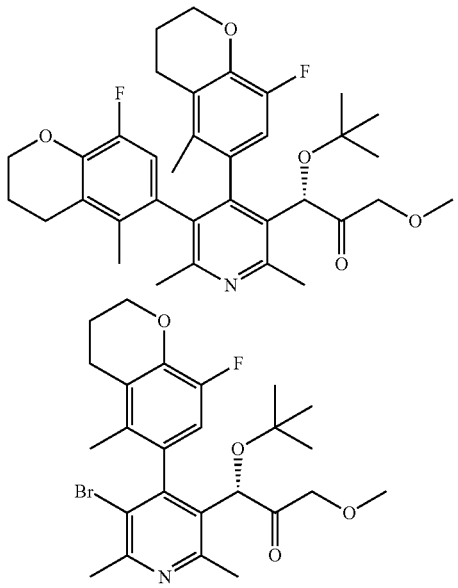

(2S)-Bthyl 2-(4,5-bis(8-fluoro-5-methylchroman-6-yl)-2,6-dimethylpyridin-3-yl)-2-(tert-butoxy)acetate A stirred mixture of (S)-ethyl 2-(5-bromo-4-iodo-2,6-dimethylpyridin-3-yl)-2-(tert-butoxy)acetate (0.1 g, 0.213 mmol), (8-fluoro-5-methylchroman-6-yl)boronic acid (0.049 g, 0.234 mmol) and 2M Na$_2$CO$_3$ (0.160 ml, 0.319 mmol) in DMF (2 mL) was degassed for 10 min. Then, Pd(Ph$_3$P)$_4$ (0.025 g, 0.021 mmol) was added, degassed for 5 min and heated at 110° C. for 7 h. Then, cooled and purified pre-HPLC to afford two compounds.

Compound 1: (2S)-ethyl 2-(4,5-bis(8-fluoro-5-methylchroman-6-yl)-2,6-dimethylpyridin-3-yl)-2-(tert-butoxy)acetate (0.0553 g, 0.093 mmol, 43.8% yield), off-white solid. LCMS (M+H)=594.4.

Compound 2: (2S)-ethyl 2-(5-bromo-4-(8-fluoro-5-methylchroman-6-yl)-2,6-dimethylpyridin-3-yl)-2-(tert-butoxy)acetate (0.023 g, 0.025 mmol, 11.70% yield), colorless paste. LCMS (M+H)=510.2.

Example 1

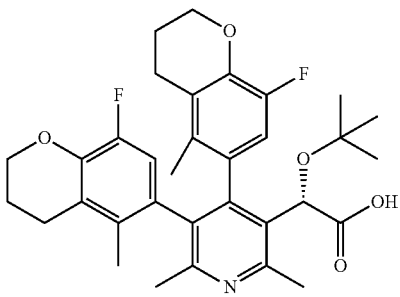 [SMILES: Cc1nc(C)c([C@H](OC(C)(C)C)C(=O)O)c(-c2cc(F)c3c(c2C)CCCO3)c1-c1cc(F)c2c(c1C)CCCO2]

(2S)-2-(4,5-Bis(8-fluoro-5-methylchroman-6-yl)-2,6-dimethylpyridin-3-yl)-2-(tert-butoxy)acetic Acid A mixture of (2S)-ethyl 2-(4,5-bis(8-fluoro-5-methylchroman-6-yl)-2,6-dimethylpyridin-3-yl)-2-(tert-butoxy)acetate (0.055 g, 0.093 mmol) and LiOH (0.022 g, 0.926 mmol) in 9:1 EtOH/H$_2$O (2 mL) was refluxed for 4 h. Then, cooled and purified by prep-HPLC to afford (2S)-2-(4,5-bis(8-fluoro-5-methylchroman-6-yl)-2,6-dimethylpyridin-3-yl)-2-(tert-butoxy)acetic acid (0.0449 g, 0.079 mmol, 86% yield) as white solid and 1.4:1.6 mixture of atroisomers. LCMS (M+H)=566.3.

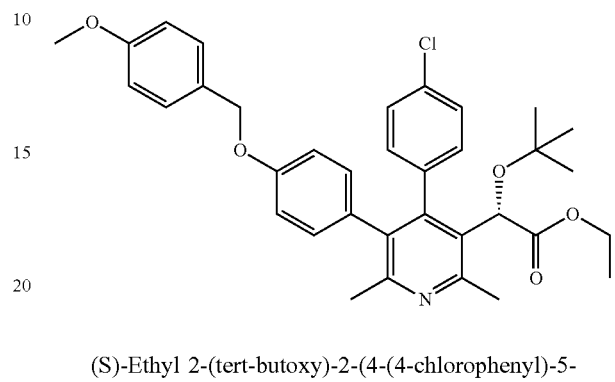

(S)-Ethyl 2-(tert-butoxy)-2-(4-(4-chlorophenyl)-5-(4-((4-methoxybenzyl)oxy)phenyl)-2,6-dimethyl-pyridin-3-yl)acetate A mixture of (S)-ethyl 2-(5-bromo-4-iodo-2,6-dimethyl-pyridin-3-yl)-2-(tert-butoxy)acetate (0.087 g, 0.185 mmol), (4-chlorophenyl)boronic acid (0.029 g, 0.185 mmol) and 2M Na$_2$CO$_3$ (0.093 ml, 0.185 mmol) in DMF (2 mL) was degassed for 10 min. Then, Pd(Ph$_3$P)$_4$ (0.021 g, 0.019 mmol) was added, degassed for 5 min and placed in pre-heated oil bath at 60° C. After 6 h, (4-((4-methoxybenzyl)oxy)phenyl) boronic acid (0.057 g, 0.222 mmol) was added and heated at 110° C. for 2 h. Then, cooled and purified by prep-HPLC to affordpale yellow paste which is a mixture of compounds (0.08 g) and used in the next step without further purification.

Example 2

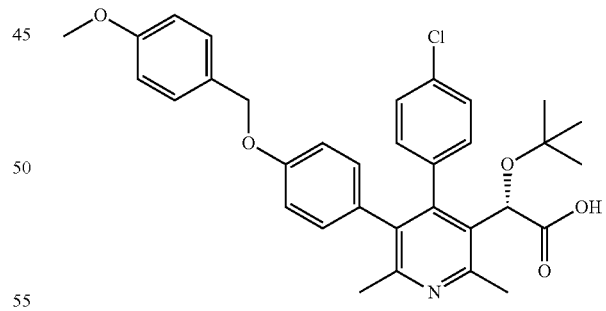

(S)-2-(tert-Butoxy)-2-(4-(4-chlorophenyl)-5-(4-((4-methoxybenzyl)oxy)phenyl)-2,6-dimethylpyridin-3-yl)acetic Acid A mixture of (S)-ethyl 2-(tert-butoxy)-2-(4-(4-chlorophenyl)-5-(4-(4-methoxybenzyl)oxy)phenyl)-2,6-dimethylpyridin-3-yl)acetate (0.08 g, 0.136 mmol) and LiOH (0.033 g, 1.360 mmol) in 9:1 EtOH/H$_2$O (3 mL) was refluxed for 4 h. Then, cooled and purified by prep-HPLC to afford (S)-2-(tert-butoxy)-2-(4-(4-chlorophenyl)-5-(4-((4-methoxybenzyl)oxy)phenyl)-2,6-dimethylpyridin-3-yl)acetic acid (0.0068 g, 0.012 mmol, 8.93% yield) as white solid. ¹H NMR (500 MHz, CDCl₃) δ 7.54 (br. s., 1H), 7.35 (d, J=8.5 Hz, 2H), 7.31 (d, J=7.9 Hz, 1H), 7.05-7.12 (m, 2H), 6.94 (d, J=8.5 Hz, 2H), 6.91 (d, J=8.4 Hz, 1H), 6.71 (t, J=8.5 Hz, 2H), 6.58 (d, J=7.4 Hz, 1H), 5.07 (br. s., 1H), 4.94 (s, 2H), 3.85 (s, 3H), 2.71 (br. s., 3H), 2.37 (s, 3H), 1.01 (s, 9H). LCMS (M+H)=560.3.

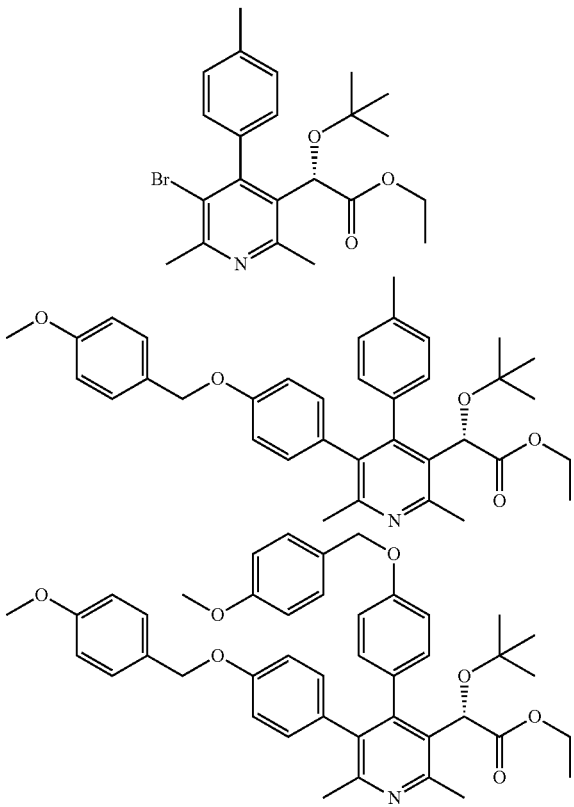

A mixture of (S)-ethyl 2-(5-bromo-4-iodo-2,6-dimethylpyridin-3-yl)-2-(tert-butoxy)acetate (0.078 g, 0.166 mmol), p-tolylboronic acid (0.023 g, 0.166 mmol) and 2M Na₂CO₃ (0.249 ml, 0.498 mmol) in DMF (3 mL) was degassed for 10 min. Then, PdCl₂(dppf)-CH₂Cl₂Adduct (0.014 g, 0.017 mmol) was added, degassed for 5 min and placed in a pre-heated oil bath 60° C. After 6 h, (4-((4-methoxybenzyl)oxy)phenyl)boronic acid (0.064 g, 0.249 mmol) was added and stirred at 90° C. for 4 h. Then, cooled and purified by prep-HPLC to afford three products.

(S)-Ethyl 2-(5-bromo-2,6-dimethyl-4-(p-tolyl)pyridin-3-yl)-2-(tert-butoxy)acetate ¹H NMR (500 MHz, CDCl₃) δ 7.30-7.26 (m, 2H), 7.21-7.17 (m, 1H), 7.15-7.11 (m, 1H), 4.91 (s, 1H), 4.22-4.13 (m, 2H), 2.71 (s, 3H), 2.61 (s, 3H), 2.46 (s, 3H), 1.26 (t, J=7.1 Hz, 3H), 0.99 (s, 9H). LCMS (M+H)=690.4.

(S)-Ethyl 2-(tert-butoxy)-2-(5-(4-((4-methoxybenzyl)oxy)phenyl)-2,6-dimethyl-4-(p-tolyl)pyridin-3-yl)acetate ¹H NMR (500 MHz, CDCl₃) δ 7.42 (d, J=8.5 Hz, 2H), 7.36-7.31 (m, 1H), 7.27-7.22 (m, 1H), 7.20-7.15 (m, 1H), 7.08 (d, J=8.8 Hz, 3H), 6.96 (d, J=8.7 Hz, 2H), 6.94-6.85 (m, 1H), 6.73-6.62 (m, 1H), 5.08 (s, 2H), 4.95 (s, 1H), 4.23-4.14 (m, 2H), 3.85 (s, 3H), 2.72 (s, 3H), 2.61 (s, 3H), 1.26 (t, J=7.1 Hz, 3H), 0.99 (s, 9H). LCMS (M+H)=568.4.

(S)-Ethyl 2-(4,5-bis(4-((4-methoxybenzyl)oxy)phenyl)-2,6-dimethylpyridin-3-yl)-2-(tert-butoxy)acetate ¹H NMR (500 MHz, CDCl₃) δ 7.38-7.33 (m, 4H), 7.25 (dd, J=8.4, 2.0 Hz, 1H), 7.09 (d, J=6.9 Hz, 1H), 6.95-6.91 (m, 4H), 6.89 (dd, J=8.5, 2.4 Hz, 2H), 6.73-6.67 (m, 3H), 6.66-6.61 (m, 1H), 5.04 (s, 1H), 4.96 (s, 2H), 4.94 (s, 2H), 4.30-4.17 (m, 2H), 3.83 (s, 3H), 3.83 (s, 3H), 2.70 (s, 3H), 2.35 (s, 3H), 1.30 (t, J=7.2 Hz, 3H), 0.97 (s, 9H). LCMS (M+H)=690.4.

Example 3

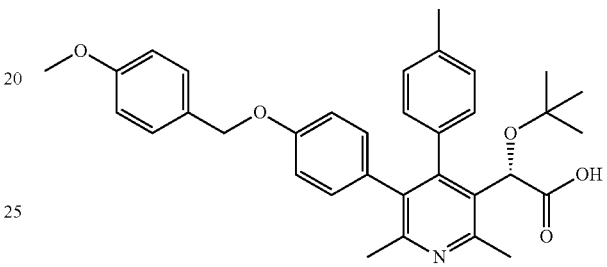

(S)-2-(tert-Butoxy)-2-(5-(4-((4-methoxybenzyl)oxy)phenyl)-2,6-dimethyl-4-(p-tolyl)pyridin-3-yl)acetic Acid A mixture of (S)-ethyl 2-(tert-butoxy)-2-(5-(4-((4-methoxybenzyl)oxy)phenyl)-2,6-dimethyl-4-(p-tolyl)pyridin-3-yl)acetate (0.034 g, 0.060 mmol) and LiOH (0.014 g, 0.599 mmol) in 9:1 EtOH/H₂O (2 mL0 was refluxed for h. Then, cooled and purified by prep-HPLC to afford (S)-2-(tert-butoxy)-2-(5-(4-((4-methoxybenzyl)oxy)phenyl)-2,6-dimethyl-4-(p-tolyl)pyridin-3-yl)acetic acid (0.0051 g, 9.45 μmol, 15.78% yield). ¹H NMR (500 MHz, CDCl₃) δ 7.47-7.41 (m, 1H), 7.35 (d, J=8.7 Hz, 2H), 7.13 (d, J=7.3 Hz, 2H), 6.96-6.85 (m, 4H), 6.71-6.63 (m, 2H), 6.60 (d, J=7.7 Hz, 1H), 5.18 (s, 1H), 4.93 (s, 2H), 3.85 (s, 3H), 2.68 (s, 3H), 2.37 (s, 3H), 2.29 (s, 3H), 0.99 (s, 9H). LCMS (M+H)=540.3.

Example 4

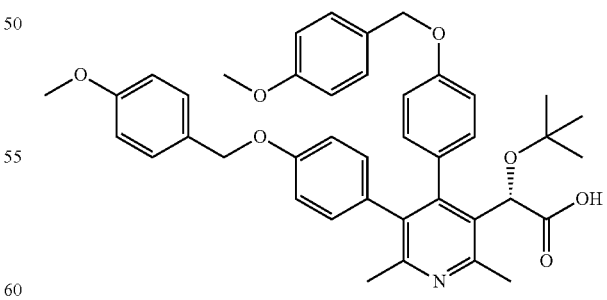

(S)-2-(4,5-Bis(4-((4-methoxybenzyl)oxy)phenyl)-2,6-dimethylpyridin-3-yl)-2-(tert-butoxy)acetic Acid A mixture of (S)-ethyl 2-(4,5-bis(4-((4-methoxybenzyl)oxy)phenyl)-2,6-dimethylpyridin-3-yl)-2-(tert-butoxy)acetate (0.0095 g, 0.014 mmol) and LiOH (3.30 mg, 0.138 mmol) in 9:1 EtOH/H$_2$O (1 mL) was refluxed for h. Then, cooled and purified by prep-HPLC to afford (S)-2-(4,5-bis (4-((4-methoxybenzyl)oxy)phenyl)-2,6-dimethylpyridin-3-yl)-2-(tert-butoxy)acetic acid (0.0082 g, 0.012 mmol, 90% yield) as white solid. $^1$H NMR (500 MHz, CDCl$_3$) δ 7.59-7.47 (m, 1H), 7.35 (dd, J=8.0, 5.9 Hz, 4H), 7.13 (d, J=7.1 Hz, 1H), 6.96-6.88 (m, 6H), 6.73-6.65 (m, 3H), 6.60 (d, J=6.9 Hz, 1H), 5.19 (br. s., 1H), 4.95 (br. s., 2H), 4.94 (s, 2H), 3.83 (s, 3H), 3.82 (s, 3H), 2.72 (br. s., 3H), 2.38 (s, 3H), 0.98 (s, 9H). LCMS (M+H)=662.4.

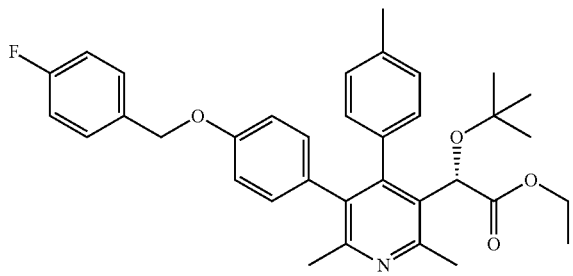 [SMILES: CCOC(=O)[C@@H](OC(C)(C)C)c1c(C)nc(C)c(-c2ccc(OCc3ccc(F)cc3)cc2)c1-c1ccc(C)cc1]

(S)-Ethyl 2-(tert-butoxy)-2-(5-(4-((4-fluorobenzyl)oxy)phenyl)-2,6-dimethyl-4-(p-tolyl)pyridin-3-yl)acetate A mixture of (S)-ethyl 2-(5-bromo-2,6-dimethyl-4-(p-tolyl)pyridin-3-yl)-2-(tert-butoxy)acetate (0.03 g, 0.069 mmol), (4-((4-fluorobenzyl)oxy)phenyl)boronic acid (0.034 g, 0.138 mmol) and 2M Na$_2$CO$_3$ (0.069 ml, 0.138 mmol) in DMF (2 mL) degassed for 10 min. Then, Pd(Ph$_3$P)$_4$ (7.98 mg, 6.91 µmol) was added, degassed for 5 min and placed in a pre-heated oil bath at 110° C. After 8 h, cooled and purified by prep-HPLC to afford (S)-ethyl 2-(tert-butoxy)-2-(5-(4-((4-fluorobenzyl)oxy)phenyl)-2,6-dimethyl-4-(p-tolyl)pyridin-3-yl)acetate (0.10113 g, 0.182 mmol, 264% yield) as purple solid. $^1$H NMR (500 MHz, CDCl$_3$) δ 7.41-7.36 (m, 2H), 7.20 (dd, J=7.7, 1.7 Hz, 1H), 7.11-7.06 (m, 4H), 6.90-6.84 (m, 2H), 6.71-6.63 (m, 3H), 5.00 (s, 1H), 4.97 (s, 2H), 4.30-4.15 (m, 2H), 2.70 (s, 3H), 2.34 (s, 3H), 2.29 (s, 3H), 1.30 (t, J=7.2 Hz, 3H), 0.96 (s, 9H). LCMS (M+H)=556.4.

Example 5

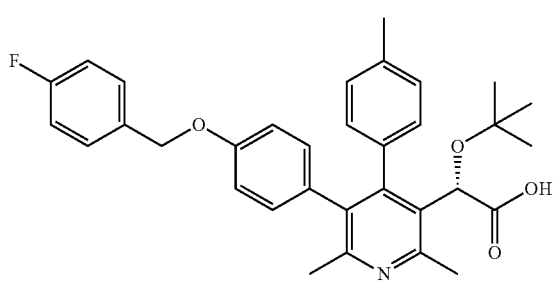 [SMILES: Cc1ccc(-c2c(-c3ccc(OCc4ccc(F)cc4)cc3)c(C)nc(C)c2[C@H](OC(C)(C)C)C(=O)O)cc1]

(S)-2-(tert-Butoxy)-2-(5-(4-((4-fluorobenzyl)oxy)phenyl)-2,6-dimethyl-4-(p-tolyl)pyridin-3-yl)acetic Acid A mixture of (S)-ethyl 2-(tert-butoxy)-2-(5-(4-((4-fluorobenzyl)oxy)phenyl)-2,6-dimethyl-4-(p-tolyl)pyridin-3-yl) acetate (0.011 g, 0.020 mmol) and LiOH (4.74 mg, 0.198 mmol) in 9:1 EtOH/H$_2$O (1 mL) was refluxed for 4 h. Then, cooled and purified by prep-HPLC to afford (S)-2-(tert-butoxy)-2-(5-(4-((4-fluorobenzyl)oxy)phenyl)-2,6-dimethyl-4-(p-tolyl)pyridin-3-yl)acetic acid (0.007 g, 0.013 mmol, 67.0% yield) as white solid. $^1$H NMR (500 MHz, CDCl$_3$) δ 7.52-7.43 (m, 1H), 7.43-7.36 (m, 2H), 7.16-7.05 (m, 4H), 6.90 (d, J=7.1 Hz, 1H), 6.86 (d, J=7.7 Hz, 1H), 6.69-6.57 (m, 3H), 5.16 (s, 1H), 4.97 (s, 2H), 2.71 (br. s., 3H), 2.37 (s, 3H), 2.29 (s, 3H), 0.98 (s, 9H). LCMS (M+H)=528.3.

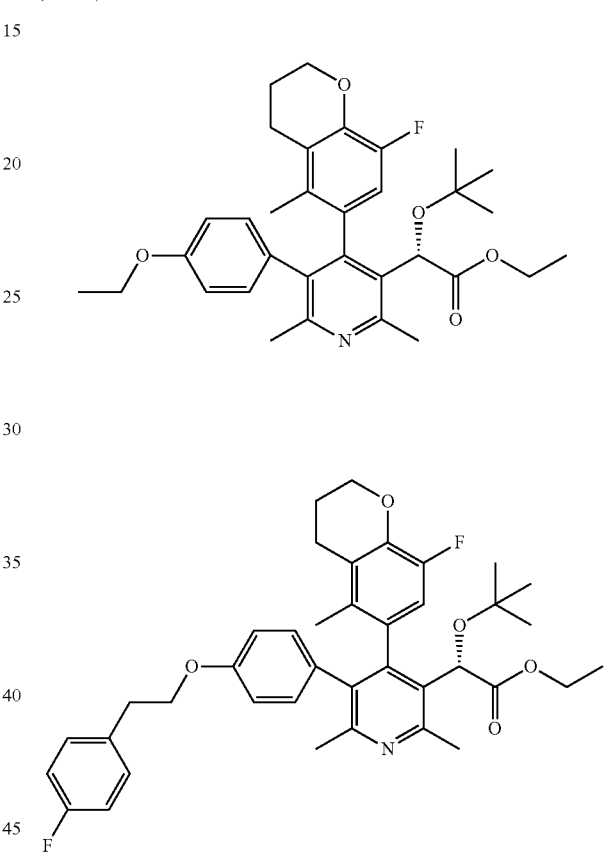

To a stirred solution of (2S)-ethyl 2-(tert-butoxy)-2-(4-(8-fluoro-5-methylchroman-6-yl)-5-(4-hydroxyphenyl)-2,6-dimethylpyridin-3-yl)acetate (0.04 g, 0.077 mmol), 2-(4-fluorophenyl)ethanol (0.054 g, 0.383 mmol) and Ph$_3$P (0.060 g, 0.230 mmol) in THF (3 mL) was added DEAD (0.036 ml, 0.230 mmol) at 0° C. After 22 h at rt, the reaction mixture was concentrated and the residue was purified by prep-HPLC to afford (2S)-ethyl 2-(tert-butoxy)-2-(5-(4-ethoxyphenyl)-4-(8-fluoro-5-methylchroman-6-yl)-2,6-dimethylpyridin-3-yl)acetate (0.0071 g, 0.013 mmol, 16.84% yield); LCMS (M+H)=550.4 and (2S)-ethyl 2-(tert-butoxy)-2-(4-(8-fluoro-5-methylchroman-6-yl)-5-(4-(4-fluorophenethoxy)phenyl)-2,6-dimethylpyridin-3-yl)acetate (0.012 g, 0.019 mmol, 24.31% yield), light brown solid; LCMS (M+H)=644.4.

Example 6

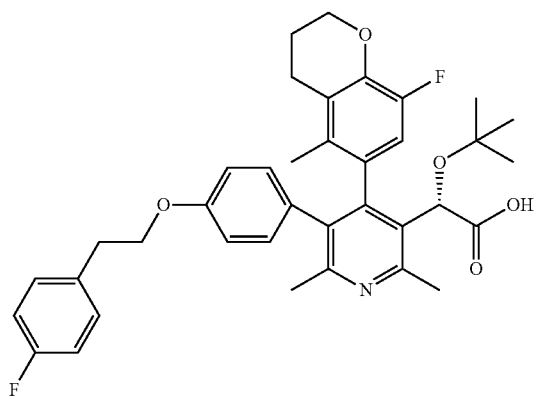 [SMILES: Cc1nc(C)c([C@H](OC(C)(C)C)C(=O)O)c(-c2cc(F)c3c(c2C)CCCO3)c1-c1ccc(OCCc2ccc(F)cc2)cc1]

(2S)-2-(tert-Butoxy)-2-(4-(8-fluoro-5-methylchroman-6-yl)-5-(4-(4-fluorophenethoxy)phenyl)-2,6-dimethylpyridin-3-yl)acetic Acid A mixture of (2S)-ethyl 2-(tert-butoxy)-2-(4-(8-fluoro-5-methylchroman-6-yl)-5-(4-(4-fluorophenethoxy)phenyl)-2,6-dimethylpyridin-3-yl)acetate (0.012 g, 0.019 mmol) and LiOH (4.46 mg, 0.186 mmol) in 9:1 EtOH/H$_2$O (1 mL) was refluxed for 3.5 h. Then, cooled and purified by prep-HPLC to afford (2S)-2-(tert-butoxy)-2-(4-(8-fluoro-5-methylchroman-6-yl)-5-(4-(4-fluorophenethoxy)phenyl)-2,6-dimethylpyridin-3-yl)acetic acid (0.0096 g, 0.016 mmol, 84% yield) as solid. $^1$H NMR (500 MHz, CDCl$_3$) δ 7.27-7.22 (m, 2H), 7.05-6.99 (m, 2H), 6.84-6.90 (m, 1H), 6.77-6.82 (m, 1H), 6.70 (d, J=8.4 Hz, 2H), 6.57 (d, J=11.2 Hz, 1H), 4.97 (br. s., 1H), 4.20-4.13 (m, 2H), 4.10 (t, J=6.9 Hz, 2H), 3.05 (t, J=6.9 Hz, 2H), 2.74 (s, 3H), 2.59-2.49 (m, 1H), 2.46-2.36 (m, 1H), 2.28 (s, 3H), 2.05-1.93 (m, 2H), 1.81 (s, 3H), 1.14 (s, 9H). LCMS (M+H)=616.3.

Example 7

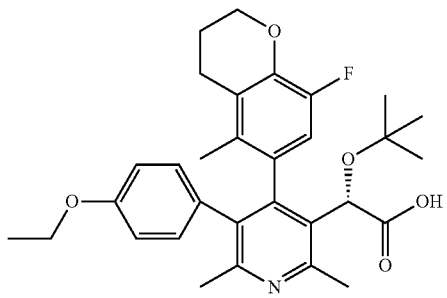 [SMILES: CCOc1ccc(-c2c(C)nc(C)c([C@H](OC(C)(C)C)C(=O)O)c2-c2cc(F)c3c(c2C)CCCO3)cc1]

(2S)-2-(tert-Butoxy)-2-(5-(4-ethoxyphenyl)-4-(8-fluoro-5-methylchroman-6-yl)-2,6-dimethylpyridin-3-yl)acetic Acid A mixture of (2S)-ethyl 2-(tert-butoxy)-2-(5-(4-ethoxyphenyl)-4-(8-fluoro-5-methylchroman-6-yl)-2,6-dimethylpyridin-3-yl)acetate (0.007 g, 0.013 mmol) and LiOH (3.05 mg, 0.127 mmol) in 9:1 EtOH/H$_2$O (1 mL) was refluxed for 4.5 h. Then, cooled and purified by prep-HPLC to afford (2S)-2-(tert-butoxy)-2-(5-(4-ethoxyphenyl)-4-(8-fluoro-5-methylchroman-6-yl)-2,6-dimethylpyridin-3-yl)acetic acid (0.0061 g, 0.012 mmol, 92% yield) as solid. $^1$H NMR (500 MHz, CDCl$_3$) δ 6.87 (d, J=6.6 Hz, 1H), 6.81 (d, J=7.4 Hz, 1H), 6.71 (d, J=8.2 Hz, 2H), 6.58 (d, J=11.2 Hz, 1H), 5.03 (br. s., 1H), 4.21-4.13 (m, 2H), 3.99 (q, J=6.9 Hz, 2H), 2.72 (s, 3H), 2.60-2.52 (m, 1H), 2.47-2.39 (m, 1H), 2.31 (s, 3H), 2.06-1.95 (m, 2H), 1.82 (s, 3H), 1.41 (t, J=7.0 Hz, 3H), 1.16 (s, 9H). LCMS (M+)=522.3.

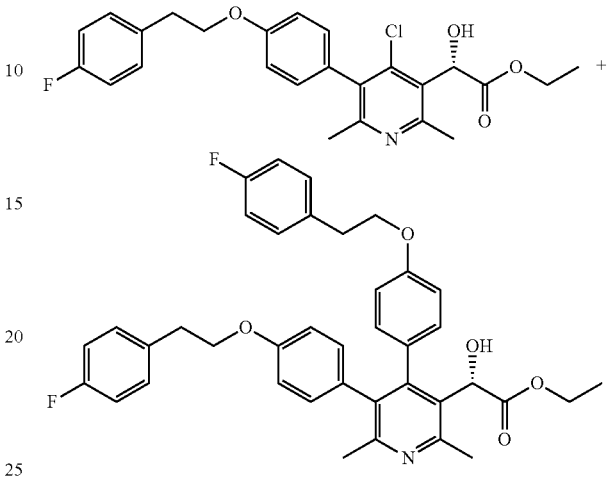

A mixture (S)-ethyl 2-(5-bromo-4-chloro-2,6-dimethylpyridin-3-yl)-2-hydroxyacetate (1.445 g, 4.48 mmol), (4-(4-fluorophenethoxy)phenyl)boronic acid (1.747 g, 6.72 mmol) and 2M Na2CO3 (4.48 ml, 8.96 mmol) in DMF (20 mL) was degassed for 10 min by spurging with N2. Then, Pd(Ph3P)4 (0.259 g, 0.224 mmol) was added, degassed for 5 min and placed in an oil bath pre-heated to 80° C. After 9 h at 100° C., cooled, diluted with ether (100 mL), washed with water (5×25 mL), dried (MgSO4), filtered, concentrated and purified by flash chromatography using 30, 50, 60 and 70% EtOAc/Hex to afford two products.

Product 1: (S)-ethyl 2-(4-chloro-5-(4-(4-fluorophenethoxy)phenyl)-2,6-dimethylpyridin-3-yl)-2-hydroxyacetate (1.197, 2.61 mmol, 58.4% yield) as viscous and contaminated with (S)-ethyl 2-(4,5-bis(4-(4-fluorophenethoxy)phenyl)-2,6-dimethylpyridin-3-yl)-2-hydroxyacetate came out with 50-60% EtOAc/Hex.

Product 2: (S)-ethyl 2-(4,5-bis(4-(4-fluorophenethoxy)phenyl)-2,6-dimethylpyridin-3-yl)-2-hydroxyacetate (0.558 g, 0.875 mmol, 19.53% yield) as' came out with 60-70% EtOAc/Hex. Off-white solid.

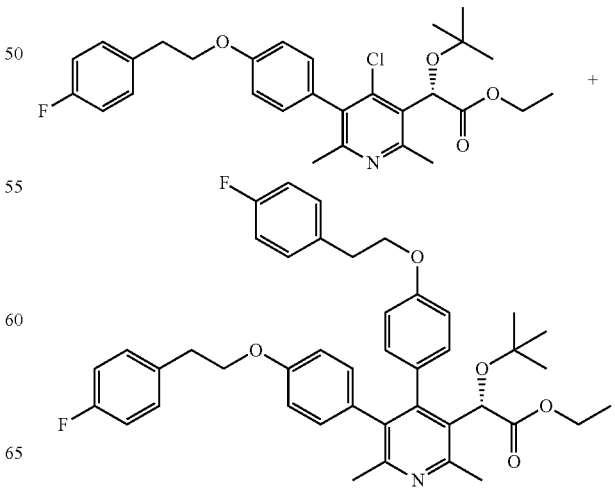

A stirred ice-cold mixture of (S)-ethyl 2-(4-chloro-5-(4-(4-fluorophenethoxy)phenyl)-2,6-dimethylpyridin-3-yl)-2-hydroxyacetate (0.83 g, 1.813 mmol) contaminated with ~10% of (S)-ethyl 2-(4,5-bis(4-(4-fluorophenethoxy)phenyl)-2,6-dimethylpyridin-3-yl)-2-hydroxyacetate (1.156 g, 1.813 mmol) and 70% HClO$_4$ (0.218 ml, 2.54 mmol) in CH$_2$Cl$_2$ (20 mL) was saturated with isobutylene by bubbling through the reaction mixture for 10 min. Then, cold bath was removed and stirred at rt for 41 h. LCMS at this point showed completion of reaction. The reaction mixture was stirred with sat Na$_2$CO$_3$ (10 mL), org layer separated, dried (MgSO$_4$), filtered, concentrated and purified by flash chromatography using 500 mL each 10, 15, 20, 25, 30 and 40% EtOAc/Hex to provide two products.

Product 1: (S)-Ethyl 2-(tert-butoxy)-2-(4-chloro-5-(4-(4-fluorophenethoxy)phenyl)-2,6-dimethylpyridin-3-yl)acetate (0.71 g, 1.381 mmol, 76% yield); came out with 20-25% EtOAc/Hex. Viscous pale yellow oil. $^1$H NMR (500 MHz, CDCl$_3$) δ 7.32-7.29 (m, 2H), 7.16-7.13 (m, 1H), 7.11-7.08 (m, 1H), 7.06-7.02 (m, 2H), 7.01-6.97 (m, 2H), 5.78 (s, 1H), 4.25-4.17 (m, 4H), 3.13 (t, J=6.9 Hz, 2H), 2.66 (s, 3H), 2.29 (s, 3H), 1.25 (s, 9H), 1.24 (t, J=7.1 Hz, 3H).

Product 2: (S)-Ethyl 2-(4,5-bis(4-(4-fluorophenethoxy)phenyl)-2,6-dimethylpyridin-3-yl)-2-(tert-butoxy)acetate (0.091 g, 0.131 mmol, 7.24% yield), came out with 30 and 40% EtOAc/Hex. Pale yellow paste. $^1$H NMR (500 MHz, CDCl$_3$) δ 7.24-7.21 (m, 5H), 7.08-7.05 (m, 1H), 7.04-6.99 (m, 4H), 6.79 (dd, J=8.4, 2.6 Hz, 2H), 6.70 (dd, J=8.4, 2.1 Hz, 1H), 6.62-6.59 (m, 3H), 5.01 (s, 1H), 4.28-4.17 (m, 2H), 4.111-4.08 (m, 4H), 3.04 (t, J=6.7 Hz, 4H), 2.68 (s, 3H), 2.32 (s, 3H), 1.28 (t, J=7.1 Hz, 3H), 0.96 (s, 9H).

Example 8

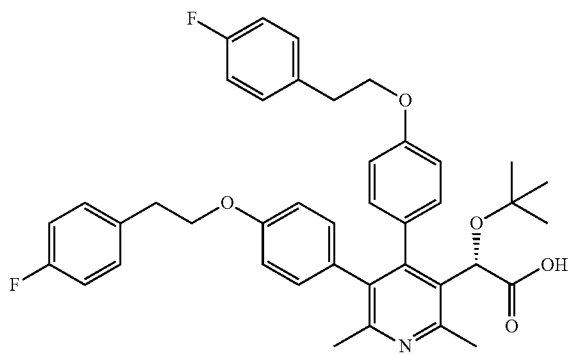 [SMILES: Cc1nc(C)c([C@H](OC(C)(C)C)C(=O)O)c(-c2ccc(OCCc3ccc(F)cc3)cc2)c1-c1ccc(OCCc2ccc(F)cc2)cc1]

(S)-2-(4,5-Bis(4-(4-fluorophenethoxy)phenyl)-2,6-dimethylpyridin-3-yl)-2-(tert-butoxy)acetic Acid A solution of (S)-ethyl 2-(4,5-bis(4-(4-fluorophenethoxy)phenyl)-2,6-dimethylpyridin-3-yl)-2-(tert-butoxy)acetate (0.081 g, 0.117 mmol) and 1M NaOH (0.584 ml, 0.584 mmol) in EtOH (2 mL) was refluxed for 3 h. Then, cooled and purified by prep-HPLC to afford (S)-2-(4,5-bis(4-(4-fluorophenethoxy)phenyl)-2,6-dimethylpyridin-3-yl)-2-(tert-butoxy)acetic acid (0.0631 g, 0.095 mmol, 81% yield) as white solid. $^1$H NMR (500 MHz, CDCl$_3$) δ 7.49 (br. s., 1H), 7.25-7.18 (m, 4H), 7.11 (d, J=7.6 Hz, 1H), 7.04-6.97 (m, 2H), 6.82 (d, J=8.2 Hz, 2H), 6.65 (dd, J=8.5, 2.0 Hz, 1H), 6.61-6.52 (m, 3H), 5.17 (s, 1H), 4.08 (td, J=6.9, 3.2 Hz, 4H), 3.03 (q, J=6.6 Hz, 4H), 2.68 (s, 3H), 2.34 (s, 3H), 0.97 (s, 9H). LCMS (M+H)=666.2.

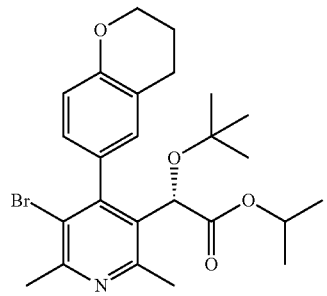 [SMILES: Cc1nc(C)c([C@H](OC(C)(C)C)C(=O)OC(C)C)c(-c2ccc3c(c2)CCCO3)c1Br]

(S)-Isopropyl 2-(5-bromo-4-(chroman-6-yl)-2,6-dimethylpyridin-3-yl)-2-(tert-butoxy)acetate A mixture of (S)-isopropyl 2-(5-bromo-4-iodo-2,6-dimethylpyridin-3-yl)-2-(tert-butoxy)acetate (5 g, 10.33 mmol), 2-(isochroman-6-yl)-4,4,5,5-tetramethyl-1,3,2-dioxaborolane (3.1 g, 11.92 mmol) and 2M Na$_2$CO$_3$ (15.49 mL, 31.0 mmol) in dioxane (50 mL) was degassed for 10 min. Then, PdCl$_2$(dppf)-CH$_2$Cl$_2$ adduct (0.4 g, 0.490 mmol) was added, degassed for 5 min and placed in a pre-heated oil bath 55° C. for 20 h. Then, the reaction mixture was cooled and diluted with EtOAc, washed with water, brine, dried (MgSO$_4$) concentrated and purified by ISCO 220 g column (EtOAc/Hex: 0 to 20%) to afford (S)-isopropyl 2-(5-bromo-4-(chroman-6-yl)-2,6-dimethylpyridin-3-yl)-2-(tert-butoxy)acetate (3.1 g, 6.32 mmol, 61.2% yield). $^1$H NMR (500 MHz, CDCl$_3$) δ 7.07-6.76 (m, 3H), 5.11-4.99 (m, 1H), 4.95-4.79 (m, 1H), 4.32-4.22 (m, 2H), 2.91-2.74 (m, 2H), 2.69 (s, 3H), 2.58 (s, 3H), 2.13-2.03 (m, 2H), 1.31-1.22 (m, 3H), 1.21-1.12 (m, 3H), 0.98 (s, 9H). LCMS (M+H)=492.2.

Example 9

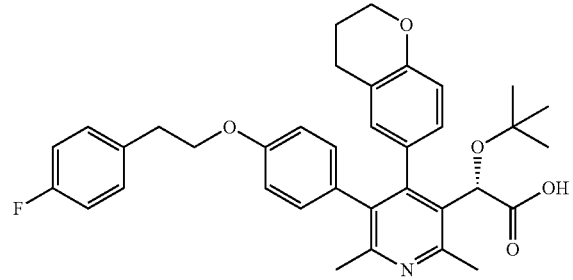 [SMILES: Cc1nc(C)c([C@H](OC(C)(C)C)C(=O)O)c(-c2ccc3c(c2)CCCO3)c1-c1ccc(OCCc2ccc(F)cc2)cc1]

(S)-2-(tert-Butoxy)-2-(4-(chroman-6-yl)-5-(4-(4-fluorophenethoxy)phenyl)-2,6-dimethylpyridin-3-yl) acetic Acid A mixture of (S)-isopropyl 2-(5-bromo-4-(chroman-6-yl)-2,6-dimethylpyridin-3-yl)-2-(tert-butoxy)acetate (0.06 g, 0.122 mmol), 2-(4-((4-fluorophenethoxy)phenyl)-6-methyl-1,3,2-dioxaborocane-4,8-dione (0.07 g, 0.189 mmol), 2-dicyclohexylphosphino-2',6'-dimethoxybiphenyl (0.012 g, 0.029 mmol), Water (0.6 mL) and 2M K$_3$PO$_4$ (0.06 mL, 0.120 mmol) in 1,4-dioxane (2 mL) was degassed for 10 min. Then, Pd(OAc)$_2$ (0.003 g, 0.013 mmol) was added, degassed for 5 min, refilled N2. The mixture was heated at 80° C. for 16 h. Then, the reaction mixture was cooled and extracted with EtOAc. The organic solution was washed with water and concentrated. The residue was treated with 1 ml EtOH (1 ml) and NaOH (0.1 g, 2.500 mmol) at 85° C. for 4 h. The reaction mixture was cooled, added 1 drop of AcOH, filtered off the solid, purified by prep HPLC to afford (S)-2-(tert-butoxy)-2-(4-(chroman-6-yl)-5-(4-(4-fluorophenethoxy)phenyl)-2,6-dimethylpyridin-3-yl)acetic acid (0.0659 g, 0.113 mmol, 92% yield). LCMS (M+H)=584.27.

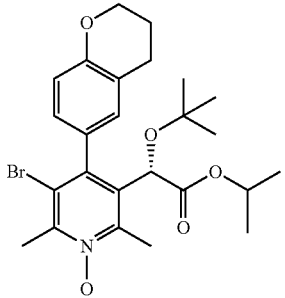

(S)-3-Bromo-5-(1-(tert-butoxy)-2-isopropoxy-2-oxoethyl)-4-(chroman-6-yl)-2,6-dimethylpyridine 1-oxide To a stirred solution of (S)-isopropyl 2-(5-bromo-4-(chroman-6-yl)-2,6-dimethylpyridin-3-yl)-2-(tert-butoxy)acetate (1.05 g, 2.141 mmol) in DCM (20 mL) was added mCPBA (0.720 g, 3.21 mmol) at rt. After 2 h, the reaction mixture was washed with satd. Na$_2$CO$_3$ (3×10 mL), dried (MgSO$_4$), filtered and concentrated to give (S)-3-bromo-5-(1-(tert-butoxy)-2-isopropoxy-2-oxoethyl)-4-(chroman-6-yl)-2,6-dimethylpyridine 1-oxide (1.08 g, 100% yield) as pale yellow foam which was used in the next step without purification. LCMS (M+H)=508.1.

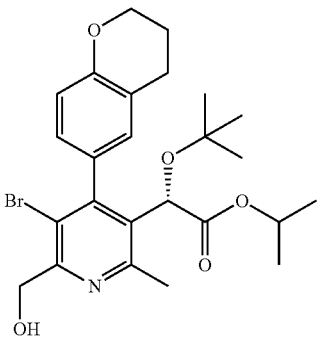

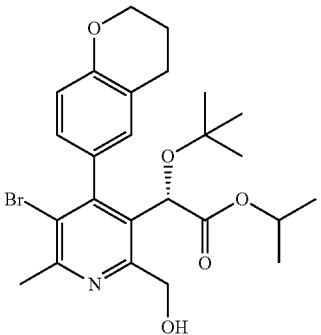

(S)-Isopropyl 2-(5-bromo-4-(chroman-6-yl)-6-(hydroxymethyl)-2-methylpyridin-3-yl)-2-(tert-butoxy) acetate and (S)-isopropyl 2-(5-bromo-4-(chroman-6-yl)-2-(hydroxymethyl)-6-methylpyridin-3-yl)-2-(tert-butoxy)acetate To a stirred solution of (S)-3-bromo-5-(1-(tert-butoxy)-2-isopropoxy-2-oxoethyl)-4-(chroman-6-yl)-2,6-dimethylpyridine 1-oxide (1.1 g, 2.172 mmol) in anhydrous CH$_2$Cl$_2$ (20 mL) was added dropwise trifluoroacetic anhydride (0.614 mL, 4.34 mmol) over 15 min at rt. After 2 h, satd. NaHCO$_3$ (50 mL) was slowly added, stirred for 10 min, aqueous layer was separated. The organic layer was washed with 1N NaOH, dried (MgSO$_4$), filtered, concentrated and purified by flash chromatography to afford two products.

Compound 1: (S)-Isopropyl 2-(5-bromo-4-(chroman-6-yl)-6-(hydroxymethyl)-2-methylpyridin-3-yl)-2-(tert-butoxy)acetate (0.59 g, 1.165 mmol, 53.6% yield), white solid. $^1$H NMR (500 MHz, CDCl3) Shift 7.05-6.99 (m, 1H), 6.97-6.93 (m, 1H), 6.90 (s, 1H), 5.13-4.95 (m, J=15.1 Hz, 2H), 4.73 (s, 3H), 4.33-4.26 (m, 2H), 2.94-2.71 (m, 2H), 2.66 (s, 3H), 2.13-2.07 (m, 2H), 1.29 (d, J=6.3 Hz, 3H), 1.27-1.25 (m, 3H), 1.00 (s, 9H).

Compound 2: (S)-Isopropyl 2-(5-bromo-4-(chroman-6-yl)-2-(hydroxymethyl)-6-methylpyridin-3-yl)-2-(tert-butoxy)acetate (0.12 g, 0.237 mmol, 10.91% yield), colorless viscous oil; $^1$H NMR (500 MHz, CDCl3) Shift 7.06-6.84 (m, 3H), 5.13-5.00 (m, 2H), 4.96 (s, 2H), 4.34-4.28 (m, J=4.9 Hz, 2H), 2.93-2.84 (m, 2H), 2.82 (s, 3H), 2.15-2.07 (m, 2H), 1.29 (dd, J=12.1, 5.9 Hz, 6H), 1.02-0.97 (m, 9H).

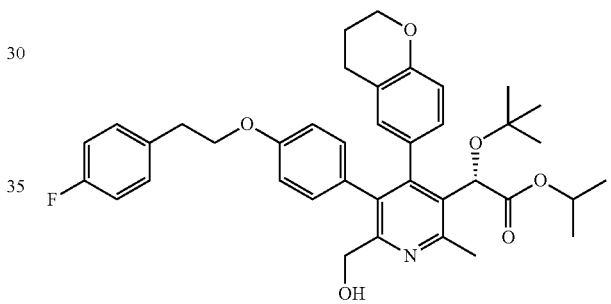

(S)-Isopropyl 2-(tert-butoxy)-2-(4-(chroman-6-yl)-5-(4-(4-fluorophenethoxy)phenyl)-6-(hydroxymethyl)-2-methylpyridin-3-yl)acetate A mixture of (S)-isopropyl 2-(5-bromo-4-(chroman-6-yl)-6-(hydroxymethyl)-2-methylpyridin-3-yl)-2-(tert-butoxy) acetate (0.31 g, 0.612 mmol), 2-(4-(4-fluorophenethoxy)phenyl)-6-methyl-1,3,6,2-dioxazaborocane-4,8-dione (0.26 g, 0.700 mmol), 2-dicyclohexylphosphino-2',6'-dimethoxybiphenyl (0.050 g, 0.122 mmol) and 2M K$_3$PO$_4$(2.3 mL, 4.60 mmol) in 1,4-dioxane (5 mL) and water (1.000 mL) was degassed for 10 min. Then, Pd(OAc)$_2$ (0.015 g, 0.067 mmol) was added, degassed for 5 min and mixture was heated at 80° C. for 3 h. After cooling, water was added and the mixture was extracted with ethyl acetate, washed with brine, dried (Na$_2$SO$_4$), concentrated and purified by silica gel chromatography (5-40% EtOAc/hexane) to afford (S)-isopropyl 2-(tert-butoxy)-2-(4-(chroman-6-yl)-5-(4-(4-fluorophenethoxy)phenyl)-6-(hydroxymethyl)-2-methylpyridin-3-yl)acetate (0.24 g, 0.374 mmol, 61.1% yield) as white foam. LCMS (M+H)=642.4.

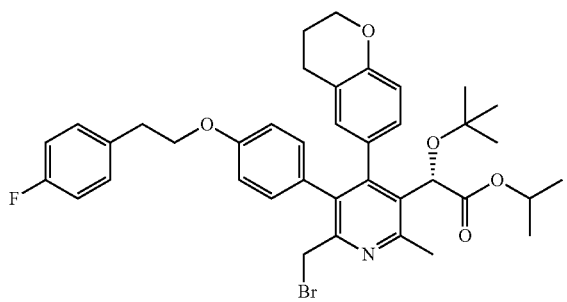 [SMILES: Cc1nc(CBr)c(-c2ccc(OCCc3ccc(F)cc3)cc2)c(-c2ccc3c(c2)CCCO3)c1[C@H](OC(C)(C)C)C(=O)OC(C)C]

(S)-Isopropyl 2-(6-(bromomethyl)-4-(chroman-6-yl)-5-(4-(4-fluorophenethoxy)phenyl)-2-methylpyridin-3-yl)-2-(tert-butoxy)acetate To a solution of (S)-isopropyl 2-(tert-butoxy)-2-(4-(chroman-6-yl)-5-(4-(4-fluorophenethoxy)phenyl)-6-(hydroxymethyl)-2-methylpyridin-3-yl)acetate (0.25 g, 0.390 mmol) in $CH_2Cl_2$ (3 mL) was added $CBr_4$ (0.142 g, 0.429 mmol) followed by $Ph_3P$ (0.112 g, 0.429 mmol) and the resulting mixture was stirred at room temp for 16 h. Then, the reaction mixture was loaded on to a 80 g ISCO cartridge and purified (EtOAc/hex: 0 to 25%) to afford (S)-isopropyl 2-(6-(bromomethyl)-4-(chroman-6-yl)-5-(4-(4-fluorophenethoxy)phenyl)-2-methylpyridin-3-yl)-2-(tert-butoxy)acetate (0.17 g, 0.241 mmol, 61.9% yield) as a solid. LCMS (M+H)= 706.3.

Example 10

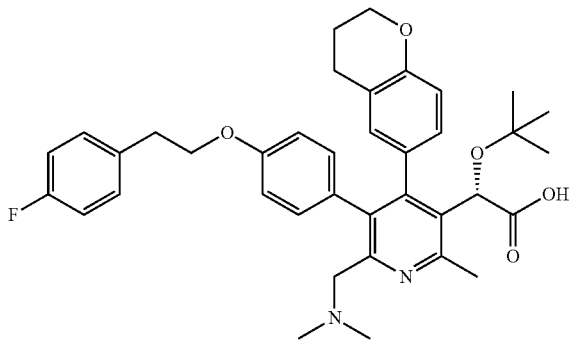 [SMILES: Cc1nc(CN(C)C)c(-c2ccc(OCCc3ccc(F)cc3)cc2)c(-c2ccc3c(c2)CCCO3)c1[C@H](OC(C)(C)C)C(=O)O]

(S)-2-(tert-Butoxy)-2-(4-(chroman-6-yl)-6-((dimethylamino)methyl)-5-(4-(4-fluorophenethoxy)phenyl)-2-methylpyridin-3-yl)acetic Acid To a solution of dimethylamine (0.15 mL, 0.300 mmol) in ethanol (1 mL) was added (S)-isopropyl 2-(6-(bromomethyl)-4-(chroman-6-yl)-5-(4-(4-fluorophenethoxy)phenyl)-2-methylpyridin-3-yl)-2-(tert-butoxy)acetate (0.02 g, 0.028 mmol) and the mixture was stirred at rt for 18 h. NaOH (0.03 g, 0.750 mmol) was added and heated at 80° C. for 3 h, cooled and purified by prep HPLC to afford (S)-2-(tert-butoxy)-2-(4-(chroman-6-yl)-6-((dimethylamino)methyl)-5-(4-(4-fluorophenethoxy)phenyl)-2-methylpyridin-3-yl) acetic acid (0.0137 g, 0.022 mmol, 77% yield). LCMS (M+H)=627.1.

Example 11

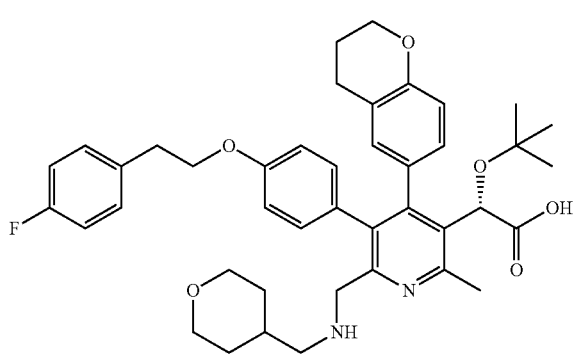 [SMILES: Cc1nc(CNCC2CCOCC2)c(-c2ccc(OCCc3ccc(F)cc3)cc2)c(-c2ccc3c(c2)CCCO3)c1[C@H](OC(C)(C)C)C(=O)O]

(S)-2-(tert-Butoxy)-2-(4-(chroman-6-yl)-5-(4-(4-fluorophenethoxy)phenyl)-2-methyl-6-((((tetrahydro-2H-pyran-4-yl)methyl)amino)methyl)pyridin-3-yl)acetic Acid To a solution of (tetrahydro-2H-pyran-4-yl)methanamine (0.15 mL, 0.028 mmol) in ethanol (1 mL) was added (S)-isopropyl 2-(6-(bromomethyl)-4-(chroman-6-yl)-5-(4-(4-fluorophenethoxy)phenyl)-2-methylpyridin-3-yl)-2-(tert-butoxy)acetate (0.02 g, 0.028 mmol) and the mixture was stirred at rt for 18 h. NaOH (0.03 g, 0.750 mmol) was added and heated at 80° C. for 3 h, cooled and purified by prep HPLC to afford (S)-2-(tert-butoxy)-2-(4-(chroman-6-yl)-5-(4-(4-fluorophenethoxy)phenyl)-2-methyl-6-((((tetrahydro-2H-pyran-4-yl)methyl)amino)methyl)pyridin-3-yl)acetic acid (0.0139 g, 0.020 mmol, 70.3% yield). LCMS (M+H)=697.2.

Example 12

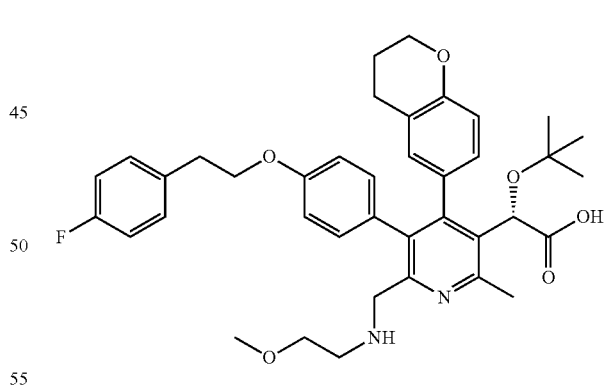

(S)-2-(tert-Butoxy)-2-(4-(chroman-6-yl)-5-(4-(4-fluorophenethoxy)phenyl)-6-(((2-methoxyethyl)amino)methyl)-2-methylpyridin-3-yl)acetic Acid To a solution of 2-methoxyethanamine (0.15 mL, 0.028 mmol) in Ethanol (1 mL) was added (S)-isopropyl 2-(6-(bromomethyl)-4-(chroman-6-yl)-5-(4-(4-fluorophenethoxy)phenyl)-2-methylpyridin-3-yl)-2-(tert-butoxy) acetate (0.02 g, 0.028 mmol) and the mixture was stirred at rt for 18 h. NaOH (0.03 g, 0.750 mmol) was added and heated at 80° C. for 3 h, cooled and purified by prep HPLC to afford (S)-2-(tert-butoxy)-2-(4-(chroman-6-yl)-5-(4-(4-fluorophenethoxy)phenyl)-6-(((2-methoxyethyl)amino)methyl)-2-methylpyridin-3-yl)acetic acid (0.0139 g, 0.021 mmol, 74.6% yield). LCMS (M+H)=657.1.

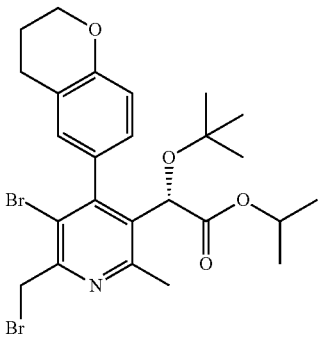

(S)-Isopropyl 2-(5-bromo-6-(bromomethyl)-4-(chroman-6-yl)-2-methylpyridin-3-yl)-2-(tert-butoxy)acetate To a solution of (S)-isopropyl 2-(5-bromo-4-(chroman-6-yl)-6-(hydroxymethyl)-2-methylpyridin-3-yl)-2-(tert-butoxy)acetate (0.27 g, 0.533 mmol) in CH$_2$Cl$_2$ (5 mL) was added CBr$_4$ (0.194 g, 0.586 mmol) followed by Ph$_3$P (0.154 g, 0.586 mmol) and the resulting mixture was stirred at room temp for 16 h, and purified on a 24 g ISCO cartridge (EtOAc/hex: 0 to 25%) to afford (S)-isopropyl 2-(5-bromo-6-(bromomethyl)-4-(chroman-6-yl)-2-methylpyridin-3-yl)-2-(tert-butoxy)acetate (0.26 g, 0.457 mmol, 86% yield). $^1$H NMR (500 MHz, CDCl$_3$) δ 7.05-6.94 (m, 2H), 6.92-6.85 (m, 1H), 5.13-4.99 (m, 1H), 4.94 (2s, 1H), 4.81-4.72 (m, 2H), 4.33-4.26 (m, 2H), 2.94-2.72 (m, 2H), 2.63-2.60 (m, 3H), 2.15-2.02 (m, 2H), 1.31-1.24 (m, 3H), 1.20 (dd, J=7.9, 6.3 Hz, 3H), 1.00 (s, 9H). LCMS (M+H)=570.00

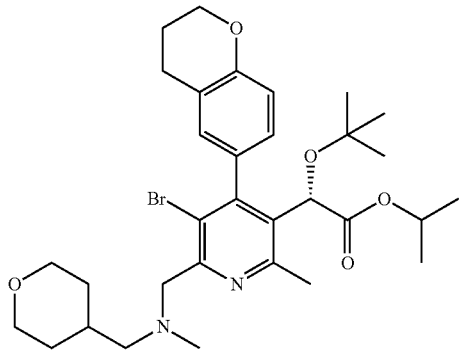 [SMILES: Cc1nc(CN(C)CC2CCOCC2)c(Br)c(-c2ccc3c(c2)CCCO3)c1[C@H](OC(C)(C)C)C(=O)OC(C)C]

(S)-Isopropyl 2-(5-bromo-4-(chroman-6-yl)-2-methyl-6-((methyl((tetrahydro-2H-pyran-4-yl)methyl)amino)methyl)pyridin-3-yl)-2-(tert-butoxy)acetate To a solution of (S)-isopropyl 2-(5-bromo-6-(bromomethyl)-4-(chroman-6-yl)-2-methylpyridin-3-yl)-2-(tert-butoxy)acetate (0.26 g, 0.457 mmol) in ethanol (5 ml) was added N-methyl-1-(tetrahydro-2H-pyran-4-yl)methanamine (0.071 g, 0.548 mmol) and Hunig's base (0.12 ml, 0.687 mmol) and stirred at rt for 3 h. The solvent was evaporated in vacuum and purified by ISCO 24 g column (EtOAc/hex: 0 to 40%) to afford (S)-isopropyl 2-(5-bromo-4-(chroman-6-yl)-2-methyl-6-((methyl((tetrahydro-2H-pyran-4-yl)methyl)amino)methyl)pyridin-3-yl)-2-(tert-butoxy)acetate (0.24 g, 0.389 mmol, 85% yield). $^1$H NMR (500 MHz, CDCl$_3$) δ 7.03-6.80 (m, 3H), 5.15-4.97 (m, 1H), 4.93 (2s, 1H), 4.31-4.24 (m, 2H), 3.97-3.89 (m, 2H), 3.83-3.68 (m, 2H), 3.41-3.32 (m, 2H), 2.80 (s, 2H), 2.63-2.60 (m, 3H), 2.39-2.32 (m, 4H), 2.12-2.08 (m, 1H), 1.84-1.76 (m, 1H), 1.72 (d, J=11.7 Hz, 2H), 1.32-1.13 (m, 9H), 1.00 (s, 9H). LCMS (M+H)=619.3.

Example 13

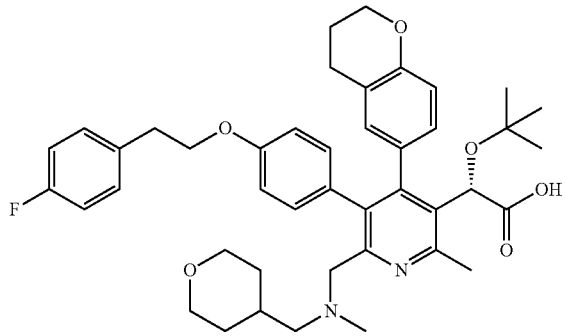 [SMILES: Cc1nc(CN(C)CC2CCOCC2)c(-c2ccc(OCCc3ccc(F)cc3)cc2)c(-c2ccc3c(c2)CCCO3)c1[C@H](OC(C)(C)C)C(=O)O]

(S)-2-(tert-Butoxy)-2-(4-(chroman-6-yl)-5-(4-(4-fluorophenethoxy)phenyl)-2-methyl-6-((methyl((tetrahydro-2H-pyran-4-yl)methyl)amino)methyl)pyridin-3-yl)acetic Acid A mixture of (S)-isopropyl 2-(5-bromo-4-(chroman-6-yl)-2-methyl-6-((methyl((tetrahydro-2H-pyran-4-yl)methyl)amino)methyl)pyridin-3-yl)-2-(tert-butoxy)acetate (0.03 g, 0.049 mmol), (4-(4-fluorophenethoxy)phenyl)boronic acid (0.03 g, 0.115 mmol), K$_2$CO$_3$ (0.2 mL, 0.400 mmol) in 1,4-dioxane (1 mL) was degassed for 10 min. Then, Pd(Ph$_3$P)$_4$ (0.003 g, 2.60 μmol) was added, degassed for 5 min and the mixture was heated at 80° C. for 18 h. The reaction mixture was cooled, 3 ml of MeOH was added, decanted the liquid into another vessel and concentrated. The residue was dissolved in EtOH (1 ml) and sodium hydroxide (0.03 g, 0.750 mmol) was added. The mixture was heated at 80° C. for 3 h, cooled and purified by prep HPLC to afford (S)-2-(tert-butoxy)-2-(4-(chroman-6-yl)-5-(4-(4-fluorophenethoxy)phenyl)-2-methyl-6-((methyl((tetrahydro-2H-pyran-4-yl)methyl)amino)methyl)pyridin-3-yl)acetic acid (0.0274 g, 0.038 mmol, 78% yield). LCMS (M+H)=711.3.

Example 14

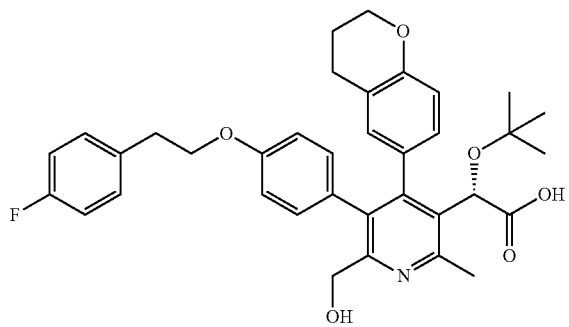 [SMILES: Cc1nc(CO)c(-c2ccc(OCCc3ccc(F)cc3)cc2)c(-c2ccc3c(c2)CCCO3)c1[C@H](OC(C)(C)C)C(=O)O]

(S)-2-(tert-Butoxy)-2-(4-(chroman-6-yl)-5-(4-(4-fluorophenethoxy)phenyl)-6-(hydroxymethyl)-2-methylpyridin-3-yl)acetic Acid To a solution of (S)-isopropyl 2-(6-(bromomethyl)-4-(chroman-6-yl)-5-(4-(4-fluorophenethoxy)phenyl)-2-methylpyridin-3-yl)-2-(tert-butoxy)acetate (0.01 g, 0.014 mmol) in EtOH (1 mL) was added NaOH (0.02 g, 0.500 mmol) and heated at 80° C. for 48 h, cooled and purified by prep HPLC to afford (S)-2-(tert-butoxy)-2-(4-(chroman-6-yl)-5-(4-(4-fluorophenethoxy)phenyl)-6-(hydroxymethyl)-2-methylpyridin-3-yl)acetic acid (0.0026 g, 4.27 μmol, 30.1% yield). LCMS (M+H)=600.1.

Example 15

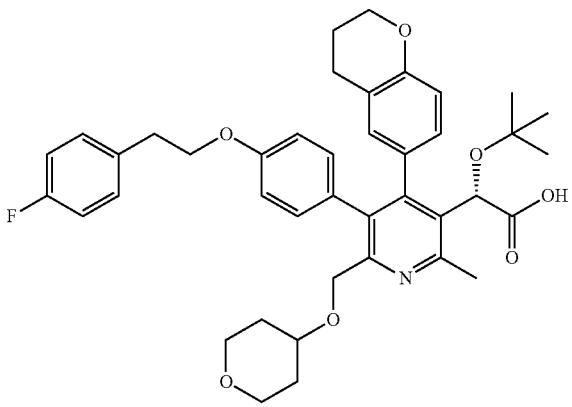 [SMILES: Cc1nc(COC2CCOCC2)c(-c2ccc(OCCc3ccc(F)cc3)cc2)c(-c2ccc3c(c2)CCCO3)c1[C@H](OC(C)(C)C)C(=O)O]

(S)-2-(tert-Butoxy)-2-(4-(chroman-6-yl)-5-(4-(4-fluorophenethoxy)phenyl)-2-methyl-6-(((tetrahydro-2H-pyran-4-yl)oxy)methyl)pyridin-3-yl)acetic Acid To a solution of tetrahydro-2H-pyran-4-ol (0.040 g, 0.392 mmol) and t-BuOK (10 mg, 0.089 mmol) in THF (0.5 mL) was added (S)-isopropyl 2-(6-(bromomethyl)-4-(chroman-6-yl)-5-(4-(4-fluorophenethoxy)phenyl)-2-methylpyridin-3-yl)-2-(tert-butoxy)acetate (0.02 g, 0.028 mmol). The mixture was stirred at rt for 18 h. NaOH (0.03 g, 0.750 mmol) and EtOH (1 ml) were and the mixture heated at 80° C. for 3 h, cooled and purified by prep HPLC to afford (S)-2-(tert-butoxy)-2-(4-(chroman-6-yl)-5-(4-(4-fluorophenethoxy)phenyl)-2-methyl-6-((((tetrahydro-2H-pyran-4-yl)oxy)methyl)pyridin-3-yl)acetic acid (0.0126 g, 0.018 mmol, 64.3% yield). LCMS (M+H)=684.2.

Example 16

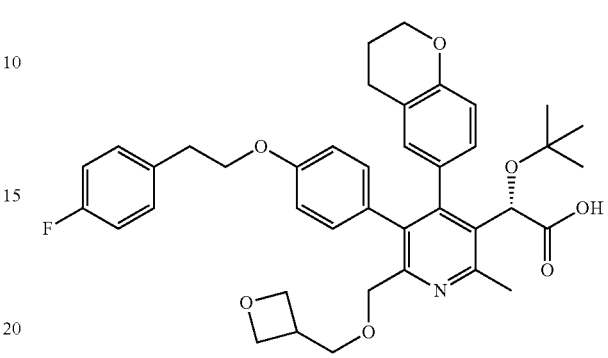

(S)-2-(tert-Butoxy)-2-(4-(chroman-6-yl)-5-(4-(4-fluorophenethoxy)phenyl)-2-methyl-6-((oxetan-3-ylmethoxy)methyl)pyridin-3-yl)acetic Acid To a solution of oxetan-3-ylmethanol (0.04 g, 0.454 mmol) and t-BuOK (10 mg, 0.089 mmol) in THF (0.5 mL) was added (S)-isopropyl 2-(6-(bromomethyl)-4-(chroman-6-yl)-5-(4-(4-fluorophenethoxy)phenyl)-2-methylpyridin-3-yl)-2-(tert-butoxy)acetate (0.02 g, 0.028 mmol). The mixture was stirred at rt for 18 h. NaOH (0.03 g, 0.750 mmol) and EtOH (1 ml) were added and the mixture was heated at 80° C. for 3 h, cooled and purified by prep HPLC to afford (S)-2-(tert-butoxy)-2-(4-(chroman-6-yl)-5-(4-(4-fluorophenethoxy)phenyl)-2-methyl-6-((oxetan-3-ylmethoxy)methyl)pyridin-3-yl)acetic acid (0.0179 g, 0.026 mmol, 93% yield). LCMS (M+H)=670.2.

Example 17

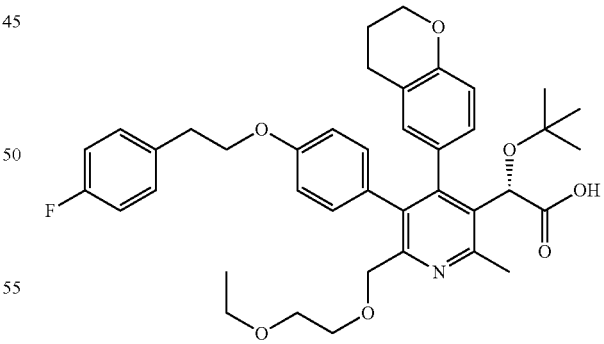

(S)-2-(tert-Butoxy)-2-(4-(chroman-6-yl)-6-((2-ethoxyethoxy)methyl)-5-(4-(4-fluorophenethoxy)phenyl)-2-methylpyridin-3-yl)acetic Acid To a solution of 2-ethoxyethanol (0.04 g, 0.444 mmol) and t-BuOK (10 mg, 0.089 mmol) in THF (0.5 mL) was added (S)-isopropyl 2-(6-(bromomethyl)-4-(chroman-6-yl)-5-(4-(4-fluorophenethoxy)phenyl)-2-methylpyridin-3-yl)-2-

(tert-butoxy)acetate (0.02 g, 0.028 mmol) and the mixture was stirred at rt for 18 h. NaOH (0.03 g, 0.750 mmol) and EtOH (1 ml) were added and heated at 80° C. for 3 h, cooled and purified by prep HPLC to afford (S)-2-(tert-butoxy)-2-(4-(chroman-6-yl)-6-((2-ethoxyethoxy)methyl)-5-(4-(4-fluorophenethoxy)phenyl)-2-methylpyridin-3-yl)acetic acid (0.0173 g, 0.026 mmol, 91% yield). LCMS (M+H)=672.1.

Example 18

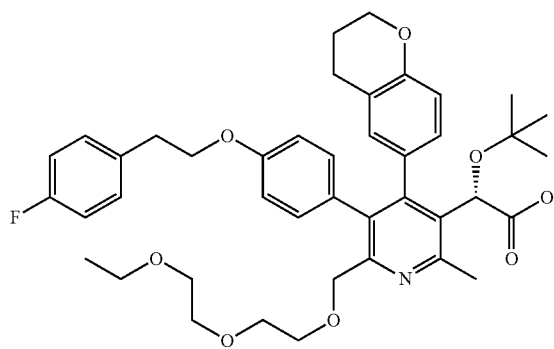

(S)-2-(tert-Butoxy)-2-(4-(chroman-6-yl)-6-((2-(2-ethoxyethoxy)ethoxy)methyl)-5-(4-(4-fluorophenethoxy)phenyl)-2-methylpyridin-3-yl)acetic Acid To a solution of 2-(2-ethoxyethoxy)ethanol (0.04 g, 0.298 mmol) and t-BuOK (10 mg, 0.089 mmol) in THF (0.5 mL) was added (S)-isopropyl 2-(6-(bromomethyl)-4-(chroman-6-yl)-5-(4-(4-fluorophenethoxy)phenyl)-2-methylpyridin-3-yl)-2-(tert-butoxy)acetate (0.02 g, 0.028 mmol) and the mixture was stirred at rt for 18 h. NaOH (0.015 g, 0.375 mmol) and EtOH were added and the mixture was heated at 80° C. for 3 h. Then, cooled and purified by prep HPLC to afford (S)-2-(tert-butoxy)-2-(4-(chroman-6-yl)-6-((2-(2-ethoxyethoxy)methyl)-5-(4-(4-fluorophenethoxy)phenyl)-2-methylpyridin-3-yl)acetic acid (0.013 g, 0.018 mmol, 63.3% yield). LCMS (M+H)=716.1.

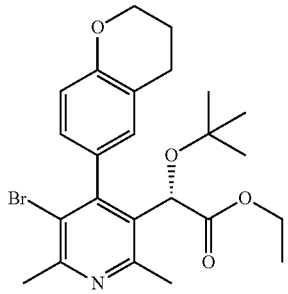 [SMILES: CCOC(=O)[C@@H](OC(C)(C)C)c1c(C)nc(C)c(Br)c1-c1ccc2c(c1)CCCO2]

(S)-Ethyl 2-(5-bromo-4-(chroman-6-yl)-2,6-dimethylpyridin-3-yl)-2-(tert-butoxy)acetate A mixture of (S)-ethyl 2-(5-bromo-4-iodo-2,6-dimethylpyridin-3-yl)-2-(tert-butoxy)acetate (1.73 g, 3.68 mmol), chroman-6-ylboronic acid (0.655 g, 3.68 mmol) and 2M Na₂CO₃ (5.5 mL, 11.00 mmol) in DMF (10 mL) was degassed for 10 min. Then, PdCl₂(dppf)-CH₂Cl₂ adduct (0.150 g, 0.184 mmol) was added, degassed for 5 min and placed in a pre-heated oil bath 60° C. for 5 h. The reaction mixture was cooled down and diluted with EtOAc washed with water, brine, dried (MgSO₄) concentrated and purified by ISCO 80 g column (EtOAc/Hex: 0 to 20%) to afford (S)-ethyl 2-(5-bromo-4-(chroman-6-yl)-2,6-dimethylpyridin-3-yl)-2-(tert-butoxy)acetate (0.7 g, 1.469 mmol, 39.9% yield). LCMS (M+H)=477.8.

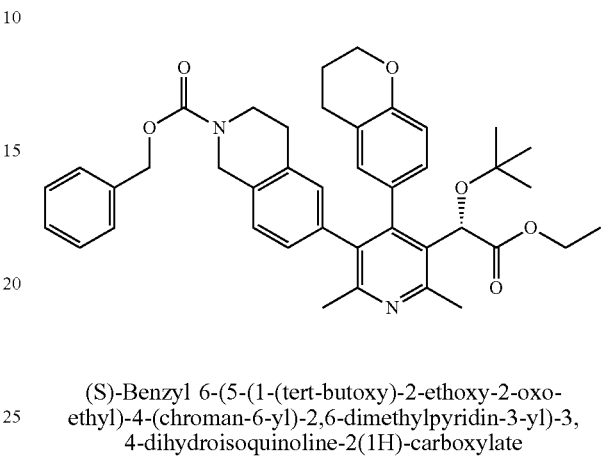

(S)-Benzyl 6-(5-(1-(tert-butoxy)-2-ethoxy-2-oxoethyl)-4-(chroman-6-yl)-2,6-dimethylpyridin-3-yl)-3,4-dihydroisoquinoline-2(1H)-carboxylate A mixture of (S)-ethyl 2-(5-bromo-4-(chroman-6-yl)-2,6-dimethylpyridin-3-yl)-2-(tert-butoxy)acetate (0.7 g, 1.469 mmol), (2-((benzyloxy)carbonyl)-1,2,3,4-tetrahydroisoquinolin-6-yl)boronic acid (0.6 g, 1.928 mmol) and 2M Na₂CO₃ (3.67 mL, 7.35 mmol) in 1,4-dioxane (5 mL) was degassed for 10 min. Then, Pd(Ph₃P)₄ (0.085 g, 0.073 mmol) was added, degassed for 5 min and heated at 90° C. for 16 h. The reaction mixture was diluted with EtOAc and washed with water, brine, dried (MgSO₄), concentrated and purified via ISCO 80 g column (EtOAc/hexanes: 0 to 50%) to afford (S)-benzyl 6-(5-(1-(tert-butoxy)-2-ethoxy-2-oxoethyl)-4-(chroman-6-yl)-2,6-dimethylpyridin-3-yl)-3,4-dihydroisoquinoline-2(1H)-carboxylate (0.51 g, 0.769 mmol, 52.4% yield). LCMS (M+H)=663.7.

Example 19

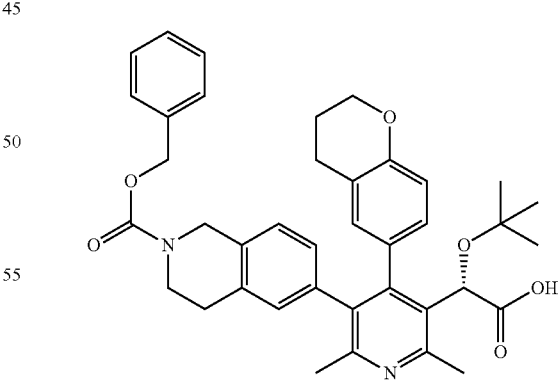

(S)-2-(5-(2-((Benzyloxy)carbonyl)-1,2,3,4-tetrahydroisoquinolin-6-yl)-4-(chroman-6-yl)-2,6-dimethylpyridin-3-yl)-2-(tert-butoxy)acetic Acid A mixture of (S)-benzyl 6-(5-(1-(tert-butoxy)-2-ethoxy-2-oxoethyl)-4-(chroman-6-yl)-2,6-dimethylpyridin-3-yl)-3, 4-dihydroisoquinoline-2(1H)-carboxylate (0.008 g, 0.012 mmol) in EtOH (1 ml) and sodium hydroxide (0.121 ml, 0.121 mmol) was stirred at rt for 6 h, filtered and purified by prep HPLC to afford (S)-2-(5-(2-((benzyloxy)carbonyl)-1,2,3,4-tetrahydroisoquinolin-6-yl)-4-(chroman-6-yl)-2,6-dimethylpyridin-3-yl)-2-(tert-butoxy)acetic acid (0.0056 g, 73%). LCMS (M+H)=635.25.

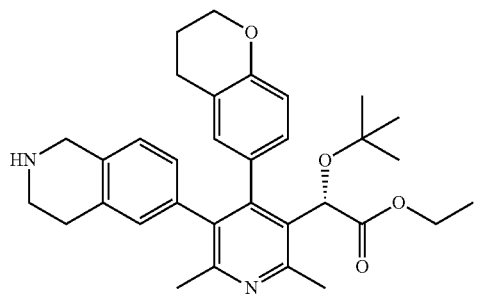 [SMILES: CCOC(=O)[C@@H](OC(C)(C)C)c1c(C)nc(C)c(-c2ccc3c(c2)CCNC3)c1-c1ccc2c(c1)CCCO2]

(S)-Ethyl 2-(tert-butoxy)-2-(4-(chroman-6-yl)-2,6-dimethyl-5-(1,2,3,4-tetrahydroisoquinolin-6-yl)pyridin-3-yl)acetate A solution of (S)-benzyl 6-(5-(1-(tert-butoxy)-2-ethoxy-2-oxoethyl)-4-(chroman-6-yl)-2,6-dimethylpyridin-3-yl)-3,4-dihydroisoquinoline-2(1H)-carboxylate (0.51 g, 0.769 mmol) in MeOH (15 mL) was purged with N₂. 10% Pd/C (0.033 g, 0.031 mmol) was added and degassed and refilled with H₂. The reaction mixture was stirred under H₂ balloon pressure for 2 h. Filtered off the solid and concentrated to dryness to afford (S)-ethyl 2-(tert-butoxy)-2-(4-(chroman-6-yl)-2,6-dimethyl-5-(1,2,3,4-tetrahydroisoquinolin-6-yl)pyridin-3-yl)acetate (0.407 g, 0.769 mmol, 100% yield) as a grey solid. LCMS (M+H)=529.5.

Example 20, 21 and 22

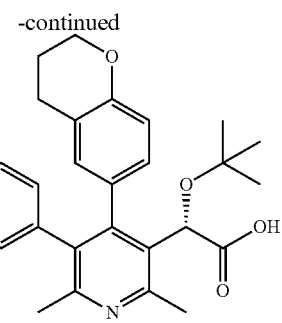

(S)-2-(tert-Butoxy)-2-(4-(chroman-6-yl)-5-(2-(4-fluorobenzyl)-1,2,3,4-tetrahydroisoquinolin-6-yl)-2,6-dimethylpyridin-3-yl)acetic Acid To a solution of (S)-ethyl 2-(tert-butoxy)-2-(4-(chroman-6-yl)-2,6-dimethyl-5-(1,2,3,4-tetrahydroisoquinolin-6-yl)pyridin-3-yl)acetate (0.06 g, 0.113 mmol) in MeOH (1 mL) was added 4-fluorobenzaldehyde (0.06 mL, 0.559 mmol). The mixture was stirred at rt for 2 h and NaBH₄ (20 mg, 0.529 mmol) was added. The mixture was stirred at rt for 1 h and removed the solvent. The residue was treated with EtOAc (5 ml), filtered and concentrated to dryness. The residue was dissolved in EtOH (1 ml) and added sodium hydroxide (60 mg, 1.500 mmol). The mixture was heated at 85° C. in a sealed vial for 4 h, cooled and purified by prep HPLC to afford three product. (S)-2-(tert-Butoxy)-2-(4-(chroman-6-yl)-5-(2-(4-fluorobenzyl)-1,2,3,4-tetrahydroisoquinolin-6-yl)-2,6-dimethylpyridin-3-yl)acetic acid (0.030 g, 0.049 mmol, 43.0% yield). LCMS (M+H)=609.25.

(S)-2-(tert-Butoxy)-2-(4-(chroman-6-yl)-2,6-dimethyl-5-(1,2,3,4-tetrahydroisoquinolin-6-yl)pyridin-3-yl)acetic acid (0.007 g, 0.014 mmol, 11.95% yield). LCMS (M+H)=501.3.

(S)-2-(tert-Butoxy)-2-(4-(chroman-6-yl)-2,6-dimethyl-5-(2-methyl-1,2,3,4-tetrahydroisoquinolin-6-yl)pyridin-3-yl)acetic acid (0.0016 g, 2.98 μmol, 2.63% yield). LCMS (M+H)=515.2.

Example 23

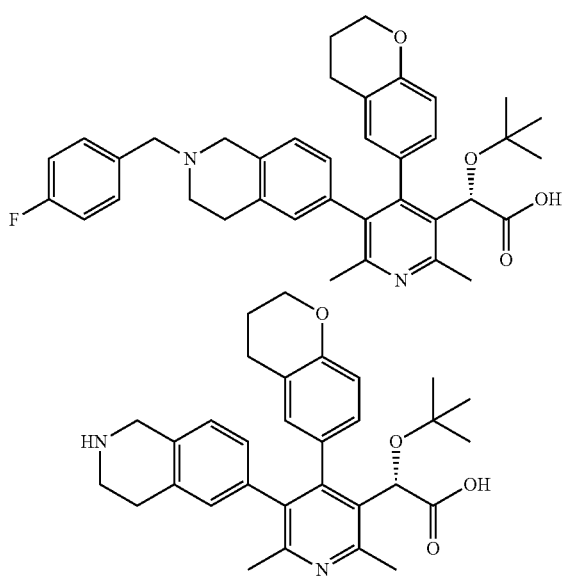

(S)-2-(tert-Butoxy)-2-(4-(chroman-6-yl)-5-(2-(2-fluorobenzyl)-1,2,3,4-tetrahydroisoquinolin-6-yl)-2,6-dimethylpyridin-3-yl)acetic Acid To a solution of (S)-ethyl 2-(tert-butoxy)-2-(4-(chroman-6-yl)-2,6-dimethyl-5-(1,2,3,4-tetrahydroisoquinolin-6-yl)pyridin-3-yl)acetate (0.06 g, 0.113 mmol) in MeOH (1 mL) was added 2-fluorobenzaldehyde (0.1 g, 0.8 mmol). The mixture was stirred at rt for 2 h and NaBH₃CN (60 mg, 0.955 mmol) was added. After 1 h, sodium hydroxide (0.1 g, 2.500 mmol) was added and the mixture was heated at 80° C. in a sealed vial for 18 h. Then, filtered and purified by prep-HPLC to afford (S)-2-(tert-butoxy)-2-(4-(chroman-6-yl)-5-(2-(2-fluorobenzyl)-1,2,3,4-tetrahydroisoquinolin-6-yl)-2,6-dimethylpyridin-3-yl)acetic acid (57.3 mg, 0.090 mmol, 80% yield). LCMS (M+H)=609.00.

Example 24

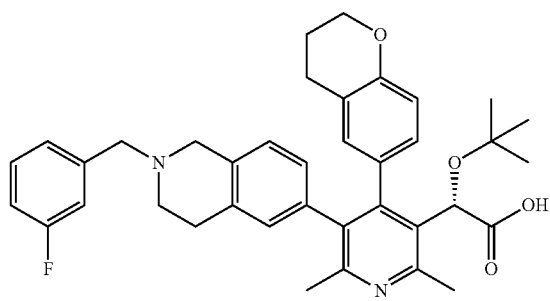 [SMILES: Cc1nc(C)c([C@H](OC(C)(C)C)C(=O)O)c(-c2ccc3c(c2)CCCO3)c1-c1ccc2c(c1)CCN(Cc1cccc(F)c1)C2]

(S)-2-(tert-Butoxy)-2-(4-(chroman-6-yl)-5-(2-(3-fluorobenzyl)-1,2,3,4-tetrahydroisoquinolin-6-yl)-2,6-dimethylpyridin-3-yl)acetic Acid To a solution of (S)-ethyl 2-(tert-butoxy)-2-(4-(chroman-6-yl)-2,6-dimethyl-5-(1,2,3,4-tetrahydroisoquinolin-6-yl)pyridin-3-yl)acetate (0.06 g, 0.113 mmol) in 2-propanol (1 mL) was added 3-fluoro-6-methylbenzaldehyde (0.1. 0.8 mmol). The mixture was stirred at rt for 2 h and NaBH₄(20 mg, 0.529 mmol) was added. The mixture was stirred at rt for 1 h and removed the solvent. The residue was treated with EtOAc (5 ml), filtered and concentrated to dryness. The residue was dissolved in EtOH (1 ml) and added sodium hydroxide (0.1 g, 2.500 mmol). The mixture was heated at 85° C. in a sealed vial for 20 h, filtered and purified by prep HPLC to afford (S)-2-(tert-butoxy)-2-(4-(chroman-6-yl)-5-(2-(3-fluorobenzyl)-1,2,3,4-tetrahydroisoquinolin-6-yl)-2,6-dimethylpyridin-3-yl)acetic acid (0.0305 g, 0.050 mmol, 44.1% yield). LCMS (M+H)=609.1.

Example 25

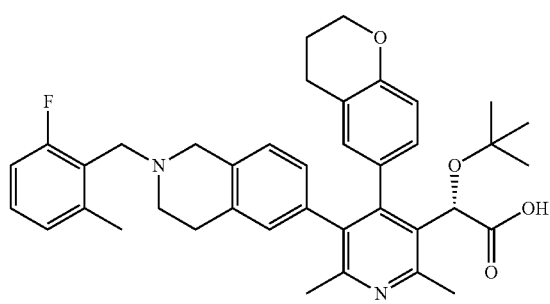 [SMILES: Cc1cccc(F)c1CN1CCc2cc(-c3c(C)nc(C)c([C@H](OC(C)(C)C)C(=O)O)c3-c3ccc4c(c3)CCCO4)ccc2C1]

(S)-2-(tert-Butoxy)-2-(4-(chroman-6-yl)-5-(2-(2-fluoro-6-methylbenzyl)-1,2,3,4-tetrahydroisoquinolin-6-yl)-2,6-dimethylpyridin-3-yl)acetic Acid To a solution of (S)-ethyl 2-(tert-butoxy)-2-(4-(chroman-6-yl)-2,6-dimethyl-5-(1,2,3,4-tetrahydroisoquinolin-6-yl)pyridin-3-yl)acetate (0.06 g, 0.113 mmol) in 2-propanol (1 mL) was added 2-fluoro-6-methylbenzaldehyde (0.006 ml, 01113 mmol). The mixture was stirred at rt for 2 h and NaBH₄(20 mg, 0.529 mmol) was added. The mixture was stirred at rt for 1 h and removed the solvent. The residue was treated with EtOAc (5 ml), filtered and concentrated to dryness. The residue was dissolved in EtOH (1 ml) and added sodium hydroxide (0.1 g, 2.500 mmol). The mixture was heated at 85° C. in a sealed vial for 20 h and purified by prep HPLC to afford (S)-2-(tert-butoxy)-2-(4-(chroman-6-yl)-5-(2-(2-fluoro-6-methylbenzyl)-1,2,3,4-tetrahydroisoquinolin-6-yl)-2,6-dimethylpyridin-3-yl)acetic acid (0.0062, 8.8%). ¹H NMR (500 MHz, DMSO-d6) δ 7.23-7.16 (m, 1H), 7.07-6.89 (m, 6H), 6.81-6.70 (m, 1H), 6.70-6.59 (m, 1H), 6.53 (br. s., 1H), 6.49-6.39 (m, 2H), 4.96-4.83 (m, 1H), 4.08 (br. s., 1H), 4.03 (br. s., 1H), 3.60 (d, J=7.3 Hz, 2H), 3.50 (br. s., 2H), 2.85-2.56 (m, 3H), 2.39 (br. s., 3H), 2.19-2.06 (m, 3H), 1.88-1.82 (m, 1H), 1.86 (s, 1H), 1.75 (br. s., 1H), 0.87 (s, 9H). LCMS(M+H)=623.1.

Example 26

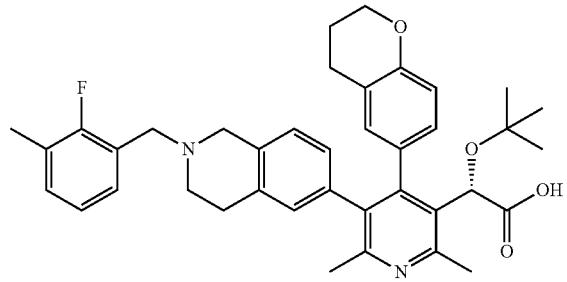 [SMILES: Cc1cccc(CN2CCc3cc(-c4c(C)nc(C)c([C@H](OC(C)(C)C)C(=O)O)c4-c4ccc5c(c4)CCCO5)ccc3C2)c1F]

(S)-2-(tert-Butoxy)-2-(4-(chroman-6-yl)-5-(2-(2-fluoro-3-methylbenzyl)-1,2,3,4-tetrahydroisoquinolin-6-yl)-2,6-dimethylpyridin-3-yl)acetic Acid To a solution of (S)-ethyl 2-(tert-butoxy)-2-(4-(chroman-6-yl)-2,6-dimethyl-5-(1,2,3,4-tetrahydroisoquinolin-6-yl)pyridin-3-yl)acetate (0.06 g, 0.113 mmol) in EtOH (1 mL) was added 2-fluoro-3-methylbenzaldehyde (0.05 g, 0.362 mmol). The mixture was stirred at 60° C. for 2 h and NaBH(OAc)₃(0.1 g, 0.472 mmol) was added. The mixture was stirred at rt for 18 h and then sodium hydroxide (0.05 g, 1.250 mmol) added. The mixture was heated at 80° C. in a sealed vial for 18 h. Then, filtered and purified by prep HPLC to afford (S)-2-(tert-butoxy)-2-(4-(chroman-6-yl)-5-(2-(2-fluoro-3-methylbenzyl)-1,2,3,4-tetrahydroisoquinolin-6-yl)-2,6-dimethylpyridin-3-yl)acetic acid (0.0586 g, 0.094 mmol, 83% yield). LCMS(M+H)=623.1.

Example 27

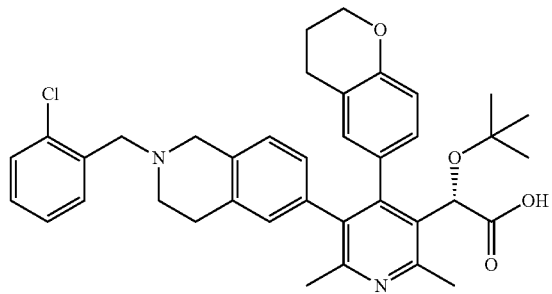

(S)-2-(tert-Butoxy)-2-(5-(2-(2-chlorobenzyl)-1,2,3,4-tetrahydroisoquinolin-6-yl)-4-(chroman-6-yl)-2,6-dimethylpyridin-3-yl)acetic Acid To a solution of (S)-ethyl 2-(tert-butoxy)-2-(4-(chroman-6-yl)-2,6-dimethyl-5-(1,2,3,4-tetrahydroisoquinolin-6-yl) pyridin-3-yl)acetate (0.03 g, 0.057 mmol) in EtOH (1 mL) was added 2-chlorobenzaldehyde (0.02 g, 0.142 mmol). The mixture was stirred at rt for 2 h and NaBH(OAc)$_3$(0.04 g, 0.189 mmol) was added. The mixture was stirred at rt for 3 h and added sodium hydroxide (0.05 g, 1.250 mmol) and heated at 85° C. in a sealed vial for 18 h, filtered and purified by prep-HPLC to afford to afford (S)-2-(tert-butoxy)-2-(5-(2-(2-chlorobenzyl)-1,2,3,4-tetrahydroisoquinolin-6-yl)-4-(chroman-6-yl)-2,6-dimethylpyridin-3-yl)acetic acid (0.0232 g, 0.037 mmol, 65.4% yield). LCMS (M+H)=625.0.

Example 28

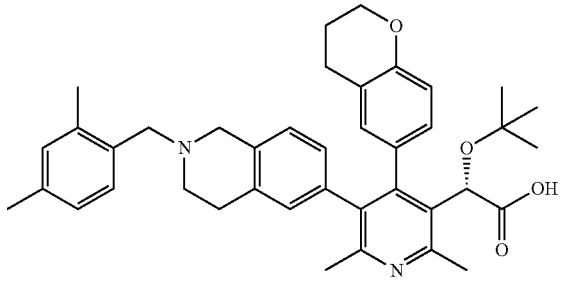 [SMILES: Cc1ccc(CN2CCc3cc(-c4c(C)nc(C)c([C@H](OC(C)(C)C)C(=O)O)c4-c4ccc5c(c4)CCCO5)ccc3C2)c(C)c1]

(S)-2-(tert-Butoxy)-2-(4-(chroman-6-yl)-5-(2-(2,4-dimethylbenzyl)-1,2,3,4-tetrahydroisoquinolin-6-yl)-2,6-dimethylpyridin-3-yl)acetic Acid A solution of (S)-ethyl 2-(tert-butoxy)-2-(4-(chroman-6-yl)-2,6-dimethyl-5-(1,2,3,4-tetrahydroisoquinolin-6-yl)pyridin-3-yl)acetate (0.04 g, 0.076 mmol) and 2,4-dimethylbenzaldehyde (16 mg, 0.119 mmol) in EtOH (1 mL) was stirred at rt for 1 h. NaBH(OAc)$_3$(40 mg, 0.189 mmol) was added and the mixture was stirred at rt for 2 h. Then, sodium hydroxide (0.006 mg, 0.150 µmol) was added and heated at 85° C. in a sealed vial for 2 h, cooled and purified by prep HPLC to afford (S)-2-(tert-butoxy)-2-(4-(chroman-6-yl)-5-(2-(2,4-dimethylbenzyl)-1,2,3,4-tetrahydroisoquinolin-6-yl)-2,6-dimethylpyridin-3-yl)acetic acid (0.0277 g, 0.045 mmol, 59.2% yield). LCMS (M+H)=617.2.

Example 29

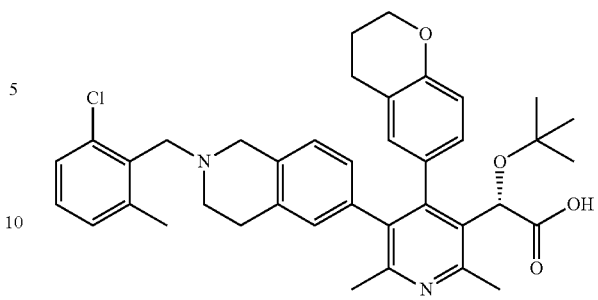

(S)-2-(tert-Butoxy)-2-(5-(2-(2-chloro-6-methylbenzyl)-1,2,3,4-tetrahydroisoquinolin-6-yl)-4-(chroman-6-yl)-2,6-dimethylpyridin-3-yl)acetic Acid A solution of (S)-ethyl 2-(tert-butoxy)-2-(4-(chroman-6-yl)-2,6-dimethyl-5-(1,2,3,4-tetrahydroisoquinolin-6-yl)pyridin-3-yl)acetate (0.04 g, 0.076 mmol) and 2-chloro-6-methylbenzaldehyde (16 mg, 0.103 mmol) in EtOH (1 mL) was stirred at rt for 1 h. Then, NaBH(OAc)$_3$(40 mg, 0.189 mmol) was added and stirred at rt for 1 h. To this NaOH (60 mg, 1.500 mmol) was added and the mixture heated at 85° C. in a sealed vial for 3 h. Then, cooled and purified by prep HPLC to afford (S)-2-(tert-butoxy)-2-(5-(2-(2-chloro-6-methylbenzyl)-1,2,3,4-tetrahydroisoquinolin-6-yl)-4-(chroman-6-yl)-2,6-dimethylpyridin-3-yl)acetic acid (0.0327 g, 0.048 mmol, 63.6% yield). LCMS (M+H)=639.2.

Example 30

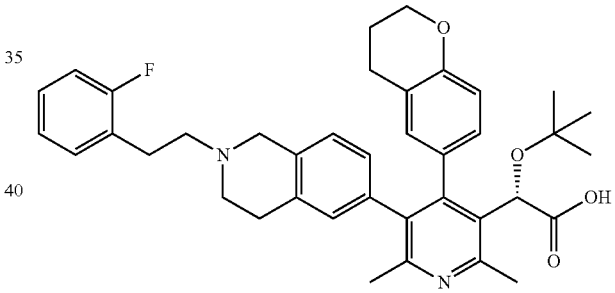

(S)-2-(tert-Butoxy)-2-(4-(chroman-6-yl)-5-(2-(2-fluorophenethyl)-1,2,3,4-tetrahydroisoquinolin-6-yl)-2,6-dimethylpyridin-3-yl)acetic Acid To a solution of (S)-ethyl 2-(tert-butoxy)-2-(4-(chroman-6-yl)-2,6-dimethyl-5-(1,2,3,4-tetrahydroisoquinolin-6-yl) pyridin-3-yl)acetate (0.06 g, 0.113 mmol) and DIPEA (0.059 mL, 0.340 mmol) in DCM (0.5 mL) was added 1-(2-bromoethyl)-2-fluorobenzene (0.06 g, 0.295 mmol) and stirred for 2 h. Another portion of DIPEA (0.059 mL, 0.340 mmol) and 1-(2-bromoethyl)-2-fluorobenzene (0.06 g, 0.295 mmol) was added and stirred for 20 h. The solvent was removed and the residue was dissolved in 2 ml of EtOH. Sodium hydroxide (0.1 g, 2.500 mmol) was added and the mixture was heated at 80° C. for 18 h. Then, filtered and purified by prep HPLC to afford (S)-2-(tert-butoxy)-2-(4-(chroman-6-yl)-5-(2-(2-fluorophenethyl)-1,2,3,4-tetrahydroisoquinolin-6-yl)-2,6-dimethylpyridin-3-yl)acetic acid (0.0436 g, 0.070 mmol, 61.7% yield). LCMS 2 (M+H)=623. $^1$H NMR (500 MHz, DMSO-d6) δ 7.36 (br. s., 1H), 7.27-7.21 (m, 1H), 7.17-7.10 (m, 2H), 7.04-6.95 (m, 2H), 6.85-6.36 (m, 4H), 4.95-4.85 (m, 1H), 4.09 (br. s., 1H), 4.04 (br. s., 1H), 3.65-3.46 (m, 2H), 2.85 (br. s., 2H), 2.78 (br. s., 1H), 2.69-2.61 (m, 5H), 2.52 (br. s., 3H), 2.40-2.27 (m, 1H), 2.17 (s, 3H), 1.87 (br. s., 1H), 1.76 (br. s., 1H), 0.93-0.81 (m, 9H).

Example 31

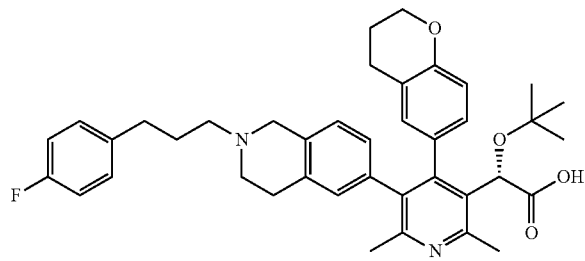 [SMILES: Cc1nc(C)c([C@H](OC(C)(C)C)C(=O)O)c(-c2ccc3c(c2)CCCO3)c1-c1ccc2c(c1)CCN(CCCc1ccc(F)cc1)C2]

(S)-2-(tert-Butoxy)-2-(4-(chroman-6-yl)-5-(2-(3-(4-fluorophenyl)propyl)-1,2,3,4-tetrahydroisoquinolin-6-yl)-2,6-dimethylpyridin-3-yl)acetic Acid To a solution of (S)-ethyl 2-(tert-butoxy)-2-(4-(chroman-6-yl)-2,6-dimethyl-5-(1,2,3,4-tetrahydroisoquinolin-6-yl) pyridin-3-yl)acetate (0.03 g, 0.057 mmol) in EtOH (1 mL) was added 3-(4-fluorophenyl)propanal (0.03 g, 0.197 mmol). The mixture was stirred at rt for 2 h and NaBH(OAc)$_3$ (0.060 g, 0.284 mmol) was added. The mixture was stirred at rt for 18 h and then sodium hydroxide (0.05 g, 1.250 mmol) added. The mixture was heated at 80° C. in a sealed vial for 18 h, filtered and purified by prep-HPLC to afford (S)-2-(tert-butoxy)-2-(4-(chroman-6-yl)-5-(2-(3-(4-fluorophenyl)propyl)-1,2,3,4-tetrahydroisoquinolin-6-yl)-2,6-dimethylpyridin-3-yl)acetic acid (0.0359 g, 0.054 mmol, 94% yield). LCMS (M+H)=637.1: $^1$H NMR (500 MHz, DMSO-d6) δ 7.25 (br. s., 2H), 7.18-7.06 (m, J=8.6, 8.6 Hz, 3H), 7.02-6.92 (m, 2H), 6.81-6.34 (m, 3H), 4.82, 4.84 (2s, 1H), 4.08 (br. s., 1H), 4.03 (br. s., 1H), 3.45-3.39 (m, 2H), 2.83-2.74 (m, 1H), 2.66 (br. s., 2H), 2.61 (br. s., 3H), 2.40 (br. s., 2H), 2.22-2.10 (m, 3H), 1.78 (br. s., 4H), 0.86, 0.84 (2s, 9H). 5 protons not resolved.

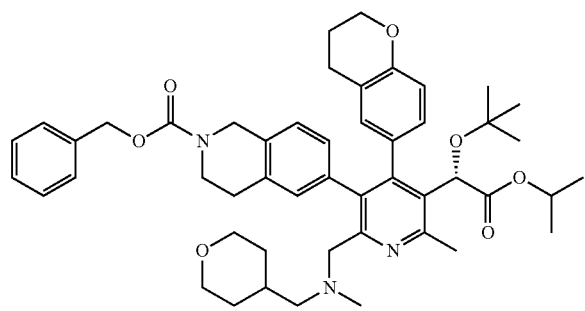 [SMILES: Cc1nc(CN(C)CC2CCOCC2)c(-c2ccc3c(c2)CCN(C(=O)OCc2ccccc2)C3)c(-c2ccc3c(c2)CCCO3)c1[C@H](OC(C)(C)C)C(=O)OC(C)C]

(S)-Benzyl 6-(5-(1-(tert-butoxy)-2-isopropoxy-2-oxoethyl)-4-(chroman-6-yl)-6-methyl-2-((methyl((tetrahydro-2H-pyran-4-yl)methyl)amino)methyl) pyridin-3-yl)-3,4-dihydroisoquinoline-2(1H)-carboxylate A mixture of (S)-isopropyl 2-(5-bromo-4-(chroman-6-yl)-2-methyl-6-((methyl((tetrahydro-2H-pyran-4-yl)methyl) amino)methyl)pyridin-3-yl)-2-(tert-butoxy)acetate (0.21 g, 0.340 mmol), benzyl 6-(6-methyl-4,8-dioxo-1,3,6,2-dioxazaborocan-2-yl)-3,4-dihydroisoquinoline-2(1H)-carboxylate (0.3 g, 0.710 mmol), 2-dicyclohexylphosphino-2',6'-dimethoxybiphenyl (0.028 g, 0.068 mmol) and 2M K$_3$PO$_4$ (1.4 mL, 2.80 mmol) in 1,4-dioxane (4 mL) and water (0.800 mL) was degassed for 10 min. Then, Pd(OAc)$_2$ (0.008 g, 0.036 mmol) was added, degassed for 5 min and mixture was heated at 80° C. for 3 h. After cooling to room temperature, water was added and the mixture was extracted with ethyl acetate, washed with brine, dried (Na$_2$SO$_4$), filtered and concentrated. The residue was purified by Biotage (5-60% EtOAc/hexane) to afford (S)-benzyl 6-(5-(1-(tert-butoxy)-2-isopropoxy-2-oxoethyl)-4-(chroman-6-yl)-6-methyl-2-((methyl((tetrahydro-2H-pyran-4-yl)methyl) amino)methyl)pyridin-3-yl)-3,4-dihydroisoquinoline-2 (1H)-carboxylate (0.19 g, 0.236 mmol, 69.5% yield) as white foam. LCMS (M+H)=804.6.

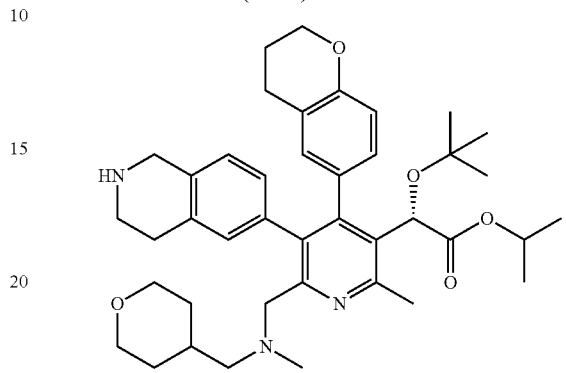

(S)-Isopropyl 2-(tert-butoxy)-2-(4-(chroman-6-yl)-2-methyl-6-((methyl((tetrahydro-2H-pyran-4-yl) methyl)amino)methyl)-5-(1,2,3,4-tetrahydroisoquinolin-6-yl)pyridin-3-yl)acetate A solution of (S)-benzyl 6-(5-(1-(tert-butoxy)-2-isopropoxy-2-oxoethyl)-4-(chroman-6-yl)-6-methyl-2-((methyl((tetrahydro-2H-pyran-4-yl)methyl)amino)methyl) pyridin-3-yl)-3,4-dihydroisoquinoline-2(1H)-carboxylate (0.19 g, 0.236 mmol) in ethanol (5 mL) was added HCl (0.8 mL, 0.800 mmol) and then purged with N$_2$. 10% Pd/C (0.025 g, 0.024 mmol) was added, degassed, filled with H$_2$. The reaction mixture was stirred under H$_2$ balloon pressure for 4 h, filtered off the solid and concentrated to dryness to afford (S)-isopropyl 2-(tert-butoxy)-2-(4-(chroman-6-yl)-2-methyl-6-((methyl((tetrahydro-2H-pyran-4-yl)methyl) amino)methyl)-5-(1,2,3,4-tetrahydroisoquinolin-6-yl)pyridin-3-yl)acetate (0.158 g, 0.236 mmol, 100% yield) as a grey solid. LCMS (M+H)=670.6.

Example 32

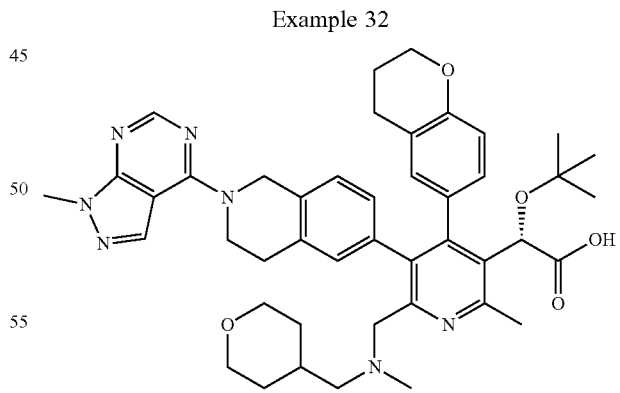

(S)-2-(tert-Butoxy)-2-(4-(chroman-6-yl)-2-methyl-6-((methyl((tetrahydro-2H-pyran-4-yl)methyl)amino) methyl)-5-(2-(1-methyl-1H-pyrazolo[3,4-d]pyrimidin-4-yl)-1,2,3,4-tetrahydroisoquinolin-6-yl)pyridin-3-yl)acetic Acid To a mixture of (S)-isopropyl 2-(tert-butoxy)-2-(4-(chroman-6-yl)-2-methyl-6-((methyl((tetrahydro-2H-pyran-4-yl)

methyl)amino)methyl)-5-(1,2,3,4-tetrahydroisoquinolin-6-yl)pyridin-3-yl)acetate, 3 HCl (0.020 g, 0.026 mmol), and 4-chloro-1-methyl-1H-pyrazolo[3,4-d]pyrimidine (0.010 g, 0.059 mmol) in a vial were added acetonitrile (1 mL) and cesium carbonate (0.042 g, 0.128 mmol), sealed and heated at 90° C. for 18 h. Then, filtered off the solid, (washed the solid with EtOH) and the filtrate was concentrated and redissolved in EtOH (0.5 ml). NaOH (1.027 mg, 0.026 mmol) was added and the mixture heated at 80° C. for 2 h. Then, cooled and purified by Prep HPLC to afford (S)-2-(tert-butoxy)-2-(4-(chroman-6-yl)-2-methyl-6-((methyl((tetrahydro-2H-pyran-4-yl)methyl)amino)methyl)-5-(2-(1-methyl-1H-pyrazolo[3,4-d]pyrimidin-4-yl)-1,2,3,4-tetrahydroisoquinolin-6-yl)pyridin-3-yl)acetic acid (0.0082 g, 10.79 µmol, 42.0% yield). LCMS (M+H)=760.3.

Example 33

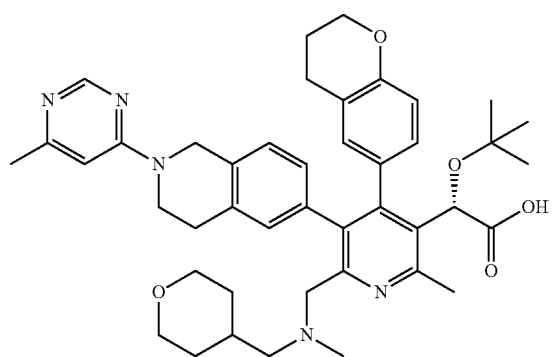 [SMILES: Cc1cc(N2CCc3cc(-c4c(CN(C)CC5CCOCC5)nc(C)c([C@H](OC(C)(C)C)C(=O)O)c4-c4ccc5c(c4)CCCO5)ccc3C2)ncn1]

(S)-2-(tert-Butoxy)-2-(4-(chroman-6-yl)-2-methyl-6-((methyl((tetrahydro-2H-pyran-4-yl)methyl)amino)methyl)-5-(2-(6-methylpyrimidin-4-yl)-1,2,3,4-tetrahydroisoquinolin-6-yl)pyridin-3-yl)acetic Acid A solution of (S)-isopropyl 2-(tert-butoxy)-2-(4-(chroman-6-yl)-2-methyl-6-((methyl((tetrahydro-2H-pyran-4-yl)methyl)amino)methyl)-5-(1,2,3,4-tetrahydroisoquinolin-6-yl)pyridin-3-yl)acetate, 3 HCl (0.015 g, 0.019 mmol), 4-chloro-6-methylpyrimidine (3.71 mg, 0.029 mmol) and potassium carbonate (0.03 g, 0.217 mmol) in dioxane (1 mL) was stirred at 100° C. for 18 h, cooled and treated with sodium hydroxide (0.02 g, 0.500 mmol) in EtOH (1 ml) at 85° C. for 2 h. Then, cooled and purified by prep HPLC to afford (S)-2-(tert-butoxy)-2-(4-(chroman-6-yl)-2-methyl-6-((methyl((tetrahydro-2H-pyran-4-yl)methyl)amino)methyl)-5-(2-(6-methylpyrimidin-4-yl)-1,2,3,4-tetrahydroisoquinolin-6-yl)pyridin-3-yl)acetic acid (0.0029 g, 3.83 µmol, 19.88% yield). LCMS (M+H)=720.2.

Example 34

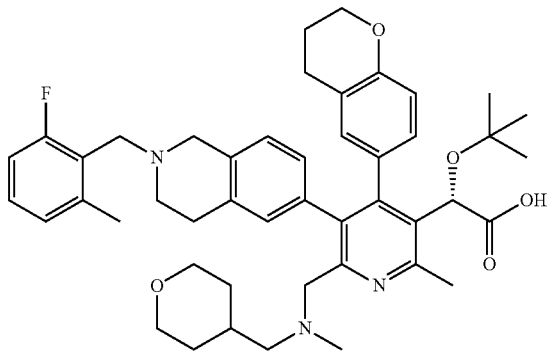 [SMILES: Cc1cccc(F)c1CN1CCc2cc(-c3c(CN(C)CC4CCOCC4)nc(C)c([C@H](OC(C)(C)C)C(=O)O)c3-c3ccc4c(c3)CCCO4)ccc2C1]

(S)-2-(tert-Butoxy)-2-(4-(chroman-6-yl)-5-(2-(2-fluoro-6-methylbenzyl)-1,2,3,4-tetrahydroisoquinolin-6-yl)-2-methyl-6-((methyl((tetrahydro-2H-pyran-4-yl)methyl)amino)methyl)pyridin-3-yl)acetic Acid A solution of (S)-isopropyl 2-(tert-butoxy)-2-(4-(chroman-6-yl)-2-methyl-6-((methyl((tetrahydro-2H-pyran-4-yl)methyl)amino)methyl)-5-(1,2,3,4-tetrahydroisoquinolin-6-yl)pyridin-3-yl)acetate, 3 HCl (0.015 g, 0.019 mmol), TEA (0.01 ml, 0.072 mmol) and 2-fluoro-6-methylbenzaldehyde (6 mg, 0.043 mmol) in EtOH (1 mL) was stirred at rt for 20 h, and NaBH(OAc)₃ (0.012 g, 0.057 mmol) was added. After 2 h, sodium hydroxide (0.02 g, 0.500 mmol) was added, heated at 85° C. in a sealed vial for 2 h, cooled and purified by prep HPLC to afford (S)-2-(tert-butoxy)-2-(4-(chroman-6-yl)-5-(2-(2-fluoro-6-methylbenzyl)-1,2,3,4-tetrahydroisoquinolin-6-yl)-2-methyl-6-((methyl((tetrahydro-2H-pyran-4-yl)methyl)amino)methyl)pyridin-3-yl)acetic acid (0.0066 g, 8.71 µmol, 45.3% yield). LCMS (M+H)=750.3.

Example 35

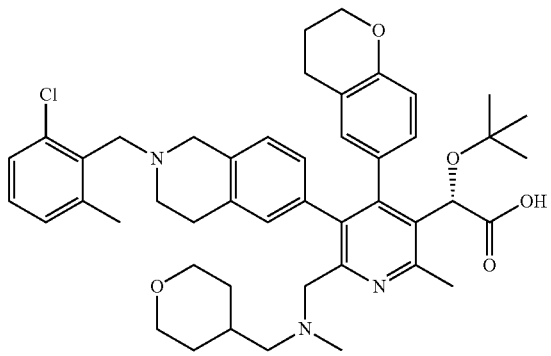 [SMILES: Cc1cccc(Cl)c1CN1CCc2cc(-c3c(CN(C)CC4CCOCC4)nc(C)c([C@H](OC(C)(C)C)C(=O)O)c3-c3ccc4c(c3)CCCO4)ccc2C1]

(S)-2-(tert-Butoxy)-2-(5-(2-(2-chloro-6-methylbenzyl)-1,2,3,4-tetrahydroisoquinolin-6-yl)-4-(chroman-6-yl)-2-methyl-6-((methyl((tetrahydro-2H-pyran-4-yl)methyl)amino)methyl)pyridin-3-yl)acetic Acid A solution of (S)-isopropyl 2-(tert-butoxy)-2-(4-(chroman-6-yl)-2-methyl-6-((methyl((tetrahydro-2H-pyran-4-yl)methyl)amino)methyl)-5-(1,2,3,4-tetrahydroisoquinolin-6- yl)pyridin-3-yl)acetate, 3 HCl (0.015 g, 0.019 mmol), TEA (0.01 ml, 0.072 mmol) and 2-chloro-6-methylbenzaldehyde (6 mg, 0.039 mmol) in EtOH (1 mL) was stirred at rt for 20 h, and NaBH(OAc)₃ (0.012 g, 0.057 mmol) was added. After 2 h, sodium hydroxide (0.02 g, 0.500 mmol) was added, heated at 85° C. in a sealed vial for 2 h, cooled and purified by prep HPLC to afford (S)-2-(tert-butoxy)-2-(5-(2-(2-chloro-6-methylbenzyl)-1,2,3,4-tetrahydroisoquinolin-6-yl)-4-(chroman-6-yl)-2-methyl-6-((methyl((tetrahydro-2H-pyran-4-yl)methyl)amino)methyl)pyridin-3-yl)acetic acid (0.0047 g, 6.13 μmol, 31.9% yield). LCMS (M+H)=766.3.

6-Bromo-4,4-difluorochroman

To a solution of 6-bromochroman-4-one (1 g, 4.40 mmol) in CH₂Cl₂ (6 mL) in ice water bath was added deoxofluor (2.1 mL, 11.39 mmol), followed by catalytic amount of EtOH (0.005 mL, 0.086 mmol). The resulting yellowish solution was stirred overnight at rt. Another portion of deoxofluor (2.1 mL, 11.39 mmol) was added and the reaction mixture was stirred rt for 14 days. The reaction mixture was partitioned between cold sat. Na₂CO₃ and EtOAc. The organic phase was washed with sat. NaHCO₃, water, sat. NaCl and dried over anhydrous MgSO₄, filtered and purified on a 80 g silica gel column (EtOAc/hexane: 0 to 50%) to afford 6-bromo-4,4-difluorochroman (0.36 g, 1.445 mmol, 32.8% yield) as a colorless solid. ¹H NMR (500 MHz, CDCl₃) δ 7.77-7.71 (m, 1H), 7.48-7.42 (m, 1H), 6.81 (dt, J=8.8, 1.2 Hz, 1H), 4.43-4.33 (m, 2H), 2.55-2.40 (m, 2H).

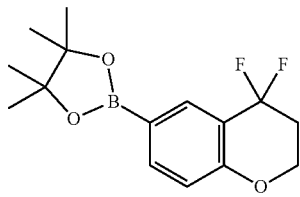 [SMILES: CC1(C)OB(c2ccc3c(c2)C(F)(F)CCO3)OC1(C)C]

2-(4,4-Difluorochroman-6-yl)-4,4,5,5-tetramethyl-1,3,2-dioxaborolane

A mixture of 6-bromo-4,4-difluorochroman (0.54 g, 2.168 mmol), 4,4,4',4',5,5,5',5'-octamethyl-2,2'-bi(1,3,2-dioxaborolane) (1.1 g, 4.33 mmol) and KOAc (0.64 g, 6.52 mmol) in dioxane (15 mL) was degassed for 5 min, and refilled N₂ back. Pd(Ph₃P)₄ (0.12 g, 0.104 mmol) was added to the mixture. The brown mixture was degassed, refilled N₂. The reaction mixture was stirred in 80° C. for 18 h and diluted with EtOAc, washed water, brine, dried (MgSO₄), evaporated and purified on ISCO 40 g column (0-50% EtOAc/Hex) to afford 2-(4,4-difluorochroman-6-yl)-4,4,5,5-tetramethyl-1,3,2-dioxaborolane (0.42 g, 1.418 mmol, 65.4% yield). ¹H NMR (500 MHz, CDCl₃) δ 8.11 (s, 1H), 7.79 (d, J=8.4 Hz, 1H), 6.90 (d, J=8.2 Hz, 1H), 4.43-4.32 (m, 2H), 2.53-2.43 (m, 2H), 1.36 (s, 12H).

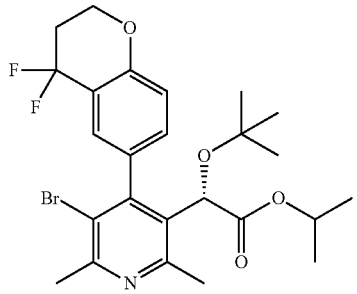 [SMILES: Cc1nc(C)c([C@H](OC(C)(C)C)C(=O)OC(C)C)c(-c2ccc3c(c2)C(F)(F)CCO3)c1Br]

(S)-Isopropyl 2-(5-bromo-4-(4,4-difluorochroman-6-yl)-2,6-dimethylpyridin-3-yl)-2-(tert-butoxy)acetate A mixture of (S)-isopropyl 2-(5-bromo-4-iodo-2,6-dimethylpyridin-3-yl)-2-(tert-butoxy)acetate (0.15 g, 0.310 mmol), 2-(4,4-difluoroisochroman-6-yl)-4,4,5,5-tetramethyl-1,3,2-dioxaborolane (0.092 g, 0.310 mmol) and 2M Na₂CO₃ (0.5 mL, 1.000 mmol) in dioxanes (2 mL) was degassed. Then, PdCl₂(dppf)-CH₂Cl₂ adduct (0.013 g, 0.015 mmol) was added, degassed for 5 min and placed in a pre-heated oil bath 60° C. for 5 h. The reaction mixture was cooled and diluted with EtOAc washed with water, brine, dried (MgSO₄) concentrated and purified by ISCO 80 g column (EtOAc/Hex: 0 to 20%) to afford (S)-isopropyl 2-(5-bromo-4-(4,4-difluorochroman-6-yl)-2,6-dimethylpyridin-3-yl)-2-(tert-butoxy)acetate (0.05 g, 0.095 mmol, 30.7% yield). LCMS (M+H)=528.3.

Example 36

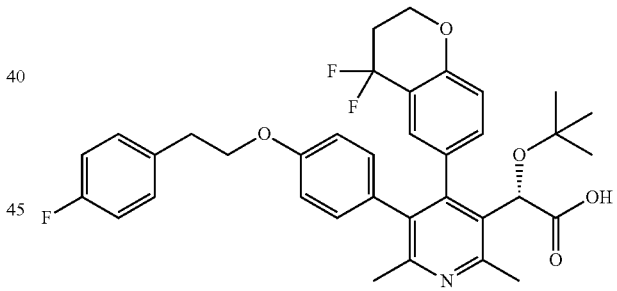

(S)-2-(tert-Butoxy)-2-(4-(4,4-difluorochroman-6-yl)-5-(4-(4-fluorophenethoxy)phenyl)-2,6-dimethylpyridin-3-yl)acetic Acid A mixture of (S)-isopropyl 2-(5-bromo-4-(4,4-difluorochroman-6-yl)-2,6-dimethylpyridin-3-yl)-2-(tert-butoxy)acetate (0.05 g, 0.095 mmol), 2-(4-(4-fluorophenethoxy)phenyl)-6-methyl-1,3,6,2-dioxazaborocane-4,8-dione (0.06 g, 0.162 mmol), 2-dicyclohexylphosphino-2',6'-dimethoxybiphenyl (8 mg, 0.019 mmol), water (0.5 mL) and 2M K₃PO₄ (0.5 mL, 1.000 mmol) in 1,4-dioxane (1 mL) and was degassed for 5 min. Then, Pd(OAc)₂ (2 mg, 8.91 μmol) was added, degassed for 5 min and mixture was heated at 80° C. for 5 h. The reaction mixture was diluted with EtOAc, washed with water, brine, dried (MgSO₄) and concentrated to dryness. The residue was dissolved in EtOH (2 ml), NaOH (3.80 mg, 0.095 mmol) was added and heated in a sealed vial at 80° C. for 3 h. The mixture was cooled, filtered, purified by prep-HPLC to afford (S)-2-(tert-butoxy)-2-(4-(4,4-difluorochroman-6-yl)-5-(4-(4-fluorophenethoxy)phenyl)-2,6-dimethylpyridin-3-yl)acetic acid (0.0514 g, 0.080 mmol, 85% yield). LCMS (M+H)=620.1.

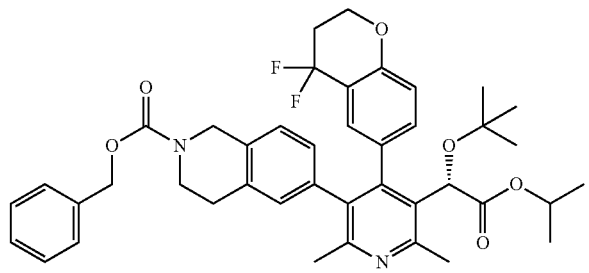 [SMILES: Cc1nc(C)c([C@H](OC(C)(C)C)C(=O)OC(C)C)c(-c2ccc3c(c2)C(F)(F)CCO3)c1-c1ccc2c(c1)CCN(C(=O)OCc1ccccc1)C2]

(S)-Benzyl 6-(5-(1-(tert-butoxy)-2-isopropoxy-2-oxoethyl)-4-(4,4-difluorochroman-6-yl)-2,6-dimethylpyridin-3-yl)-3,4-dihydroisoquinoline-2(1H)-carboxylate A mixture of (S)-isopropyl 2-(5-bromo-4-(4,4-difluorochroman-6-yl)-2,6-dimethylpyridin-3-yl)-2-(tert-butoxy)acetate (0.26 g, 0.494 mmol), (2-((benzyloxy)carbonyl)-1,2,3,4-tetrahydroisoquinolin-6-yl)boronic acid (0.2 g, 0.643 mmol) and 2M $Na_2CO_3$ (2 mL, 4.00 mmol) in 1,4-dioxane (4 mL) was degassed for 10 min. Then, $Pd(Ph_3P)_4$ (0.06 g, 0.052 mmol) was added, degassed for 5 min and heated at 85° C. for 18 h. The reaction mixture was cooled, diluted with EtOAc and washed with water, brine, dried ($MgSO_4$), concentrated and purified via Biotage 80 g column (EtOAc/hexanes: 0 to 50%) to afford (S)-benzyl 6-(5-(1-(tert-butoxy)-2-isopropoxy-2-oxoethyl)-4-(4,4-difluorochroman-6-yl)-2,6-dimethylpyridin-3-yl)-3,4-dihydroisoquinoline-2(1H)-carboxylate (0.24 g, 0.337 mmol, 68.2% yield). LCMS (M+H)=713.4.

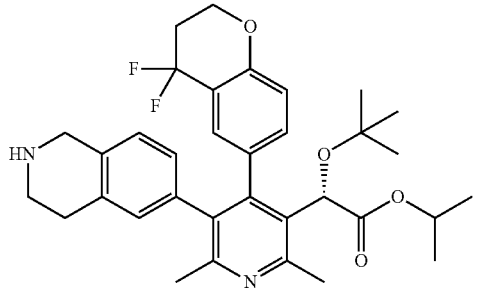 [SMILES: Cc1nc(C)c([C@H](OC(C)(C)C)C(=O)OC(C)C)c(-c2ccc3c(c2)C(F)(F)CCO3)c1-c1ccc2c(c1)CCNC2]

(S)-Isopropyl 2-(tert-butoxy)-2-(4-(4,4-difluorochroman-6-yl)-2,6-dimethyl-5-(1,2,3,4-tetrahydroisoquinolin-6-yl)pyridin-3-yl)acetate A solution of (S)-benzyl 6-(5-(1-(tert-butoxy)-2-isopropoxy-2-oxoethyl)-4-(4,4-difluorochroman-6-yl)-2,6-dimethylpyridin-3-yl)-3,4-dihydroisoquinoline-2(1H)-carboxylate (0.24 g, 0.337 mmol) in ethyl acetate (15 mL) was degassed and purged with N2. 10% Pd/C (0.05 g, 0.047 mmol) was added and degassed and refilled with $H_2$. The reaction mixture was stirred under $H_2$ balloon pressure for 2 h. Filtered off the solid and concentrated to dryness to afford (S)-isopropyl 2-(tert-butoxy)-2-(4-(4,4-difluorochroman-6-yl)-2,6-dimethyl-5-(1,2,3,4-tetrahydroisoquinolin-6-yl)pyridin-3-yl)acetate (0.152 g, 0.263 mmol, 78% yield) as a grey solid. LCMS (M+H)=579.4.

Example 37

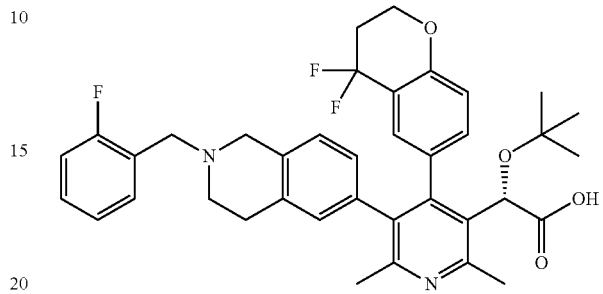

(S)-2-(tert-Butoxy)-2-(4-(4,4-difluorochroman-6-yl)-5-(2-(2-fluorobenzyl)-1,2,3,4-tetrahydroisoquinolin-6-yl)-2,6-dimethylpyridin-3-yl)acetic Acid A solution of (S)-isopropyl 2-(tert-butoxy)-2-(4-(4,4-difluorochroman-6-yl)-2,6-dimethyl-5-(1,2,3,4-tetrahydroisoquinolin-6-yl)pyridin-3-yl)acetate (0.025 g, 0.043 mmol) and 2-fluorobenzaldehyde (0.008 g, 0.064 mmol) in EtOH (1 mL) was stirred for 2 h at rt. $NaBH(OAc)_3$ (0.02 g, 0.094 mmol) was added and the mixture was stirred at rt for 1 h. Then, added sodium hydroxide (0.04 g, 1.000 mmol) and heated at 85° C. in a sealed vial for 4 h, cooled and purified by prep HPLC to afford (S)-2-(tert-butoxy)-2-(4-(4,4-difluorochroman-6-yl)-5-(2-(2-fluorobenzyl)-1,2,3,4-tetrahydroisoquinolin-6-yl)-2,6-dimethylpyridin-3-yl)acetic acid (0.0186 g, 0.028 mmol, 65.4% yield). LCMS (M+H)=645.1.

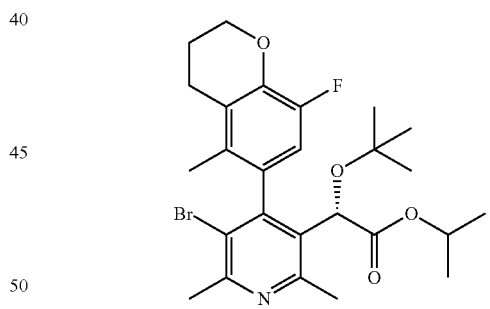

(2S)-Isopropyl 2-(5-bromo-4-(8-fluoro-5-methylchroman-6-yl)-2,6-dimethylpyridin-3-yl)-2-(tert-butoxy)acetate A mixture of (S)-isopropyl 2-(5-bromo-4-iodo-2,6-dimethylpyridin-3-yl)-2-(tert-butoxy)acetate (1.5 g, 3.10 mmol), (8-fluoro-5-methylisochroman-6-yl)boronic acid (0.66 g, 3.14 mmol) and 2M $Na_2CO_3$ (5 mL, 10.00 mmol) in DMF (15 mL) was degassed for 10 min. Then, $PdCl_2$(dppf)-$CH_2Cl_2$ adduct (0.14 g, 0.171 mmol) was added, and degassed for 5 min. The reaction mixture was placed in a pre-heated oil bath 60° C. for 18 h. Then, reaction mixture was cooled and diluted with EtOAc washed with water, brine, dried ($MgSO_4$) concentrated and purified by ISCO 12 g column (EtOAc/Hex: 0 to 20%) to afford (2S)-isopropyl 2-(5-bromo-4-(8-fluoro-5-methylchroman-6-yl)-2,6-dimethylpyridin-3-yl)-2-(tert-butoxy)acetate (0.98 g, 1.876 mmol, 60.5% yield. ¹H NMR (500 MHz, CDCl₃) δ 6.61 (d, J=11.0 Hz, 1H), 5.03-4.93 (m, 1H), 4.86 (s, 1H), 4.35-4.27 (m, 2H), 2.75-2.71 (m, 2H), 2.70-2.69 (m, 3H), 2.67 (s, 3H), 2.17-2.12 (m, 2H), 1.85 (s, 3H), 1.19 (d, J=6.3 Hz, 3H), 1.15 (d, J=6.1 Hz, 3H), 1.11 (s, 9H).). LCMS (M+H)=524.3.

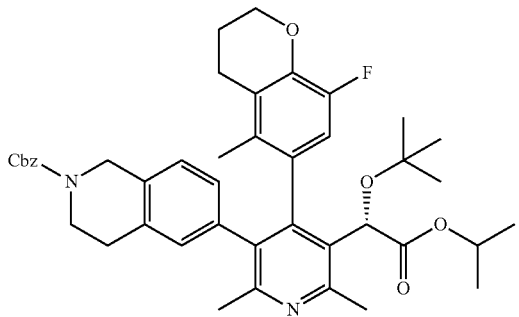 [SMILES: Cc1nc(C)c([C@H](OC(C)(C)C)C(=O)OC(C)C)c(-c2cc(F)c3c(c2C)CCCO3)c1-c1ccc2c(c1)CCN(C(=O)OCc1ccccc1)C2]

Benzyl 6-(5-((S)-1-(tert-butoxy)-2-isopropoxy-2-oxoethyl)-4-(8-fluoro-5-methylchroman-6-yl)-2,6-dimethylpyridin-3-yl)-3,4-dihydroisoquinoline-2(1H)-carboxylate A mixture of (2S)-isopropyl 2-(5-bromo-4-(8-fluoro-5-methylchroman-6-yl)-2,6-dimethylpyridin-3-yl)-2-(tert-butoxy)acetate (0.56 g, 1.072 mmol), (2-((benzyloxy)carbonyl)-1,2,3,4-tetrahydroisoquinolin-6-yl)boronic acid (0.45 g, 1.446 mmol) and 2M Na₂CO₃ (3.5 mL, 7.00 mmol) in 1,4-dioxane (5 mL) was degassed for 10 min. Then, Pd(PPh₃)₄ (0.07 g, 0.061 mmol) was added, degassed for 5 min and heated at 85° C. for 18 h. The reaction mixture was cooled, diluted with EtOAc, washed with water, brine, dried (MgSO₄), concentrated and purified via Biotage 80 g column (EtOAc/hexanes: 0 to 50%) to afford benzyl 6-(5-((S)-1-(tert-butoxy)-2-isopropoxy-2-oxoethyl)-4-(8-fluoro-5-methylchroman-6-yl)-2,6-dimethylpyridin-3-yl)-3,4-dihydroisoquinoline-2(1H)-carboxylate (0.43 g, 0.607 mmol, 56.6% yield). LCMS (M+H)=709.5.

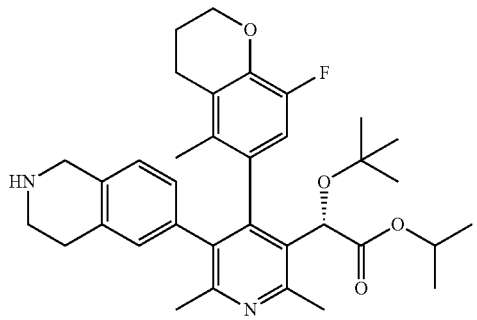 [SMILES: Cc1nc(C)c([C@H](OC(C)(C)C)C(=O)OC(C)C)c(-c2cc(F)c3c(c2C)CCCO3)c1-c1ccc2c(c1)CCNC2]

(2S)-Isopropyl 2-(tert-butoxy)-2-(4-(8-fluoro-5-methylchroman-6-yl)-2,6-dimethyl-5-(1,2,3,4-tetrahydroisoquinolin-6-yl)pyridin-3-yl)acetate A solution of benzyl 6-(5-((S)-1-(tert-butoxy)-2-isopropoxy-2-oxoethyl)-4-(8-fluoro-5-methylchroman-6-yl)-2,6-dimethylpyridin-3-yl)-3,4-dihydroisoquinoline-2(1H)-carboxylate (0.43 g, 0.607 mmol) in EtOH (15 mL) was degassed and purged with N₂. 10% Pd/C (0.065 g, 0.061 mmol) was added and degassed and refilled with H₂. The reaction mixture was stirred under H₂ balloon pressure for 2 h. Then, filtered off the solid, concentrated and purified by Prep HPLC to afford (2S)-isopropyl 2-(tert-butoxy)-2-(4-(8-fluoro-5-methylchroman-6-yl)-2,6-dimethyl-5-(1,2,3,4-tetrahydroisoquinolin-6-yl)pyridin-3-yl)acetate (0.25 g, 0.435 mmol, 71.7% yield). LCMS (M+H)=575.6.

Example 38

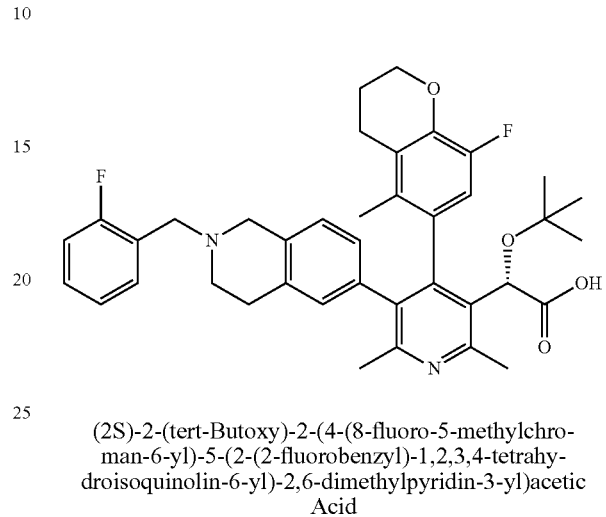

(2S)-2-(tert-Butoxy)-2-(4-(8-fluoro-5-methylchroman-6-yl)-5-(2-(2-fluorobenzyl)-1,2,3,4-tetrahydroisoquinolin-6-yl)-2,6-dimethylpyridin-3-yl)acetic Acid To a solution of (2S)-isopropyl 2-(tert-butoxy)-2-(4-(8-fluoro-5-methylchroman-6-yl)-2,6-dimethyl-5-(1,2,3,4-tetrahydroisoquinolin-6-yl)pyridin-3-yl)acetate (0.06 g, 0.104 mmol) in EtOH (1 mL) was added 2-fluorobenzaldehyde (0.03 g, 0.242 mmol). The mixture was stirred at rt for 2 h and NaBH(OAc)₃ (0.05 g, 0.236 mmol) was added. After 18 h, the reaction was treated with sodium hydroxide (0.05 g, 1.250 mmol) added and stirred at 85° C. in a sealed vial for 2 h. Then, filtered and purified by prep-HPLC to afford (2S)-2-(tert-butoxy)-2-(4-(8-fluoro-5-methylchroman-6-yl)-5-(2-(2-fluorobenzyl)-1,2,3,4-tetrahydroisoquinolin-6-yl)-2,6-dimethylpyridin-3-yl)acetic acid (0.0459 g, 0.072 mmol, 68.6% yield). LCMS (M+H)=641.2.

Example 39

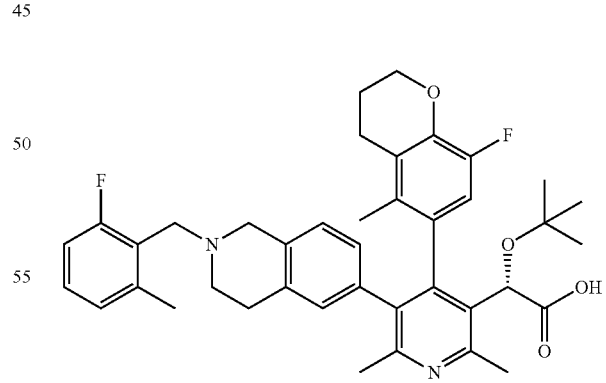

(2S)-2-(tert-Butoxy)-2-(4-(8-fluoro-5-methylchroman-6-yl)-5-(2-(2-fluoro-6-methylbenzyl)-1,2,3,4-tetrahydroisoquinolin-6-yl)-2,6-dimethylpyridin-3-yl)acetic Acid To a solution of (2S)-isopropyl 2-(tert-butoxy)-2-(4-(5-fluoro-8-methylchroman-6-yl)-2,6-dimethyl-5-(1,2,3,4-tetrahydroisoquinolin-6-yl)pyridin-3-yl)acetate (0.06 g, 0.104 mmol) in EtOH (1 mL) was added 2-fluoro-6-methylbenzaldehyde (0.03 g, 0.217 mmol) and stirred at rt for 2 h. NaBH(OAc)₃ (0.05 g, 0.236 mmol) was added to the mixture and stirred at rt for 18 h. Then sodium hydroxide (0.05 g, 1.250 mmol) was added and heated at 85° C. in a sealed vial for 18 h. Cooled, neutralized with HOAc, filtered and purified by prep-HPLC to afford (2S)-2-(tert-butoxy)-2-(4-(8-fluoro-5-methylchroman-6-yl)-5-(2-(2-fluoro-6-methylbenzyl)-1,2,3,4-tetrahydroisoquinolin-6-yl)-2,6-dimethylpyridin-3-yl)acetic acid (0.0289 g, 0.044 mmol, 41.9% yield). LC-MS (M+H=655.1.

Example 40

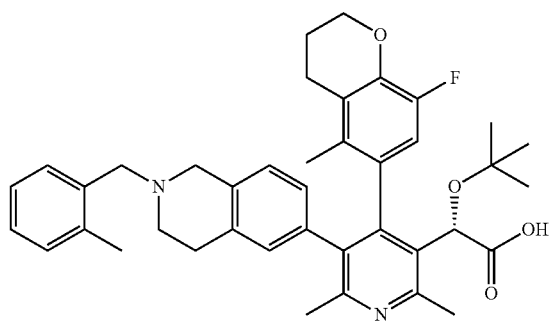 [SMILES: Cc1ccccc1CN1CCc2cc(-c3c(C)nc(C)c([C@H](OC(C)(C)C)C(=O)O)c3-c3cc(F)c4c(c3C)CCCO4)ccc2C1]

(2S)-2-(tert-Butoxy)-2-(4-(8-fluoro-5-methylchroman-6-yl)-2,6-dimethyl-5-(2-(2-methylbenzyl)-1,2,3,4-tetrahydroisoquinolin-6-yl)pyridin-3-yl)acetic Acid To a solution of (2S)-isopropyl 2-(tert-butoxy)-2-(4-(5-fluoro-8-methylchroman-6-yl)-2,6-dimethyl-5-(1,2,3,4-tetrahydroisoquinolin-6-yl)pyridin-3-yl)acetate (0.06 g, 0.104 mmol) in EtOH (1 mL) was added 2-methylbenzaldehyde (0.03 g, 0.250 mmol) and resulting mixture was stirred at rt for 1 h. Then, NaBH(OAc)₃ (0.05 g, 0.236 mmol) was added and stirred at rt for 1.5 h. To this, sodium hydroxide (0.09 g, 2.250 mmol) was added heated at 90° C. in a sealed vial for 3 h, cooled, filtered and purified by prep-HPLC to afford (2S)-2-(tert-butoxy)-2-(4-(8-fluoro-5-methylchroman-6-yl)-2,6-dimethyl-5-(2-(2-methylbenzyl)-1,2,3,4-tetrahydroisoquinolin-6-yl)pyridin-3-yl)acetic acid (0.0289 g, 0.044 mmol, 42.2% yield). LCMS (M+H)=637.1.

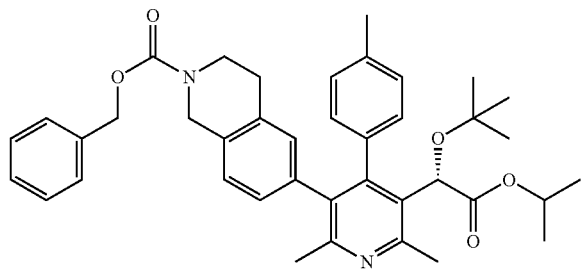 [SMILES: Cc1ccc(-c2c(-c3ccc4c(c3)CCN(C(=O)OCc3ccccc3)C4)c(C)nc(C)c2[C@H](OC(C)(C)C)C(=O)OC(C)C)cc1]

(S)-Benzyl 6-(5-(1-(tert-butoxy)-2-isopropoxy-2-oxoethyl)-2,6-dimethyl-4-(p-tolyl)pyridin-3-yl)-3,4-dihydroisoquinoline-2(1H)-carboxylate A mixture of (S)-isopropyl 2-(5-bromo-4-iodo-2,6-dimethylpyridin-3-yl)-2-(tert-butoxy)acetate (0.3 g, 0.620 mmol), p-tolylboronic acid (0.084 g, 0.620 mmol) and 2M Na₂CO₃ (2 mL, 4.00 mmol) in dioxane (4 mL) was degassed for 10 min. Then, Pd(Ph₃P)₄ (0.07 g, 0.061 mmol) was added, degassed for 5 min and placed in a pre-heated oil bath at 80° C. for 4 h. The reaction mixture was cooled and (2-((benzyloxy)carbonyl)-1,2,3,4-tetrahydroisoquinolin-6-yl)boronic acid (0.193 g, 0.620 mmol), Pd(Ph₃P)₄ (0.07 g, 0.061 mmol), 2M Na₂CO₃ (2 mL, 4.00 mmol) were added. Then, the mixture was stirred at 80° C. overnight. The reaction mixture was cooled and diluted with EtOAc, washed with water, brine, dried (MgSO₄), concentrated and purified by ISCO 40 g column (EtOAc/Hex: 0 to 50%) to afford (S)-benzyl 6-(5-(1-(tert-butoxy)-2-isopropoxy-2-oxoethyl)-2,6-dimethyl-4-(p-tolyl)pyridin-3-yl)-3,4-dihydroisoquinoline-2(1H)-carboxylate (0.17 g, 0.268 mmol, 43.2% yield). ¹H NMR (400 MHz, CDCl3) δ 7.48-7.31 (m, 5H), 7.18 (d, J=6.8 Hz, 1H), 7.05 (d, J=7.5 Hz, 1H), 6.98 (br. s., 1H), 6.94-6.76 (m, 2H), 6.73-6.62 (m, 1H), 6.57-6.41 (m, J=9.3 Hz, 1H), 5.25-5.14 (m, J=3.0 Hz, 2H), 5.07 (dt, J=13.0, 6.7 Hz, 1H), 4.94 (2s., 1H), 4.65-4.44 (m, J=9.8 Hz, 2H), 3.87-3.53 (m, J=19.3 Hz, 2H), 2.83 (s, 1H), 2.68 (s, 3H), 2.63-2.43 (m, 1H), 2.32 (s, 3H), 2.27 (br. s., 3H), 1.33-1.19 (m, 6H), 0.95 (s, 9H). LCMS (M+H)=635.6.

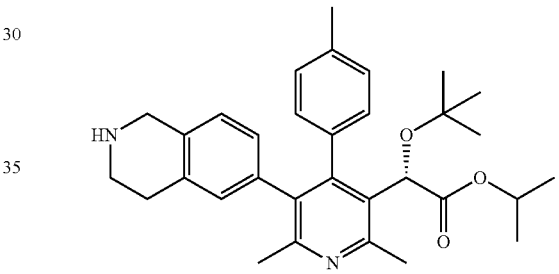

(S)-Isopropyl 2-(tert-butoxy)-2-(2,6-dimethyl-5-(1,2,3,4-tetrahydroisoquinolin-6-yl)-4-(p-tolyl)pyridin-3-yl)acetate A solution of (S)-benzyl 6-(5-(1-(tert-butoxy)-2-isopropoxy-2-oxoethyl)-2,6-dimethyl-4-(p-tolyl)pyridin-3-yl)-3,4-dihydroisoquinoline-2(1H)-carboxylate (0.17 g, 0.268 mmol) in THF (10 mL) was degassed and purged with N₂. 10% Pd/C (0.011 g, 10.71 μmol) was added and degassed and refilled with H₂. The reaction mixture was stirred under H₂ balloon pressure for 10 h. Then, filtered off the solid and concentrated to dryness to afford (S)-isopropyl 2-(tert-butoxy)-2-(2,6-dimethyl-5-(1,2,3,4-tetrahydroisoquinolin-6-yl)-4-(p-tolyl)pyridin-3-yl)acetate (0.134 g, 0.268 mmol, 100% yield) as a grey solid. ¹H NMR (500 MHz, CDCl₃) δ 7.22-7.16 (m, 1H), 7.08-7.03 (m, 1H), 6.94-6.85 (m, 2H), 6.74-6.68 (m, 1H), 6.51-6.41 (m, 1H), 5.13-5.04 (m, 1H), 4.94 (2s, 1H), 4.01-3.84 (m, 2H), 3.19-3.00 (m, 2H), 2.77 (t, J=5.6 Hz, 1H), 2.69 (s, 3H), 2.63-2.43 (m, 1H), 2.33 (s, 3H), 2.29 (s, 3H), 1.34-1.28 (m, 4H), 1.25 (dd, J=6.1, 3.6 Hz, 3H), 0.96 (s, 9H). LCMS (M+H)=501.4.

Example 41

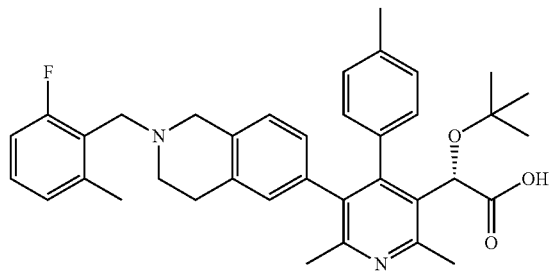 [SMILES: Cc1ccc(-c2c(-c3ccc4c(c3)CCN(Cc3c(C)cccc3F)C4)c(C)nc(C)c2[C@H](OC(C)(C)C)C(=O)O)cc1]

(S)-2-(tert-Butoxy)-2-(5-(2-(2-fluoro-6-methylbenzyl)-1,2,3,4-tetrahydroisoquinolin-6-yl)-2,6-dimethyl-4-(p-tolyl)pyridin-3-yl)acetic Acid To a solution of (S)-isopropyl 2-(tert-butoxy)-2-(2,6-dimethyl-5-(1,2,3,4-tetrahydroisoquinolin-6-yl)-4-(p-tolyl)pyridin-3-yl)acetate (0.03 g, 0.060 mmol) in EtOH (1 mL) was added 2-fluoro-6-methylbenzaldehyde (0.012 g, 0.090 mmol) and stirred at rt for 1 h. Then, NaBH(OAc)$_3$ (0.03 g, 0.142 mmol) was added and stirred at rt for 20 h. Additional NaBH(OAc)$_3$ (0.03 g, 0.142 mmol) was added and stirred at rt for 2 h. Then, sodium hydroxide (0.06 g, 1.500 mmol) was added and heated at 85° C. in a sealed vial for 3 h, cooled, filtered and purified by prep HPLC to afford (S)-2-(tert-butoxy)-2-(5-(2-(2-fluoro-6-methylbenzyl)-1,2,3,4-tetrahydroisoquinolin-6-yl)-2,6-dimethyl-4-(p-tolyl)pyridin-3-yl)acetic acid (0.0246 g, 0.042 mmol, 70.7% yield). $^1$H NMR (500 MHz, DMSO-d$_6$) δ 7.27-7.19 (m, 2H), 7.13 (br. s., 1H), 7.06-6.98 (m, 3H), 6.96-6.87 (m, 2H), 6.77-6.67 (m, 1H), 6.45-6.38 (m, 1H), 4.78 (2s, 1H), 3.59 (d, J=10.3 Hz, 2H), 3.48 (br. s., 2H), 3.36 (br. s., 2H), 2.66 (d, J=12.8 Hz, 1H), 2.57 (d, J=10.6 Hz, 1H), 2.52 (br. s., 3H), 2.38 (d, J=8.8 Hz, 3H), 2.22 (s, 3H), 2.15 (s, 3H), 0.84 (s, 9H). LCMS (M+H)=581.3.

Example 42

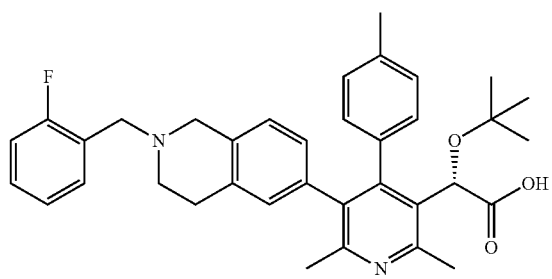 [SMILES: Cc1ccc(-c2c(-c3ccc4c(c3)CCN(Cc3ccccc3F)C4)c(C)nc(C)c2[C@H](OC(C)(C)C)C(=O)O)cc1]

(S)-2-(tert-Butoxy)-2-(5-(2-(2-fluorobenzyl)-1,2,3,4-tetrahydroisoquinolin-6-yl)-2,6-dimethyl-4-(p-tolyl)pyridin-3-yl)acetic Acid To a solution of (S)-isopropyl 2-(tert-butoxy)-2-(2,6-dimethyl-5-(1,2,3,4-tetrahydroisoquinolin-6-yl)-4-(p-tolyl)pyridin-3-yl)acetate (0.03 g, 0.060 mmol) in EtOH (1 mL) was added 2-fluorobenzaldehyde (0.011 g, 0.090 mmol). The mixture was stirred at rt for 1 h and NaB(OAc)$_3$H (0.03 g, 0.142 mmol) was added. The mixture was stirred at rt for 20 h and added sodium hydroxide (0.06 g, 1.500 mmol). The mixture was heated at 85° C. in a sealed vial for 3 h, filtered and purified by prep HPLC to afford (S)-2-(tert-butoxy)-2-(5-(2-(2-fluorobenzyl)-1,2,3,4-tetrahydroisoquinolin-6-yl)-2,6-dimethyl-4-(p-tolyl)pyridin-3-yl)acetic acid (0.0384 g). $^1$H NMR (500 MHz, DMSO-d6) δ 7.50-7.39 (m, J=8.1 Hz, 1H), 7.33 (br. s., 1H), 7.27 (br. s., 1H), 7.22-7.16 (m, 2H), 7.16-7.08 (m, 1H), 7.04-6.98 (m, 1H), 6.98-6.89 (m, 1H), 6.73 (br. s., 1H), 6.48-6.38 (m, 1H), 4.77 (2s, 1H), 3.66 (d, J=9.9 Hz, 2H), 3.56-3.44 (m, 5H), 2.80-2.75 (m, 1H), 2.66-2.59 (m, 1H), 2.53 (s, 3H), 2.23 (s, 3H), 2.15 (s, 3H), 0.84 (s, 9H). LCMS (M+H)=567.2.

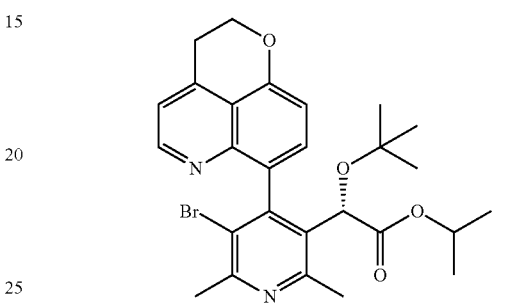

(2S)-Isopropyl 2-(5-bromo-4-(2,3-dihydropyrano[4,3,2-de]quinolin-7-yl)-2,6-dimethylpyridin-3-yl)-2-(tert-butoxy)acetate A mixture of (S)-isopropyl 2-(5-bromo-4-iodo-2,6-dimethylpyridin-3-yl)-2-(tert-butoxy)acetate (0.2 g, 0.413 mmol), 2-(2,3-dihydropyrano[4,3,2-de]quinolin-7-yl)-6-methyl-1,3,6,2-dioxazaborocane-4,8-dione (0.135 g, 0.413 mmol), 2-dicyclohexylphosphino-2',6'-dimethoxybiphenyl (15 mg, 0.037 mmol), water (0.4 mL) and 2M K$_3$PO$_4$ (1.5 mL, 3.00 mmol) in 1,4-dioxane (2 mL) was degassed for 10 min. Then, Pd(OAc)$_2$ (4 mg, 0.018 mmol) was added, degassed for 5 min and mixture was heated at 65° C. for 18 h. The reaction mixture was diluted with EtOAc and washed with water, brine, dried (MgSO$_4$), concentrated and purified by prep HPLC to afford (2S)-Isopropyl 2-(5-bromo-4-(2,3-dihydropyrano[4,3,2-de]quinolin-7-yl)-2,6-dimethylpyridin-3-yl)-2-(tert-butoxy)acetate (0.036 g, 0.068 mmol, 16.52% yield). LC-MS (M+H)=529.3.

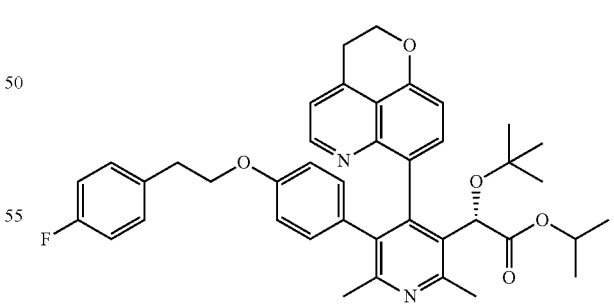

(2S)-Isopropyl 2-(tert-butoxy)-2-(4-(2,3-dihydropyrano[4,3,2-de]quinolin-7-yl)-5-(4-(4-fluorophenethoxy)phenyl)-2,6-dimethylpyridin-3-yl)acetate A mixture of (2S)-isopropyl 2-(5-bromo-4-(2,3-dihydropyrano[4,3,2-de]quinolin-7-yl)-2,6-dimethylpyridin-3-yl)-

2-(tert-butoxy)acetate (0.036 g, 0.068 mmol), 2-(4-(4-fluorophenethoxy)phenyl)-6-methyl-1,3,6,2-dioxazaborocane-4,8-dione (0.1 g, 0.269 mmol), 2-dicyclohexylphosphino-2',6'-dimethoxybiphenyl (6 mg, 0.015 mmol), water (0.5 mL) and 2M K$_3$PO$_4$ (0.5 mL, 1.000 mmol) in 1,4-dioxane (1 mL) was degassed for 5 min. Then, Pd(OAc)$_2$ (1 mg, 4.45 μmol) was added, degassed for 5 min and heated at 80° C. for 18 h. The reaction mixture was diluted with EtOAc and washed with water, brine and purified on ISCO 12 g column (EtOAc/hexanes: 0 to 50%) to afford (2S)-isopropyl 2-(tert-butoxy)-2-(4-(2,3-dihydropyrano[4,3,2-de]quinolin-7-yl)-5-(4-(4-fluorophenethoxy)phenyl)-2,6-dimethylpyridin-3-yl)acetate (0.012 g, 0.018 mmol, 26.5% yield) as a solid. $^1$H NMR (500 MHz, CDCl3) δ 8.69 (d, J=4.4 Hz, 1H), 7.49 (d, J=7.9 Hz, 1H), 7.19-7.11 (m, 2H), 7.01-6.95 (m, 4H), 6.88 (d, J=8.0 Hz, 1H), 6.71 (dd, J=8.4, 2.1 Hz, 1H), 6.51 (dd, J=8.4, 2.6 Hz, 1H), 6.38 (dd, J=8.5, 2.7 Hz, 1H), 5.08-4.97 (m, 1H), 4.81 (s, 1H), 4.46-4.33 (m, 2H), 3.99-3.92 (m, 2H), 3.20-3.12 (m, 2H), 2.94 (t, J=6.9 Hz, 2H), 2.78 (s, 3H), 2.31 (s, 3H), 1.28 (d, J=6.1 Hz, 3H), 1.24 (d, J=6.3 Hz, 3H), 0.75 (s, 9H). LCMS (M+H)=663.5.

Example 43

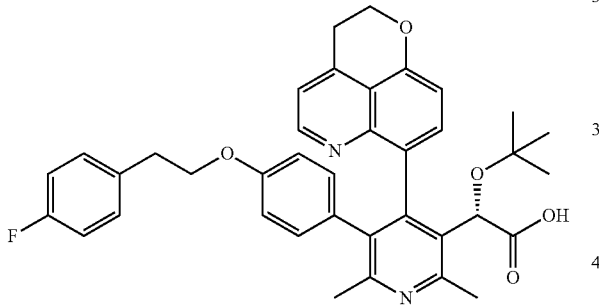

(2S)-2-(tert-Butoxy)-2-(4-(2,3-dihydropyrano[4,3,2-de]quinolin-7-yl)-5-(4-(4-fluorophenethoxy)phenyl)-2,6-dimethylpyridin-3-yl)acetic Acid To a solution of (2S)-isopropyl 2-(tert-butoxy)-2-(4-(2,3-dihydropyrano[4,3,2-de]quinolin-7-yl)-5-(4-(4-fluorophenethoxy)phenyl)-2,6-dimethylpyridin-3-yl)acetate (12 mg, 0.018 mmol) in EtOH (1 mL) was added sodium hydroxide (25 mg, 0.625 mmol). The mixture was stirred at 85° C. in a sealed tube for 2 h, then cooled and purified by pre-HPLC to afford (2S)-2-(tert-butoxy)-2-(4-(2,3-dihydropyrano[4,3,2-de]quinolin-7-yl)-5-(4-(4-fluorophenethoxy)phenyl)-2,6-dimethylpyridin-3-yl)acetic acid (0.005 g, 8.06 μmol, 44.5% yield). $^1$H NMR (500 MHz, DMSO-d6) δ 8.63 (d, J=4.0 Hz, 1H), 7.46 (d, J=8.1 Hz, 1H), 7.25-7.21 (m, 2H), 7.16 (d, J=4.0 Hz, 1H), 7.08 (t, J=8.8 Hz, 2H), 6.93 (d, J=7.7 Hz, 1H), 6.86 (d, J=8.4 Hz, 1H), 6.72 (d, J=8.4 Hz, 1H), 6.54 (d, J=7.7 Hz, 1H), 6.42 (d, J=7.7 Hz, 1H), 4.66 (s, 1H), 4.34-4.22 (m, 2H), 3.95 (br. s., 2H), 3.21-3.07 (m, 2H), 2.85 (t, J=6.6 Hz, 2H), 2.59 (s, 3H), 2.15 (s, 3H), 0.61 (s, 9H). LCMS (M+H)=621.1.

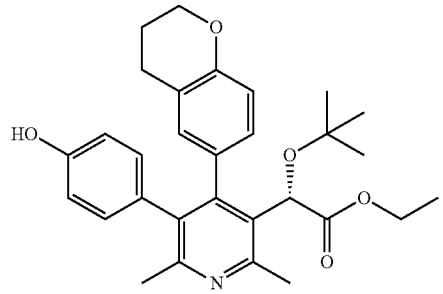 [SMILES: CCOC(=O)[C@@H](OC(C)(C)C)c1c(C)nc(C)c(-c2ccc(O)cc2)c1-c1ccc2c(c1)CCCO2]

(S)-Ethyl 2-(tert-butoxy)-2-(4-(chroman-6-yl)-5-(4-hydroxyphenyl)-2,6-dimethylpyridin-3-yl)acetate A mixture of (S)-ethyl 2-(5-bromo-4-(chroman-6-yl)-2,6-dimethylpyridin-3-yl)-2-(tert-butoxy)acetate (0.17 g, 0.357 mmol), (4-hydroxyphenyl)boronic acid (0.08 g, 0.580 mmol), Na$_2$CO$_3$ (1 mL, 2.000 mmol), 1,4-dioxane (1.5 mL) and was charged in a seal vial, degassed for 10 min. Then, Pd(Ph$_3$P)$_4$ (0.05 g, 0.043 mmol) was added, degassed for 5 min and mixture was heated at 85° C. for 20 h. The reaction mixture was cooled and diluted with EtOAc, washed with water, brine, dried (MgSO$_4$), concentrated and purified on a ISCO 40 g column (EtOAc/hexanes: 0 to 60%) to afford (S)-ethyl 2-(tert-butoxy)-2-(4-(chroman-6-yl)-5-(4-hydroxyphenyl)-2,6-dimethylpyridin-3-yl)acetate (0.16 g, 0.327 mmol, 92% yield) as a beige solid. LCMS (M+H)=488.2.

Example 44

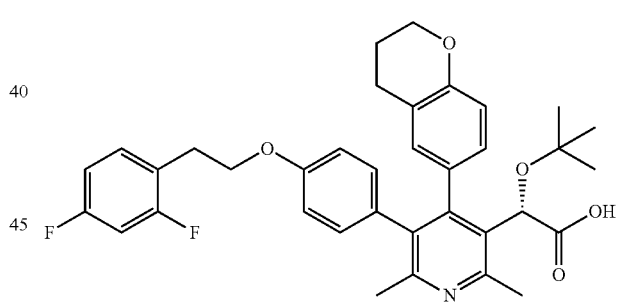

(S)-2-(tert-Butoxy)-2-(4-(chroman-6-yl)-5-(4-(2,4-difluorophenethoxy)phenyl)-2,6-dimethylpyridin-3-yl)acetic Acid To a stirred solution of (S)-ethyl 2-(tert-butoxy)-2-(4-(chroman-6-yl)-5-(4-hydroxyphenyl)-2,6-dimethylpyridin-3-yl)acetate (0.025 g, 0.051 mmol), 2-(2,4-difluorophenyl)ethanol (0.040 g, 0.255 mmol) and Ph$_3$P-resin (0.067 g, 0.255 mmol) in THF (2 mL) was added DIAD/toluene (0.124 mL, 0.255 mmol) at rt. After 18 h, the mixture was filtered and concentrated. The resulting residue was dissolved in EtOH (1 mL), treated with NaOH (0.06 g, 1.500 mmol) and stirred at 85° C. for 16 h. Then, the mixture was cooled, filtered and purified by prep-HPLC to afford (S)-2-(tert-butoxy)-2-(4-(chroman-6-yl)-5-(4-(2,4-difluorophenethoxy)phenyl)-2,6-dimethylpyridin-3-yl)acetic acid (0.0117 g, 0.019 mmol, 36.6% yield). LCMS (M+H)=602.0.

Example 45

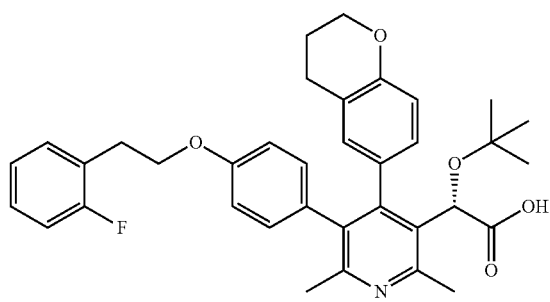 [SMILES: Cc1nc(C)c([C@H](OC(C)(C)C)C(=O)O)c(-c2ccc3c(c2)CCCO3)c1-c1ccc(OCCc2ccccc2F)cc1]

(S)-2-(tert-Butoxy)-2-(4-(chroman-6-yl)-5-(4-(2-fluorophenethoxy)phenyl)-2,6-dimethylpyridin-3-yl)acetic Acid To a stirred solution of (S)-ethyl 2-(tert-butoxy)-2-(4-(chroman-6-yl)-5-(4-hydroxyphenyl)-2,6-dimethylpyridin-3-yl)acetate (0.025 g, 0.051 mmol), 2-(2-fluorophenyl)ethanol (0.036 g, 0.255 mmol) and Ph$_3$P-resin (0.067 g, 0.255 mmol) in THF (2 mL) was added DIAD/toluene (0.14 mL, 0.265 mmol) at rt. After 18 h, mixture was filtered, concentrated and treated with 1N NaOH (0.854 mL, 0.854 mmol) in EtOH (1 mL) at 80° C. for 16 h. Mixture was cooled and purified by prep-HPLC to afford (S)-2-(tert-butoxy)-2-(4-(chroman-6-yl)-5-(4-(2-fluorophenethoxy)phenyl)-2,6-dimethylpyridin-3-yl)acetic acid (0.0056 g, 9.59 μmol, 18.79% yield). LCMS (M+H)=584.0.

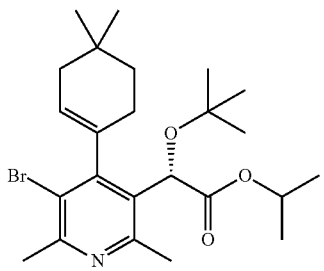 [SMILES: Cc1nc(C)c([C@H](OC(C)(C)C)C(=O)OC(C)C)c(C2=CCC(C)(C)CC2)c1Br]

(S)-Isopropyl 2-(5-bromo-4-(4,4-dimethylcyclohex-1-en-1-yl)-2,6-dimethylpyridin-3-yl)-2-(tert-butoxy)acetate A mixture of (S)-isopropyl 2-(5-bromo-4-iodo-2,6-dimethylpyridin-3-yl)-2-(tert-butoxy)acetate (1 g, 2.065 mmol), 2-(4,4-dimethylcyclohex-1-en-1-yl)-4,4,5,5-tetramethyl-1,3,2-dioxaborolane (0.63 g, 2.67 mmol) and 2M Na$_2$CO$_3$ (5 ml, 10 mmol) in dioxane (5 mL) was degassed for 10 min. Then, DPPF (0.1 g, 0.18 mmol) was added, degassed for 5 min and placed in a pre-heated oil bath 60° C. for 5 h. The reaction mixture was cooled and diluted with EtOAc washed with water, brine, dried (MgSO$_4$), concentrated and purified on silica gel chromatography (EtOAc/Hex: 0 to 20%) to afford (S)-isopropyl 2-(5-bromo-4-(4,4-dimethylcyclohex-1-en-1-yl)-2,6-dimethylpyridin-3-yl)-2-(tert-butoxy)acetate (0.6 g, 1.286 mmol, 62.3% yield). LCMS (M+H)=467.4.

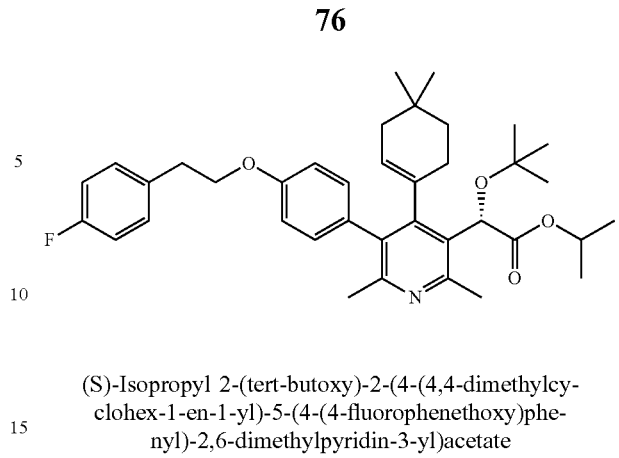

(S)-Isopropyl 2-(tert-butoxy)-2-(4-(4,4-dimethylcyclohex-1-en-1-yl)-5-(4-(4-fluorophenethoxy)phenyl)-2,6-dimethylpyridin-3-yl)acetate A mixture of (S)-isopropyl 2-(5-bromo-4-(4,4-dimethylcyclohex-1-en-1-yl)-2,6-dimethylpyridin-3-yl)-2-(tert-butoxy)acetate (0.1 g, 0.2 mmol), 2-(4-(4-fluorophenethoxy)phenyl)-6-methyl-1,3,6,2-dioxazaborocane-4,8-dione (0.1 g, 0.27 mmol), 2-dicyclohexylphosphino-2',6'-dimethoxybiphenyl (0.018 g, 0.043 mmol) and 2M K$_3$PO$_4$ (0.8 mL, 1.6 mmol) in 1,4-dioxane (2 mL) and water (0.4 mL) was degassed for 10 min. Then, Pd(OAc)$_2$ (5 mg, 0.022 mmol) was added, degassed for 5 min and mixture was heated at 80° C. for 3 h. After cooling to room temperature, water was added and the mixture was extracted with ethyl acetate, washed with brine, dried (Na$_2$SO$_4$), filtered and concentrated. The residue was then purified by Biotage 12 g column (EtOAc/hexane: 5-40%) to afford (S)-isopropyl 2-(tert-butoxy)-2-(4-(4,4-dimethylcyclohex-1-en-1-yl)-5-(4-(4-fluorophenethoxy)phenyl)-2,6-dimethylpyridin-3-yl)acetate (0.035 g, 0.058 mmol, 27% yield) as foam. LCMS (M+H)=602.4.

Example 46

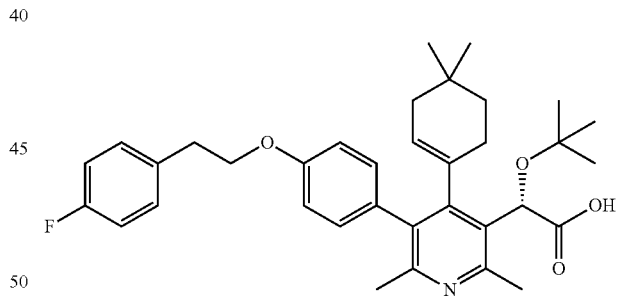

(S)-2-(tert-Butoxy)-2-(4-(4,4-dimethylcyclohex-1-en-1-yl)-5-(4-(4-fluorophenethoxy)phenyl)-2,6-dimethylpyridin-3-yl)acetic Acid A solution of (S)-isopropyl 2-(tert-butoxy)-2-(4-(4,4-dimethylcyclohex-1-en-1-yl)-5-(4-(4-fluorophenethoxy)phenyl)-2,6-dimethylpyridin-3-yl)acetate (0.035 g, 0.058 mmol) in EtOH (1 mL) was added sodium hydroxide (0.04 g, 1.0 mmol). The mixture was stirred at 85° C. for 4 h, cooled and purified by prep HPLC to afford (S)-2-(tert-butoxy)-2-(4-(4,4-dimethylcyclohex-1-en-1-yl)-5-(4-(4-fluorophenethoxy)phenyl)-2,6-dimethylpyridin-3-yl)acetic acid (0.0241 g, 0.043 mmol, 74.0% yield). LCMS (M+H)=560.2.

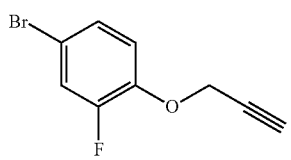

4-Bromo-2-fluoro-1-(prop-2-yn-1-yloxy)benzene

To a solution of 4-bromo-2-fluorophenol (5 g, 26.2 mmol) in DMF (40 mL) was added K₂CO₃ (10 g, 72.4 mmol) and 3-bromoprop-1-yne (3.2 mL, 28.7 mmol). The mixture was stirred at rt for 20 h and filtered off the solid. The filtrate was diluted with ether, washed with water, 1N NaOH, brine, dried (MgSO₄), concentrated to dryness to afford 4-bromo-2-fluoro-1-(prop-2-yn-1-yloxy)benzene (5.5 g, 24.01 mmol, 92% yield) as a brown liquid. ¹H NMR (500 MHz, CDCl₃) δ 7.32-7.27 (m, 1H), 7.25-7.22 (m, 1H), 7.02 (t, J=8.7 Hz, 1H), 4.77 (d, J=2.4 Hz, 2H), 2.57 (t, J=2.4 Hz, 1H).

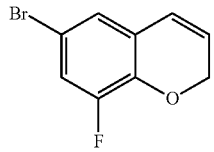 [SMILES: Fc1cc(Br)cc2c1OCC=C2]

6-Bromo-8-fluoro-2H-chromene

A solution of 4-bromo-2-fluoro-1-(prop-2-yn-1-yloxy) benzene (5.5 g, 24.01 mmol) in N,N-diethylaniline (50 mL) was heated at 210° C. for 20 h, cooled, diluted with hexane/ether and washed with ice chilled 2N HCl (4×), 1N NaOH, brine, dried (MgSO₄), filtered, concentrated and purified by ISCO 120 g cartridge to afford 6-bromo-8-fluoro-2H-chromene (2.4 g, 10.48 mmol, 43.6% yield) as brown liquid. ¹H NMR (500 MHz, CDCl₃) δ 7.11-7.06 (m, 1H), 6.91 (t, J=1.9 Hz, 1H), 6.39 (dq, J=10.1, 1.9 Hz, 1H), 5.89 (dt, J=10.0, 3.5 Hz, 1H), 4.92 (dd, J=3.5, 2.0 Hz, 2H).

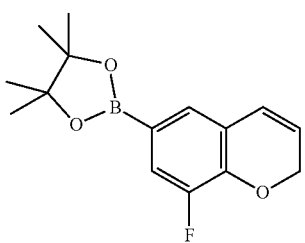 [SMILES: CC1(C)OB(c2cc(F)c3c(c2)C=CCO3)OC1(C)C]

2-(8-Fluoro-2H-chromen-6-yl)-4,4,5,5-tetramethyl-1,3,2-dioxaborolane

A mixture of 6-bromo-8-fluoro-2H-chromene (1.5 g, 6.55 mmol), potassium acetate (1.9 g, 19.6 mmol) and 4,4,4',4',5,5,5',5'-octamethyl-2,2'-bi(1,3,2-dioxaborolane) (3.2 g, 12.60 mmol) in dioxane (30 mL) was degassed for 5 min. Then, Pd(Ph₃P)₄ (0.378 g, 0.327 mmol) was added, degassed for 5 min and heated at 80° C. for 18 h. Then, diluted with EtOAc, washed water, brine, dried (MgSO₄), filtered, evaporated solvent and purified on Biotage 120 g column (0-30% EtOAc/Hex) to afford 2-(8-fluoro-2H-chromen-6-yl)-4,4,5,5-tetramethyl-1,3,2-dioxaborolane (1.4 g, 5.07 mmol, 77% yield) as colorless viscous oil. ¹H NMR (500 MHz, CDCl₃) δ 7.37 (dd, J=11.0, 1.3 Hz, 1H), 7.21 (s, 1H), 6.46 (dd, J=9.9, 1.9 Hz, 1H), 5.80 (dt, J=9.9, 3.5 Hz, 1H), 4.96 (dd, J=3.5, 2.0 Hz, 2H), 1.35 (s, 12H).

Example 47

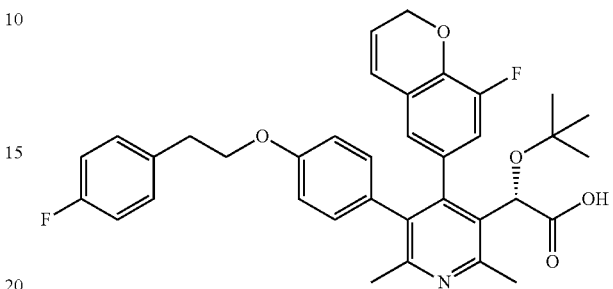

(S)-2-(tert-Butoxy)-2-(4-(8-fluoro-2H-chromen-6-yl)-5-(4-(4-fluorophenethoxy)phenyl)-2,6-dimethyl-pyridin-3-yl)acetic Acid A mixture of (S)-isopropyl 2-(5-bromo-4-iodo-2,6-dimethylpyridin-3-yl)-2-(tert-butoxy)acetate (0.06 g, 0.124 mmol), 2-(8-fluoro-2H-chromen-6-yl)-4,4,5,5-tetramethyl-1,3,2-dioxaborolane (0.036 g, 0.130 mmol) and 2M Na₂CO₃ (0.5 mL, 1 mmol) in dioxane (1 mL) was degassed for 5 min. Then, PdCl₂(dppf)-CH₂Cl₂ adduct (0.015 g, 0.018 mmol) was added, degassed for 5 min and placed in a pre-heated oil bath 60° C. for 3 h. The reaction mixture was cooled and added (4-(4-fluorophenethoxy)phenyl)boronic acid (0.05 g, 0.192 mmol) and stirred at 85° C. for 4 h. The reaction mixture was cooled down and extracted with EtOAc (2×). The combined organic solution was concentrated and treated with sodium hydroxide (0.1 g, 2.5 mmol) in EtOH (2 ml) at 85° C. for 2.5 h. Then, cooled and purified by prep HPLC to afford (S)-2-(tert-butoxy)-2-(4-(8-fluoro-2H-chromen-6-yl)-5-(4-(4-fluorophenethoxy)phenyl)-2,6-dimethylpyridin-3-yl)acetic acid (0.0026 g, 4.25 μmol, 3.43% yield). LCMS (M+H)=600.2.

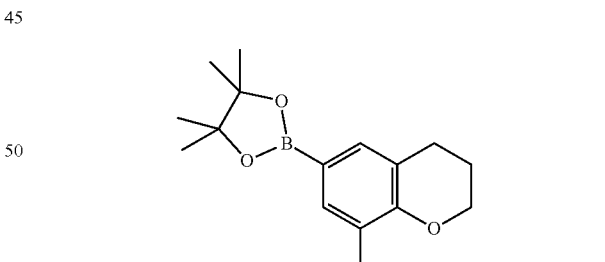

2-(8-Fluorochroman-6-yl)-4,4,5,5-tetramethyl-1,3,2-dioxaborolane

A solution of 2-(8-fluoro-2H-chromen-6-yl)-4,4,5,5-tetramethyl-1,3,2-dioxaborolane (0.8 g, 2.90 mmol) in MeOH (15 mL) was degassed and 10% Pd/C (0.2 g, 0.188 mmol) was added and degassed and filled with H₂. The reaction mixture was stirred under H₂ balloon pressure for 1 h, filtered off the solid and concentrated to dryness to afford 2-(8-fluorochroman-6-yl)-4,4,5,5-tetramethyl-1,3,2-dioxaborolane (0.806 g, 2.90 mmol, 100% yield) as a solid. ¹H NMR (500 MHz, CDCl₃) δ 7.42-7.31 (m, 2H), 4.32-4.27 (m, 2H), 2.83 (t, J=6.5 Hz, 2H), 2.08-2.02 (m, 2H), 1.35 (s, 12H).

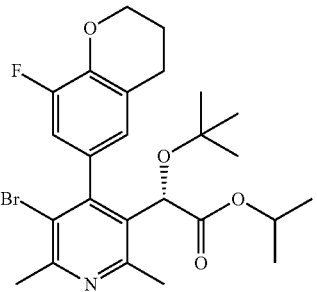 [SMILES: Cc1nc(C)c([C@H](OC(C)(C)C)C(=O)OC(C)C)c(-c2cc(F)c3c(c2)CCCO3)c1Br]

(S)-Isopropyl 2-(5-bromo-4-(8-fluorochroman-6-yl)-2,6-dimethylpyridin-3-yl)-2-(tert-butoxy)acetate A mixture of (S)-isopropyl 2-(5-bromo-4-iodo-2,6-dimethylpyridin-3-yl)-2-(tert-butoxy)acetate (1 g, 2.065 mmol), 2-(8-fluoroisochroman-6-yl)-4,4,5,5-tetramethyl-1,3,2-dioxaborolane (0.7 g, 2.52 mmol) and 2M Na₂CO₃ (3.6 mL, 7.20 mmol) in dioxane (8 mL) was degassed for 10 min. Then, PdCl₂(dppf)-CH₂Cl₂ adduct (0.169 g, 0.207 mmol) was added, degassed for 5 min and placed in a pre-heated oil bath 60° C. for 5 h. The reaction mixture was cooled down and diluted with EtOAc, washed with water, brine, dried (MgSO₄), concentrated and purified by ISCO 80 g column (EtOAc/Hex: 0 to 20%) to afford (S)-isopropyl 2-(5-bromo-4-(8-fluorochroman-6-yl)-2,6-dimethylpyridin-3-yl)-2-(tert-butoxy)acetate (0.66 g, 1.298 mmol, 62.9% yield). LCMS (M+H)=508.25 and 510.15.

Example 48

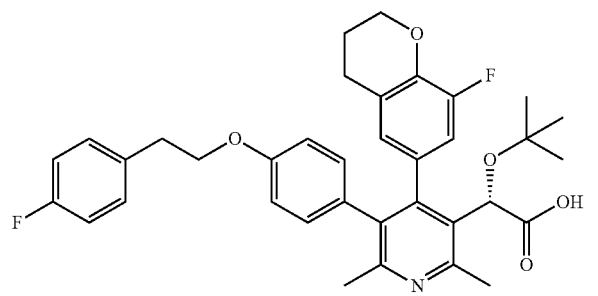 [SMILES: Cc1nc(C)c([C@H](OC(C)(C)C)C(=O)O)c(-c2cc(F)c3c(c2)CCCO3)c1-c1ccc(OCCc2ccc(F)cc2)cc1]

(S)-2-(tert-Butoxy)-2-(4-(8-fluorochroman-6-yl)-5-(4-(4-fluorophenethoxy)phenyl)-2,6-dimethylpyridin-3-yl)acetic Acid A mixture of (S)-isopropyl 2-(5-bromo-4-(8-fluorochroman-6-yl)-2,6-dimethylpyridin-3-yl)-2-(tert-butoxy)acetate (0.06 g, 0.118 mmol), (4-(4-fluorophenethoxy)phenyl)boronic acid (0.031 g, 0.118 mmol), and 2M sodium carbonate (0.15 mL, 0.3 mmol) in 1,4-dioxane (1 ml) was degassed for 10 min. Then, PdCl₂(dppf)-CH₂Cl₂ adduct (0.096 g, 0.118 mmol) was added, degassed for 5 min and the mixture was heated at 80° C. for 5 h. After cooling to room temperature, water was added and the mixture was extracted with ethyl acetate (2×1 ml). The combined organic solution was concentrated to and treated with sodium hydroxide (0.08 g, 2 mmol) and EtOH (1 ml) at 80° C. for 3 h. Then, cooled and purified by prep HPLC to afford (S)-2-(tert-butoxy)-2-(4-(8-fluorochroman-6-yl)-5-(4-(4-fluorophenethoxy)phenyl)-2,6-dimethylpyridin-3-yl)acetic acid (0.0688 g, 96%). LCMS (M+H)=602.1.

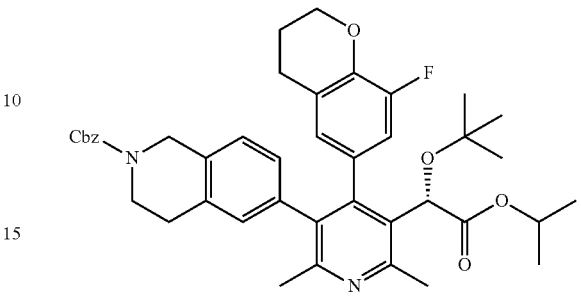

(S)-Benzyl 6-(5-(1-(tert-butoxy)-2-isopropoxy-2-oxoethyl)-4-(8-fluorochroman-6-yl)-2,6-dimethylpyridin-3-yl)-3,4-dihydroisoquinoline-2(1H)-carboxylate A mixture of (S)-isopropyl 2-(5-bromo-4-(8-fluorochroman-6-yl)-2,6-dimethylpyridin-3-yl)-2-(tert-butoxy)acetate (0.6 g, 1.18 mmol), benzyl 6-(6-methyl-4,8-dioxo-1,3,6,2-dioxazaborocan-2-yl)-3,4-dihydroisoquinoline-2(1H)-carboxylate (0.6 g, 1.421 mmol), 2-dicyclohexylphosphino-2',6'-dimethoxybiphenyl (0.097 g, 0.236 mmol) and 2M K₃PO₄ (4.43 ml, 8.86 mmol) in 1,4-dioxane (5 ml) and water (1 ml) was degassed for 10 min. Then, Pd(OAc)₂ (0.026 g, 0.118 mmol) was added, degassed for 5 min and mixture was heated at 80° C. for 3 h. After cooling to room temperature, water was added and the mixture was extracted with ethyl acetate, washed with brine, dried (Na₂SO₄), filtered and concentrated. The residue was then purified by silica gel chromatography (EtOAc/hexane: 0-60%) to afford (S)-benzyl 6-(5-(1-(tert-butoxy)-2-isopropoxy-2-oxoethyl)-4-(8-fluorochroman-6-yl)-2,6-dimethylpyridin-3-yl)-3,4-dihydroisoquinoline-2(1H)-carboxylate (0.45 g, 0.648 mmol, 54.9%) as white foam. LCMS (M+H)=695.5.

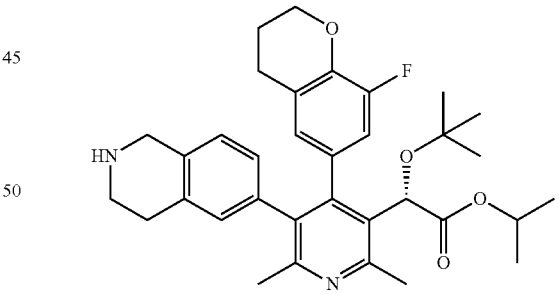

(S)-Isopropyl 2-(tert-butoxy)-2-(4-(8-fluorochroman-6-yl)-2,6-dimethyl-5-(1,2,3,4-tetrahydroisoquinolin-6-yl)pyridin-3-yl)acetate A solution of (S)-benzyl 6-(5-(1-(tert-butoxy)-2-isopropoxy-2-oxoethyl)-4-(8-fluorochroman-6-yl)-2,6-dimethylpyridin-3-yl)-3,4-dihydroisoquinoline-2(1H)-carboxylate (0.45 g, 0.648 mmol) in Ethanol (20 mL) was degassed with N₂. Then, 10% Pd/C (0.069 g, 0.065 mmol) was added, degassed, filled with H₂. 1M HCl (1.4 mL, 1.400 mmol) was injected dropwise. The reaction mixture was stirred under H₂ balloon pressure for 20 h, filtered off the solid and concentrated to dryness to afford (S)-isopropyl 2-(tert-butoxy)-2-(4-(8-fluorochroman-6-yl)-2,6-dimethyl-5-(1,2,3,4-tetrahydroisoquinolin-6-yl)pyridin-3-yl)acetate, 2HCl as a grey solid (0.41 g, 100%). LCMS (M+H)=561.4.

Example 49

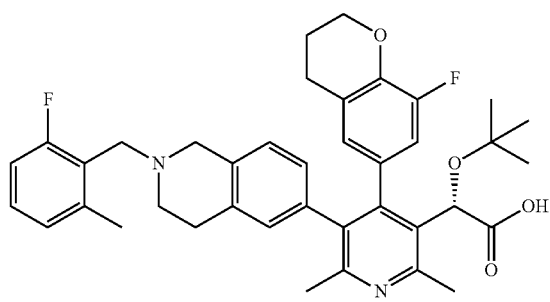 [SMILES: Cc1cccc(Cl)c1CN1CCc2cc(-c3c(C)nc(C)c([C@H](OC(C)(C)C)C(=O)O)c3-c3cc(F)c4c(c3)CCCO4)ccc2C1]

(S)-2-(tert-Butoxy)-2-(5-(2-(2-fluoro-6-methylbenzyl)-1,2,3,4-tetrahydroisoquinolin-6-yl)-4-(8-fluorochroman-6-yl)-2,6-dimethylpyridin-3-yl)acetic Acid A solution of (S)-isopropyl 2-(tert-butoxy)-2-(4-(8-fluorochroman-6-yl)-2,6-dimethyl-5-(1,2,3,4-tetrahydroisoquinolin-6-yl)pyridin-3-yl)acetate, 2 HCl (0.015 g, 0.024 mmol), TEA (0.02 ml, 0.143 mmol) and 2-fluoro-6-methylbenzaldehyde (7 mg, 0.051 mmol) in EtOH (0.5 ml) was stirred at rt for 18 h. Then, sodium triacetoxyborohydride (0.025 g, 0.118 mmol) was added. The mixture was stirred at rt for 2 h and then added sodium hydroxide (0.04 g, 1 mmol). The mixture was heated at 80° C. in a sealed vial for 2 h and cooled down, purified by prep HPLC to afford (S)-2-(tert-butoxy)-2-(5-(2-(2-fluoro-6-methylbenzyl)-1,2,3,4-tetrahydroisoquinolin-6-yl)-4-(8-fluorochroman-6-yl)-2,6-dimethylpyridin-3-yl)acetic acid (0.0118 g, 0.018 mmol, 78% yield). LCMS (M+H)=641.2.

Example 50

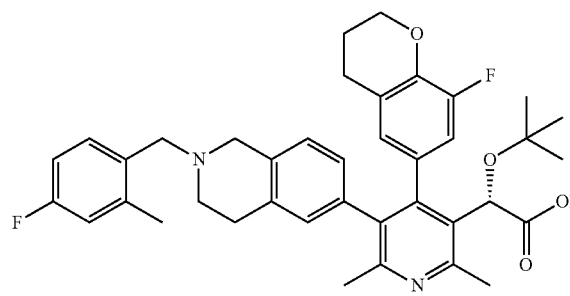

(S)-2-(tert-Butoxy)-2-(5-(2-(4-fluoro-2-methylbenzyl)-1,2,3,4-tetrahydroisoquinolin-6-yl)-4-(8-fluorochroman-6-yl)-2,6-dimethylpyridin-3-yl)acetic Acid A solution of (S)-isopropyl 2-(tert-butoxy)-2-(4-(8-fluorochroman-6-yl)-2,6-dimethyl-5-(1,2,3,4-tetrahydroisoquinolin-6-yl)pyridin-3-yl)acetate, 2 HCl (0.015 g, 0.024 mmol), TEA (0.02 ml, 0.143 mmol) and 4-fluoro-2-methylbenzaldehyde (10 mg, 0.072 mmol) in EtOH (0.5 ml) was stirred at rt for 18 h. Then, sodium triacetoxyborohydride (0.025 g, 0.118 mmol) was added. The mixture was stirred at rt for 2 h and added sodium hydroxide (0.02 g, 0.500 mmol). The mixture was heated at 85° C. in a sealed vial for 2 h and cooled down and purified by prep HPLC to afford (S)-2-(tert-butoxy)-2-(5-(2-(4-fluoro-2-methylbenzyl)-1,2,3,4-tetrahydroisoquinolin-6-yl)-4-(8-fluorochroman-6-yl)-2,6-dimethylpyridin-3-yl)acetic acid (0.0113 g, 0.018 mmol, 74.5% yield). LCMS (M+H)=641.2.

Example 51

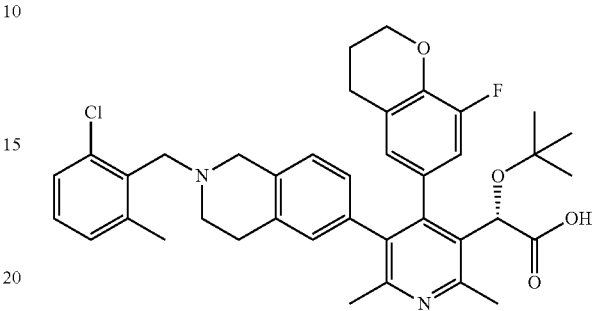

(S)-2-(tert-Butoxy)-2-(5-(2-(2-chloro-6-methylbenzyl)-1,2,3,4-tetrahydroisoquinolin-6-yl)-4-(8-fluorochroman-6-yl)-2,6-dimethylpyridin-3-yl)acetic Acid A mixture of (S)-isopropyl 2-(tert-butoxy)-2-(4-(8-fluorochroman-6-yl)-2,6-dimethyl-5-(1,2,3,4-tetrahydroisoquinolin-6-yl)pyridin-3-yl)acetate, 2 HCl (0.020 g, 0.032 mmol), DIPEA (0.03 ml, 0.172 mmol), 2-chloro-6-methylbenzaldehyde (0.016 g, 0.103 mmol) and MgSO₄ (0.3 g) in EtOH (0.5 mL) was stirred at rt for 18 h. Then, sodium triacetoxyborohydride (0.03 g, 0.142 mmol) was added. The mixture was stirred at rt for 2 h, filtered off the solid. The filtrate was treated with sodium hydroxide (0.05 g, 1.250 mmol) at 85° C. in a sealed vial for 2 h and purified by prep HPLC to afford (S)-2-(tert-butoxy)-2-(5-(2-(2-chloro-6-methylbenzyl)-1,2,3,4-tetrahydroisoquinolin-6-yl)-4-(8-fluorochroman-6-yl)-2,6-dimethylpyridin-3-yl)acetic acid (0.0074 g, 10.92 µmol, 34.6% yield). LCMS (M+H)=657.2.

Example 52

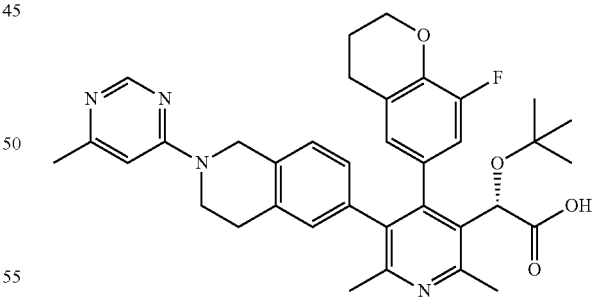

(S)-2-(tert-Butoxy)-2-(4-(8-fluorochroman-6-yl)-2,6-dimethyl-5-(2-(6-methylpyrimidin-4-yl)-1,2,3,4-tetrahydroisoquinolin-6-yl)pyridin-3-yl)acetic Acid A solution of (S)-isopropyl 2-(tert-butoxy)-2-(4-(8-fluorochroman-6-yl)-2,6-dimethyl-5-(1,2,3,4-tetrahydroisoquinolin-6-yl)pyridin-3-yl)acetate, 2 HCl (0.015 g, 0.024 mmol), potassium carbonate (0.03 g, 0.217 mmol) and 4-chloro-6-methylpyrimidine (4.57 mg, 0.036 mmol) in dioxane (0.5 mL) was stirred at 100° C. for 20 h in a sealed vial, and then treated with sodium hydroxide (0.02 g, 0.500 mmol) in EtOH (1 ml) at 85° C. for 2 h. Then, cooled and purified by prep HPLC to afford (S)-2-(tert-butoxy)-2-(4-(8-fluorochroman-6-yl)-2,6-dimethyl-5-(2-(6-methylpyrimidin-4-yl)-1,2,3,4-tetrahydroisoquinolin-6-yl)pyridin-3-yl)acetic acid (0.0082 g, 0.013 mmol, 56.7% yield). LCMS (M+H)=611.2.

Example 53

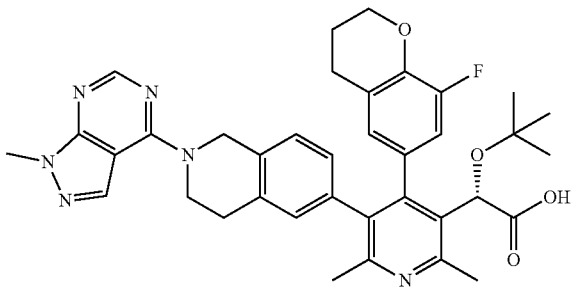 [SMILES: Cc1nc(C)c([C@H](OC(C)(C)C)C(=O)O)c(-c2cc(F)c3c(c2)CCCO3)c1-c1ccc2c(c1)CCN(c1ncnc3c1cnn3C)C2]

(S)-2-(tert-Butoxy)-2-(4-(8-fluorochroman-6-yl)-2,6-dimethyl-5-(2-(1-methyl-1H-pyrazolo[3,4-d]pyrimidin-4-yl)-1,2,3,4-tetrahydroisoquinolin-6-yl)pyridin-3-yl)acetic Acid To a mixture of (S)-isopropyl 2-(tert-butoxy)-2-(4-(8-fluorochroman-6-yl)-2,6-dimethyl-5-(1,2,3,4-tetrahydroisoquinolin-6-yl)pyridin-3-yl)acetate, 2 HCl (0.03 g, 0.047 mmol), and 4-chloro-1-methyl-1H-pyrazolo[3,4-d]pyrimidine (0.02 g, 0.119 mmol) was added acetonitrile (1 mL), and cesium carbonate (0.05 g, 0.153 mmol), and heated at 100° C. for 24 h in a seal vessel, filtered off the solid, (washed the solid with EtOH). The filtrate was concentrated and redissolved in EtOH (0.5 ml). Sodium hydroxide (0.03 g, 0.750 mmol) was added and the mixture was heated at 85° C. for 2 h, cooled down and purified by prep HPLC to afford (S)-2-(tert-butoxy)-2-(4-(8-fluorochroman-6-yl)-2,6-dimethyl-5-(2-(1-methyl-1H-pyrazolo[3,4-d]pyrimidin-4-yl)-1,2,3,4-tetrahydroisoquinolin-6-yl)pyridin-3-yl)acetic acid (0.0099 g, 0.015 mmol, 32.1% yield). LCMS (M+H)=651.2.

Example 54

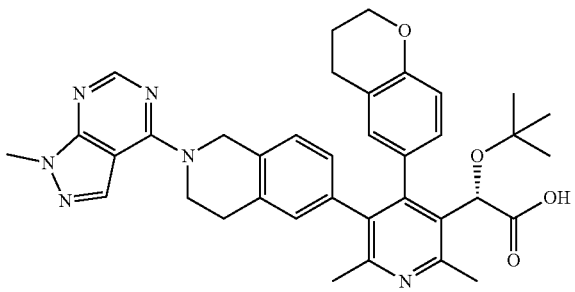 [SMILES: Cc1nc(C)c([C@H](OC(C)(C)C)C(=O)O)c(-c2ccc3c(c2)CCCO3)c1-c1ccc2c(c1)CCN(c1ncnc3c1cnn3C)C2]

(S)-2-(tert-Butoxy)-2-(4-(chroman-6-yl)-2,6-dimethyl-5-(2-(1-methyl-1H-pyrazolo[3,4-d]pyrimidin-4-yl)-1,2,3,4-tetrahydroisoquinolin-6-yl)pyridin-3-yl)acetic Acid To a mixture of (S)-isopropyl 2-(tert-butoxy)-2-(4-(chroman-6-yl)-2,6-dimethyl-5-(1,2,3,4-tetrahydroisoquinolin-6-yl)pyridin-3-yl)acetate, 2 HCl (0.05 g, 0.081 mmol), and 4-chloro-1-methyl-1H-pyrazolo[3,4-d]pyrimidine (0.04 g, 0.237 mmol) was added dioxane (0.5 mL), and potassium carbonate (0.04 g, 0.289 mmol), sealed and heated at 100° C. for 24 h in a seal vessel and filtered off the solid, (washed the solid with EtOH). The filtrate was concentrated and redissolved in EtOH (0.5 ml). Sodium hydroxide (0.03 g, 0.750 mmol) was added and the mixture was heated at 85° C. for 2 h. Then, cooled down and purified by prep HPLC to afford (S)-2-(tert-butoxy)-2-(4-(chroman-6-yl)-2,6-dimethyl-5-(2-(1-methyl-1H-pyrazolo[3,4-d]pyrimidin-4-yl)-1,2,3,4-tetrahydroisoquinolin-6-yl)pyridin-3-yl)acetic acid (0.0049 g, 7.20 μmol, 8.87% yield). LCMS=633.2.

Example 55

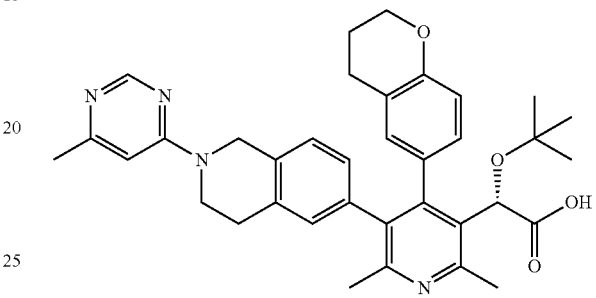

(S)-2-(tert-Butoxy)-2-(4-(chroman-6-yl)-2,6-dimethyl-5-(2-(6-methylpyrimidin-4-yl)-1,2,3,4-tetrahydroisoquinolin-6-yl)pyridin-3-yl)acetic Acid To a solution of (S)-isopropyl 2-(tert-butoxy)-2-(4-(chroman-6-yl)-2,6-dimethyl-5-(1,2,3,4-tetrahydroisoquinolin-6-yl)pyridin-3-yl)acetate, 2 HCl (0.05 g, 0.081 mmol) and 4-chloro-6-methylpyrimidine (0.021 g, 0.162 mmol) and sodium iodide (2 mg, 0.013 mmol) in dioxane (0.5 mL) was added potassium carbonate (0.03 g, 0.217 mmol) and heated at 100° C. in a seal vial for 16 h, filtered off the solid and concentrated. The residue treated with sodium hydroxide (0.015 g, 0.375 mmol) and MeOH (0.5 mL) at 85° C. in sealed vial for 2 h. Then, cooled and purified by prep HPLC to afford (S)-2-(tert-butoxy)-2-(4-(chroman-6-yl)-2,6-dimethyl-5-(2-(6-methylpyrimidin-4-yl)-1,2,3,4-tetrahydroisoquinolin-6-yl)pyridin-3-yl)acetic acid (0.0068 g, 0.011 mmol, 31.0% yield). LCMS (M+H)=593.2.

Example 56

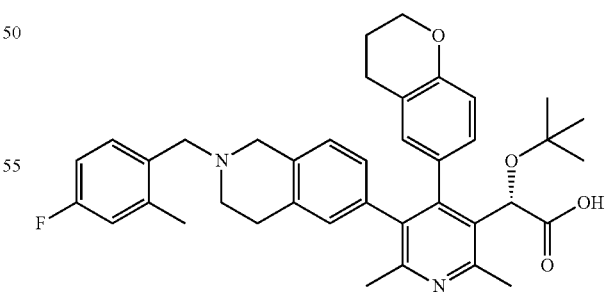

(S)-2-(tert-Butoxy)-2-(4-(chroman-6-yl)-5-(2-(4-fluoro-2-methylbenzyl)-1,2,3,4-tetrahydroisoquinolin-6-yl)-2,6-dimethylpyridin-3-yl)acetic Acid A solution of (S)-isopropyl 2-(tert-butoxy)-2-(4-(chroman-6-yl)-2,6-dimethyl-5-(1,2,3,4-tetrahydroisoquinolin-6- yl)pyridin-3-yl)acetate, 2 HCl (0.015 g, 0.024 mmol), TEA (0.02 ml, 0.143 mmol) and 4-fluoro-2-methylbenzaldehyde (7 mg, 0.051 mmol) in EtOH (0.5 ml) was stirred at rt for 18 h. The, sodium triacetoxyborohydride (0.025 g, 0.118 mmol) was added. The mixture was stirred at rt for 2 h and added sodium hydroxide (0.04 g, 1.000 mmol). The mixture was heated at 85° C. in a sealed vial for 3 h and purified by prep HPLC to afford (S)-2-(tert-butoxy)-2-(4-(chroman-6-yl)-5-(2-(4-fluoro-2-methylbenzyl)-1,2,3,4-tetrahydroisoquinolin-6-yl)-2,6-dimethylpyridin-3-yl)acetic acid (0.0138 g, 0.022 mmol, 91% yield). LCMS (M+H)=623.3.

Example 57

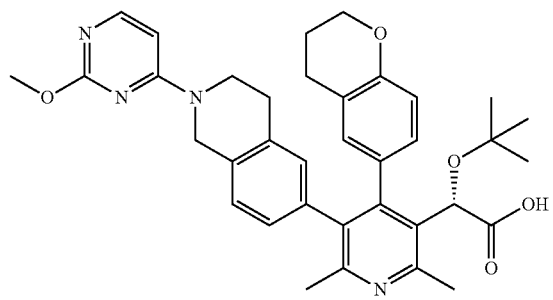 [SMILES: COc1nccc(N2CCc3cc(-c4c(C)nc(C)c([C@H](OC(C)(C)C)C(=O)O)c4-c4ccc5c(c4)CCCO5)ccc3C2)n1]

(S)-2-(tert-Butoxy)-2-(4-(chroman-6-yl)-5-(2-(2-methoxypyrimidin-4-yl)-1,2,3,4-tetrahydroisoquinolin-6-yl)-2,6-dimethylpyridin-3-yl)acetic Acid To a solution of (S)-isopropyl 2-(tert-butoxy)-2-(4-(chroman-6-yl)-2,6-dimethyl-5-(1,2,3,4-tetrahydroisoquinolin-6-yl)pyridin-3-yl)acetate, 2 HCl (0.015 g, 0.024 mmol) and 4-chloro-6-methoxypyrimidine (0.01 g, 0.069 mmol) in ACN (0.5 mL) was added potassium carbonate (0.02 g, 0.145 mmol) and heated at 100° C. for 18 h in a sealed vial. Then, cooled, filtered off the solid, removed the solvent and treated with EtOH (1 ml) and sodium hydroxide (0.975 mg, 0.024 mmol). The resulting mixture was heated at 85° C. for 3 h and purified by prep HPLC to afford (S)-2-(tert-butoxy)-2-(4-(chroman-6-yl)-5-(2-(2-methoxypyrimidin-4-yl)-1,2,3,4-tetrahydroisoquinolin-6-yl)-2,6-dimethylpyridin-3-yl) acetic acid (0.0077 g, 0.013 mmol, 51.4% yield). LCMS (M+H)=609.4.

Example 58

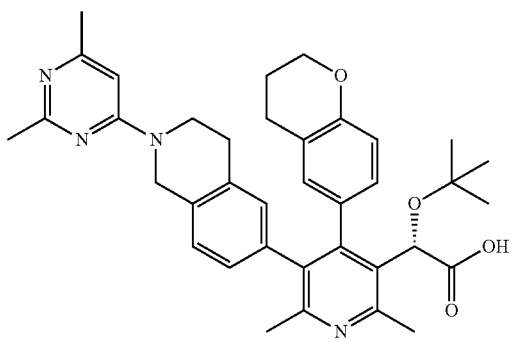 [SMILES: Cc1cc(N2CCc3cc(-c4c(C)nc(C)c([C@H](OC(C)(C)C)C(=O)O)c4-c4ccc5c(c4)CCCO5)ccc3C2)nc(C)n1]

(S)-2-(tert-Butoxy)-2-(4-(chroman-6-yl)-5-(2-(2,6-dimethylpyrimidin-4-yl)-1,2,3,4-tetrahydroisoquinolin-6-yl)-2,6-dimethylpyridin-3-yl)acetic Acid To a solution of (S)-isopropyl 2-(tert-butoxy)-2-(4-(chroman-6-yl)-2,6-dimethyl-5-(1,2,3,4-tetrahydroisoquinolin-6-yl)pyridin-3-yl)acetate, 2 HCl (0.015 g, 0.024 mmol) and 4-chloro-2,6-dimethylpyrimidine (0.01 g, 0.070 mmol) in ACN (0.5 mL) was added potassium carbonate (0.02 g, 0.145 mmol) and heated at 100° C. for 18 h in a sealed vial, filtered off the solid, removed the solvent and the residue was treated with EtOH (1 ml) and sodium hydroxide (0.975 mg, 0.024 mmol). The resulting mixture was heated at 85° C. for 3 h and purified by prep HPLC to afford (S)-2-(tert-butoxy)-2-(4-(chroman-6-yl)-5-(2-(2,6-dimethylpyrimidin-4-yl)-1,2,3,4-tetrahydroisoquinolin-6-yl)-2,6-dimethylpyridin-3-yl)acetic acid (0.0053 g, 8.47 μmol, 34.8% yield). LCMS (M+H)=607.2.

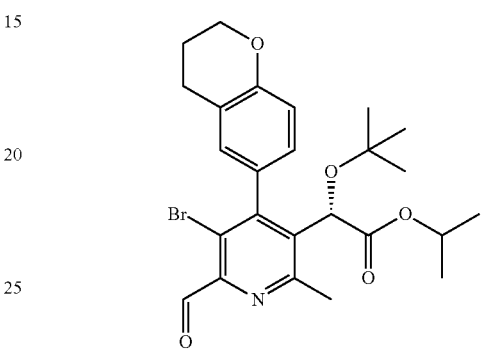

(S)-Isopropyl 2-(5-bromo-4-(chroman-6-yl)-6-formyl-2-methylpyridin-3-yl)-2-(tert-butoxy)acetate To a stirred solution of (S)-isopropyl 2-(5-bromo-4-(chroman-6-yl)-6-(hydroxymethyl)-2-methylpyridin-3-yl)-2-(tert-butoxy)acetate (0.76 g, 1.501 mmol) in $CH_2Cl_2$ (8 mL) was added Dess-Martin Periodinane (0.764 g, 1.801 mmol) one portion at rt. After 16 h, the reaction mixture was diluted with ether (25 mL), washed with 1M NaOH (2×5 ml), brine (5 mL), dried ($Na_2SO_4$), filtered and concentrated to give yellow paste which was purified by silica gel chromatography (EtOAc/hexane:5-30%) to afford (S)-isopropyl 2-(5-bromo-4-(chroman-6-yl)-6-formyl-2-methylpyridin-3-yl)-2-(tert-butoxy)acetate (0.6 g, 1.190 mmol, 79% yield) as paste. LCMS (M+H)=504.10 and 506.00.

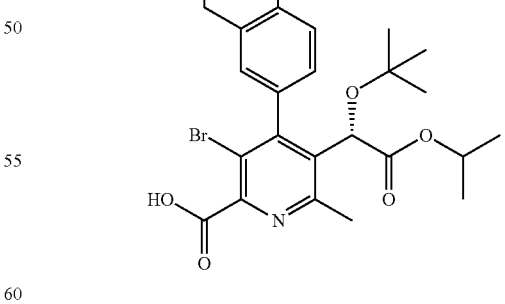

(S)-3-Bromo-5-(1-(tert-butoxy)-2-isopropoxy-2-oxoethyl)-4-(chroman-6-yl)-6-methylpicolinic Acid To a solution of (S)-isopropyl 2-(5-bromo-4-(chroman-6-yl)-6-formyl-2-methylpyridin-3-yl)-2-(tert-butoxy)acetate (0.6 g, 1.190 mmol) in DMSO (10 mL) was added potassium phosphate monobasic (0.8 g, 5.88 mmol) in water (5 mL) followed by sodium chlorite (0.54 g, 5.97 mmol) in water (5 mL) and the mixture was stirred at rt for 30 h. The mixture was then saturated with brine and extracted with ethyl acetate, dried (Na$_2$SO$_4$), filtered and concentrated to afford (S)-3-bromo-5-(1-(tert-butoxy)-2-isopropoxy-2-oxoethyl)-4-(chroman-6-yl)-6-methylpicolinic acid (0.56 g, 1.076 mmol, 90% yield). The crude product was used in next step without purification. LCMS (M+H)=522.3.

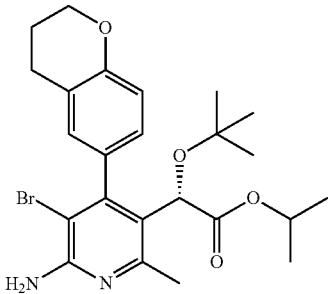 [SMILES: Cc1nc(N)c(Br)c(-c2ccc3c(c2)CCCO3)c1[C@H](OC(C)(C)C)C(=O)OC(C)C]

(S)-Isopropyl 2-(6-amino-5-bromo-4-(chroman-6-yl)-2-methylpyridin-3-yl)-2-(tert-butoxy)acetate To a solution of (S)-3-bromo-5-(1-(tert-butoxy)-2-isopropoxy-2-oxoethyl)-4-(chroman-6-yl)-6-methylpicolinic acid (0.56 g, 1.076 mmol) and TEA (0.300 mL, 2.152 mmol) in toluene (10 mL) was added water (0.097 mL, 5.38 mmol) followed by diphenylphosphoryl azide (0.465 mL, 2.152 mmol) and the resulting mixture was heated at 90° C. for 2 h. The mixture was then cooled to room temperature, diluted with EtOAc and washed with sat. NaHCO$_3$ solution, water and brine. The organic layer was then dried (Na$_2$SO$_4$), filtered and concentrated. The residue was purified by silica gel chromatography (EtOAc/hexane:5-80%) to afford (S)-isopropyl 2-(6-amino-5-bromo-4-(chroman-6-yl)-2-methylpyridin-3-yl)-2-(tert-butoxy)acetate (0.38 g, 0.773 mmol, 71.9% yield) as a solid. $^1$H NMR (500 MHz, CDCl$_3$) δ 7.08-6.85 (m, J=3.3 Hz, 3H), 5.12-4.96 (m, 1H), 4.93 (s, 2H), 4.81 (2s, 1H), 4.28 (m, 2H), 2.96-2.68 (m, 2H), 2.49 (2s, 3H), 2.13-2.04 (m, 2H), 1.29-1.24 (m, 3H), 1.23-1.17 (m, 3H), 0.99 (2s, 9H). LCMS (M+H)=491.20; 493.15.

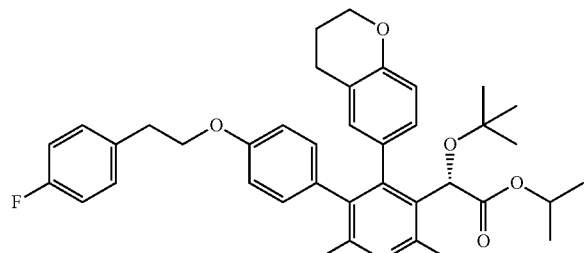

(S)-Isopropyl 2-(6-amino-4-(chroman-6-yl)-5-(4-(4-fluorophenethoxy)phenyl)-2-methylpyridin-3-yl)-2-(tert-butoxy)acetate A mixture of (S)-isopropyl 2-(6-amino-5-bromo-4-(chroman-6-yl)-2-methylpyridin-3-yl)-2-(tert-butoxy)acetate (0.09 g, 0.183 mmol), (4-(4-fluorophenethoxy)phenyl)boronic acid (0.07 g, 0.269 mmol), 2M sodium carbonate (0.4 mL, 0.800 mmol) and 1,4-dioxane (1.5 mL) in a vial was degassed for 10 min. Then, Pd(Ph$_3$P)$_4$ (0.01 g, 8.65 μmol) was added, degassed for 5 min and the mixture was heated at 85° C. for 4 h. The reaction mixture was cooled down and diluted with EtOAc, washed with water, brine, dried (Na$_2$SO$_4$), concentrated to and purified by silica gel chromatography (EtOAc/hexanes: 0 to 50%) to afford (S)-isopropyl 2-(6-amino-4-(chroman-6-yl)-5-(4-(4-fluorophenethoxy)phenyl)-2-methylpyridin-3-yl)-2-(tert-butoxy) acetate (0.08 g, 0.128 mmol, 69.7% yield) as a beige solid. LCMS (M+H)=627.6.

Example 59

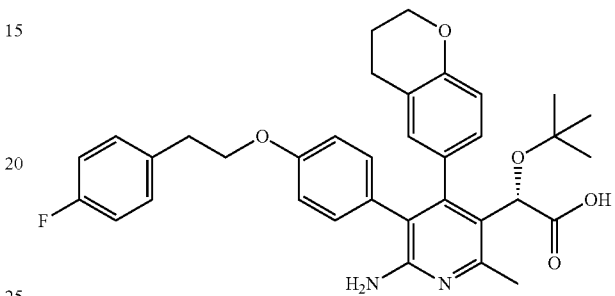

(S)-2-(6-Amino-4-(chroman-6-yl)-5-(4-(4-fluorophenethoxy)phenyl)-2-methylpyridin-3-yl)-2-(tert-butoxy)acetic Acid A mixture of (S)-isopropyl 2-(6-amino-4-(chroman-6-yl)-5-(4-(4-fluorophenethoxy)phenyl)-2-methylpyridin-3-yl)-2-(tert-butoxy)acetate (0.01 g, 0.016 mmol), sodium hydroxide (0.01 g, 0.250 mmol) in MeOH (0.5 mL) was heated at 80° C. in a sealed tube for 3 h, and purified by prep HPLC to afford (S)-2-(6-amino-4-(chroman-6-yl)-5-(4-(4-fluorophenethoxy)phenyl)-2-methylpyridin-3-yl)-2-(tert-butoxy) acetic acid (0.0043 g, 7.13 μmol, 44.7% yield). LCMS (M+H)=585.2.

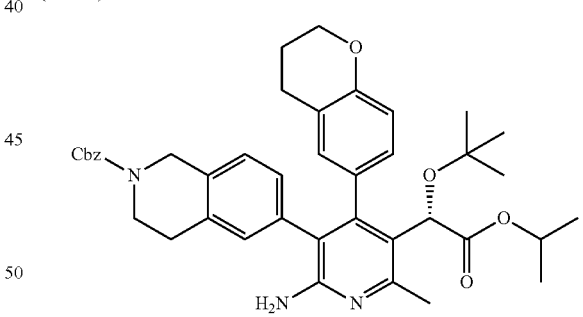

(S)-Benzyl 6-(2-amino-5-(1-(tert-butoxy)-2-isopropoxy-2-oxoethyl)-4-(chroman-6-yl)-6-methylpyridin-3-yl)-3,4-dihydroisoquinoline-2(1H)-carboxylate A mixture of (S)-isopropyl 2-(6-amino-5-bromo-4-(chroman-6-yl)-2-methylpyridin-3-yl)-2-(tert-butoxy)acetate (0.150 g, 0.305 mmol), benzyl 6-(6-methyl-4,8-dioxo-1,3,6,2-dioxazaborocan-2-yl)-3,4-dihydroisoquinoline-2(1H)-carboxylate (0.155 g, 0.366 mmol), 2-dicyclohexylphosphino-2',6'-dimethoxybiphenyl (0.025 g, 0.061 mmol) and 2M K$_3$PO$_4$ (1.2 mL, 2.400 mmol) in 1,4-dioxane (2 mL) and water (0.400 mL) was degassed for 10 min. Then, Pd(OAc)$_2$ (0.07 g, 0.312 mmol) was added, degassed for 5 min and mixture was heated at 80° C. for 4 h. After cooling to room temperature, water was added and the mixture was extracted with ethyl acetate, washed with brine, dried (Na$_2$SO$_4$), filtered and concentrated. The residue was purified by ISCO 24 g column (0-40% EtOAc/hexane) to afford (S)-benzyl 6-(2-amino-5-(1-(tert-butoxy)-2-isopropoxy-2-oxoethyl)-4-(chroman-6-yl)-6-methylpyridin-3-yl)-3,4-dihydroisoquinoline-2(1H)-carboxylate (90 mg, 0.133 mmol, 43.5% yield) as white foam. LCMS (M+H)=678.6.

sodium hydroxide (0.04 g, 1.000 mmol) and the mixture was heated at 85° C. in a sealed vial for 3 h, cooled down and purified by prep HPLC to afford (S)-2-(6-amino-4-(chroman-6-yl)-5-(2-(4-fluoro-2-methylbenzyl)-1,2,3,4-tetrahydroisoquinolin-6-yl)-2-methylpyridin-3-yl)-2-(tert-butoxy) acetic acid (0.0051 g, 8.01 μmol, 32.9% yield). LCMS (M+H)=624.2.

Example 61

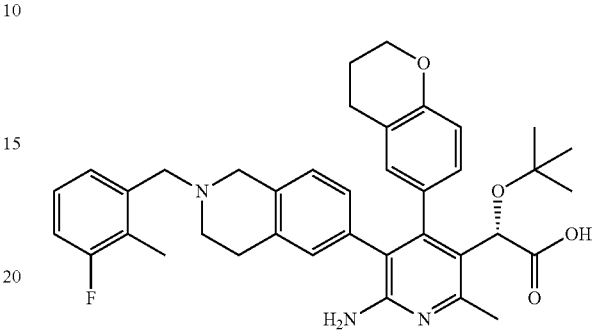

(S)-2-(6-Amino-4-(chroman-6-yl)-5-(2-(3-fluoro-2-methylbenzyl)-1,2,3,4-tetrahydroisoquinolin-6-yl)-2-methylpyridin-3-yl)-2-(tert-butoxy)acetic acid A solution of (S)-isopropyl 2-(6-amino-4-(chroman-6-yl)-2-methyl-5-(1,2,3,4-tetrahydroisoquinolin-6-yl)pyridin-3-yl)-2-(tert-butoxy)acetate, 2 HCl (0.015 g, 0.024 mmol), TEA (0.02 ml, 0.143 mmol) and 3-fluoro-2-methylbenzaldehyde (7 mg, 0.051 mmol) in EtOH (0.5 ml) was stirred at rt for 18 h. NaBH(OAc)$_3$ (0.025 g, 0.118 mmol) was added and the mixture was stirred at rt for 2 h. Then added sodium hydroxide (0.04 g, 1.000 mmol) and the mixture was heated at 80° C. in a sealed vial for 2 h, cooled down and purified by prep HPLC to afford (S)-2-(6-amino-4-(chroman-6-yl)-5-(2-(3-fluoro-2-methylbenzyl)-1,2,3,4-tetrahydroisoquinolin-6-yl)-2-methylpyridin-3-yl)-2-(tert-butoxy)acetic acid (0.0015 g, 2.357 μmol, 9.69% yield). LCMS (M+H)=624.3.

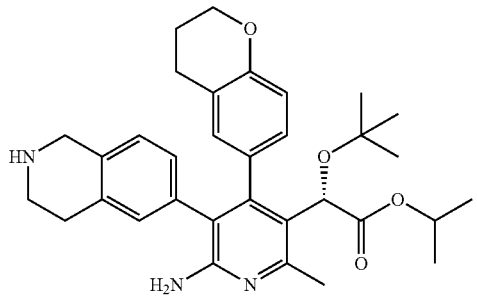 [SMILES: Cc1nc(N)c(-c2ccc3c(c2)CCNC3)c(-c2ccc3c(c2)CCCO3)c1[C@H](OC(C)(C)C)C(=O)OC(C)C]

(S)-Isopropyl 2-(6-amino-4-(chroman-6-yl)-2-methyl-5-(1,2,3,4-tetrahydroisoquinolin-6-yl)pyridin-3-yl)-2-(tert-butoxy)acetate A solution of (S)-benzyl 6-(2-amino-5-(1-(tert-butoxy)-2-isopropoxy-2-oxoethyl)-4-(chroman-6-yl)-6-methylpyridin-3-yl)-3,4-dihydroisoquinoline-2(1H)-carboxylate (0.11 g, 0.162 mmol) in EtOH (15 mL) was purged with N$_2$. 10% Pd/C (0.17 g, 0.16 mmol) and 1M HCl (0.325 mL, 0.325 mmol) was added and degassed and filled with H$_2$. The reaction mixture was stirred under H$_2$ balloon pressure for 4 h, filtered off the solid and the filtrate was concentrated to dryness to afford (S)-isopropyl 2-(6-amino-4-(chroman-6-yl)-2-methyl-5-(1,2,3,4-tetrahydroisoquinolin-6-yl)pyridin-3-yl)-2-(tert-butoxy)acetate (0.088 g, 0.162 mmol, 100% yield). The crude product was used in the next step without purification.

Example 60

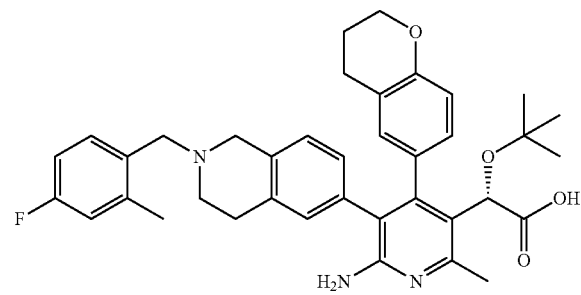 [SMILES: Cc1cc(F)ccc1CN1CCc2cc(-c3c(N)nc(C)c([C@H](OC(C)(C)C)C(=O)O)c3-c3ccc4c(c3)CCCO4)ccc2C1]

(S)-2-(6-Amino-4-(chroman-6-yl)-5-(2-(4-fluoro-2-methylbenzyl)-1,2,3,4-tetrahydroisoquinolin-6-yl)-2-methylpyridin-3-yl)-2-(tert-butoxy)acetic Acid A solution of (S)-isopropyl 2-(6-amino-4-(chroman-6-yl)-2-methyl-5-(1,2,3,4-tetrahydroisoquinolin-6-yl)pyridin-3-yl)-2-(tert-butoxy)acetate, 2 HCl (0.015 g, 0.024 mmol), TEA (0.02 ml, 0.143 mmol) and 4-fluoro-2-methylbenzaldehyde (7 mg, 0.051 mmol) in EtOH (0.5 ml) was stirred at rt for 18 h. Then, sodium triacetoxyborohydride (0.025 g, 0.118 mmol) was added and stirred at rt for 2 h. Then, added Example 62

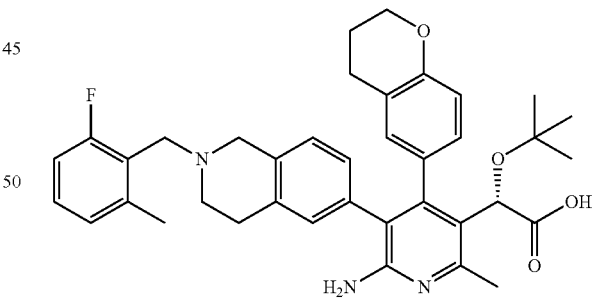

(S)-2-(6-Amino-4-(chroman-6-yl)-5-(2-(2-fluoro-6-methylbenzyl)-1,2,3,4-tetrahydroisoquinolin-6-yl)-2-methylpyridin-3-yl)-2-(tert-butoxy)acetic Acid A solution of (S)-isopropyl 2-(6-amino-4-(chroman-6-yl)-2-methyl-5-(1,2,3,4-tetrahydroisoquinolin-6-yl)pyridin-3-yl)-2-(tert-butoxy)acetate, 2 HCl (0.015 g, 0.024 mmol), TEA (0.02 ml, 0.143 mmol) and 2-fluoro-6-methylbenzaldehyde (7 mg, 0.051 mmol) in EtOH (0.5 ml) was stirred at rt for 18 h. Sodium triacetoxyborohydride (0.025 g, 0.118 mmol) was added and the mixture was stirred at rt for 2 h. Then, added sodium hydroxide (0.04 g, 1.000 mmol) and heated at 80° C. in a sealed vial for 2 h, cooled down and purified by prep HPLC to afford (S)-2-(6-amino-4-(chroman-6-yl)-5-(2-(2-fluoro-6-methylbenzyl)-1,2,3,4-tetrahydroisoquinolin-6-yl)-2-methylpyridin-3-yl)-2-(tert-butoxy) acetic acid (0.0078 g, 0.012 mmol, 48.8% yield). LCMS (M+H)=624.2.

Example 63

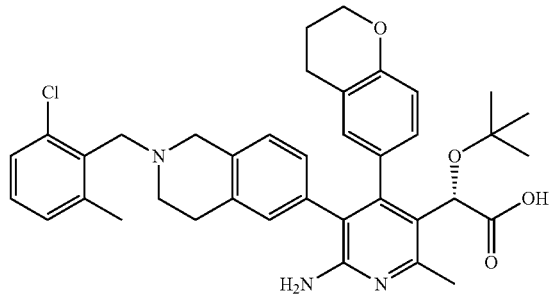 [SMILES: Cc1cccc(Cl)c1CN1CCc2cc(-c3c(N)nc(C)c([C@H](OC(C)(C)C)C(=O)O)c3-c3ccc4c(c3)CCCO4)ccc2C1]

(S)-2-(6-Amino-5-(2-(2-chloro-6-methylbenzyl)-1,2,3,4-tetrahydroisoquinolin-6-yl)-4-(chroman-6-yl)-2-methylpyridin-3-yl)-2-(tert-butoxy)acetic Acid A solution of (S)-isopropyl 2-(6-amino-4-(chroman-6-yl)-2-methyl-5-(1,2,3,4-tetrahydroisoquinolin-6-yl)pyridin-3-yl)-2-(tert-butoxy)acetate, 2 HCl (0.015 g, 0.024 mmol), TEA (0.02 ml, 0.143 mmol) and 2-chloro-6-methylbenzaldehyde (8 mg, 0.052 mmol) in EtOH (0.5 ml) was stirred at rt for 18 h. Sodium triacetoxyborohydride (0.025 g, 0.118 mmol) was added and the mixture was stirred at rt for 2 h. Then, added sodium hydroxide (0.04 g, 1.000 mmol) and heated at 80° C. in a sealed vial for 2 h, cooled down and purified by prep HPLC to afford (S)-2-(6-amino-5-(2-(2-chloro-6-methylbenzyl)-1,2,3,4-tetrahydroisoquinolin-6-yl)-4-(chroman-6-yl)-2-methylpyridin-3-yl)-2-(tert-butoxy) acetic acid (0.0024 g, 3.49 µmol, 14.33% yield) LCMS (M+H)=641.2.

Example 64

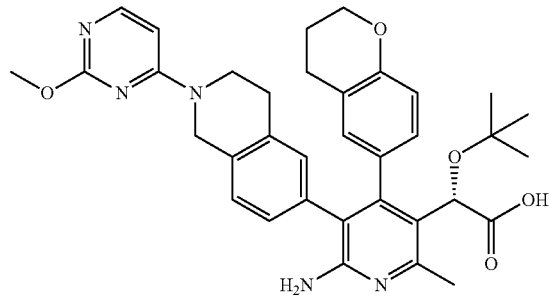 [SMILES: COc1nccc(N2CCc3cc(-c4c(N)nc(C)c([C@H](OC(C)(C)C)C(=O)O)c4-c4ccc5c(c4)CCCO5)ccc3C2)n1]

(S)-2-(6-Amino-4-(chroman-6-yl)-5-(2-(2-methoxypyrimidin-4-yl)-1,2,3,4-tetrahydroisoquinolin-6-yl)-2-methylpyridin-3-yl)-2-(tert-butoxy)acetic Acid To a mixture of (S)-isopropyl 2-(6-amino-4-(chroman-6-yl)-2-methyl-5-(1,2,3,4-tetrahydroisoquinolin-6-yl)pyridin-3-yl)-2-(tert-butoxy)acetate, 2 HCl (0.015 g, 0.024 mmol) and 4-chloro-6-methoxypyrimidine (0.01 g, 0.069 mmol) in ACN (0.5 mL) was added potassium carbonate (0.02 g, 0.145 mmol) and heated at 100° C. for 18 h in a sealed vial. Then filtered off the solid, removed the solvent and the residue was treated with EtOH (1 ml) and sodium hydroxide (10 mg, 0.025 mmol) at 85° C. for 2 h. Then, cooled and purified by prep HPLC to afford (S)-2-(6-amino-4-(chroman-6-yl)-5-(2-(2-methoxypyrimidin-4-yl)-1,2,3,4-tetrahydroisoquinolin-6-yl)-2-methylpyridin-3-yl)-2-(tert-butoxy) acetic acid (0.009 g, 0.014 mmol, 57.6% yield). LCMS (M+H)=610.3.

Example 65

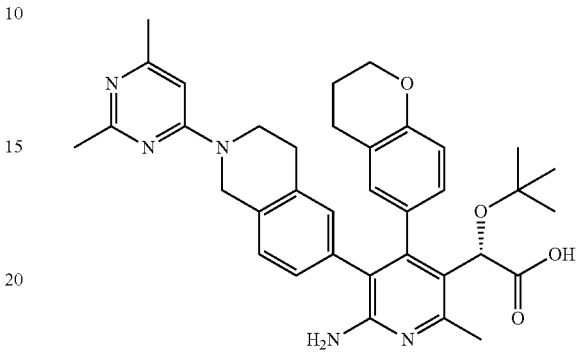

(S)-2-(6-Amino-4-(chroman-6-yl)-5-(2-(2,6-dimethylpyrimidin-4-yl)-1,2,3,4-tetrahydroisoquinolin-6-yl)-2-methylpyridin-3-yl)-2-(tert-butoxy)acetic Acid To a solution of (S)-isopropyl 2-(6-amino-4-(chroman-6-yl)-2-methyl-5-(1,2,3,4-tetrahydroisoquinolin-6-yl)pyridin-3-yl)-2-(tert-butoxy)acetate, 2 HCl (0.015 g, 0.024 mmol) and 4-chloro-2,6-dimethylpyrimidine (0.01 g, 0.070 mmol) in ACN (0.5 mL) was added potassium carbonate (0.02 g, 0.145 mmol) and heated at 100° C. in a seal vial for 18 h. Then, filtered off the solid, removed the solvent and the residue was treated with EtOH (1 ml) and sodium hydroxide (10 mg, 0.025 mmol) at 85° C. for 3 h. Then, cooled and purified by prep HPLC to afford (S)-2-(6-amino-4-(chroman-6-yl)-5-(2-(2,6-dimethylpyrimidin-4-yl)-1,2,3,4-tetrahydroisoquinolin-6-yl)-2-methylpyridin-3-yl)-2-(tert-butoxy)acetic acid (0.0038 g, 6.25 µmol, 25.7% yield). LCMS (M+H)=608.3.

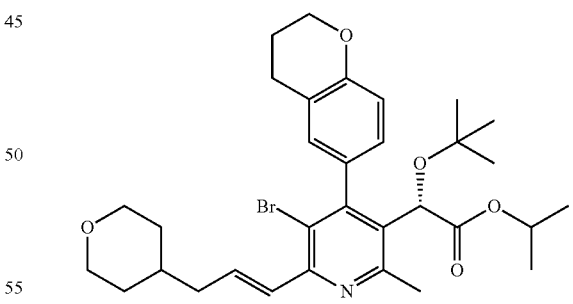

(S,E)-Isopropyl 2-(5-bromo-4-(chroman-6-yl)-2-methyl-6-(3-(tetrahydro-2H-pyran-4-yl)prop-1-en-1-yl)pyridin-3-yl)-2-(tert-butoxy)acetate To solution of (S)-isopropyl 2-(5-bromo-6-(bromomethyl)-4-(chroman-6-yl)-2-methylpyridin-3-yl)-2-(tert-butoxy)acetate (0.1 g, 0.176 mmol) in dioxane (1 mL) was added triphenylphosphine (0.055 g, 0.211 mmol). The mixture was stirred at rt for 20 h. Then sodium hydride (0.014 g, 0.351 mmol) was added and stirred for 3 h at rt. A solution of 2-(tetrahydro-2H-pyran-4-yl)acetaldehyde (0.023 g, 0.176 mmol) in THF (0.5 ml) was injected, and the mixture was stirred at rt for 4 h. The reaction mixture was partitioned between water and EtOAc. The organic solution was washed with brine, dried (MgSO₄), concentrated and purified silica gel chromatography (EtOAc/hexanes: 0 to 50%) to afford (S,E)-isopropyl 2-(5-bromo-4-(chroman-6-yl)-2-methyl-6-(3-(tetrahydro-2H-pyran-4-yl)prop-1-en-1-yl)pyridin-3-yl)-2-(tert-butoxy)acetate (0.11 g, 75%). LCMS (M+H)=602.4.

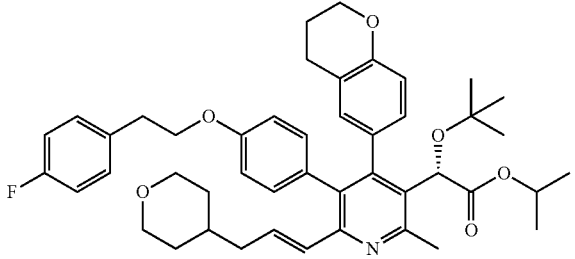 [SMILES: Cc1nc(/C=C/CC2CCOCC2)c(-c2ccc(OCCc3ccc(F)cc3)cc2)c(-c2ccc3c(c2)CCCO3)c1[C@H](OC(C)(C)C)C(=O)OC(C)C]

(S,E)-Isopropyl 2-(tert-butoxy)-2-(4-(chroman-6-yl)-5-(4-(4-fluorophenethoxy)phenyl)-2-methyl-6-(3-(tetrahydro-2H-pyran-4-yl)prop-1-en-1-yl)pyridin-3-yl)acetate A mixture of (S,E)-isopropyl 2-(5-bromo-4-(chroman-6-yl)-2-methyl-6-(3-(tetrahydro-2H-pyran-4-yl)prop-1-en-1-yl)pyridin-3-yl)-2-(tert-butoxy)acetate (0.03 g, 0.050 mmol), (4-(4-fluorophenethoxy)phenyl)boronic acid (0.02 g, 0.077 mmol), 2M sodium carbonate (0.15 mL, 0.300 mmol) in 1,4-dioxane (0.5 ml) was degassed for 5 min. Then, PdCl₂(dppf)-CH₂Cl₂ adduct (4 mg, 4.90 μmol) was added and degassed for 5 min. Then, the mixture was heated at 80° C. for 5 h. After cooling to room temperature, water was added and the mixture was extracted with ethyl acetate (2×1 ml). The combined organic solution was concentrated and purified by prep HPLC to afford (S,E)-isopropyl 2-(tert-butoxy)-2-(4-(chroman-6-yl)-5-(4-(4-fluorophenethoxy)phenyl)-2-methyl-6-(3-(tetrahydro-2H-pyran-4-yl)prop-1-en-1-yl)pyridin-3-yl)acetate (0.01 g, 0.014 mmol, 27.2% yield). LCMS (M+H)=736.20.

Example 66

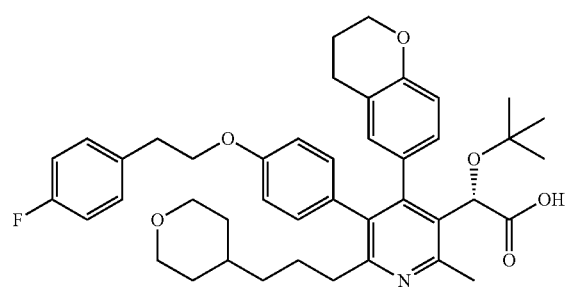 [SMILES: Cc1nc(CCCC2CCOCC2)c(-c2ccc(OCCc3ccc(F)cc3)cc2)c(-c2ccc3c(c2)CCCO3)c1[C@H](OC(C)(C)C)C(=O)O]

(S)-2-(tert-Butoxy)-2-(4-(chroman-6-yl)-5-(4-(4-fluorophenethoxy)phenyl)-2-methyl-6-(3-(tetrahydro-2H-pyran-4-yl)propyl)pyridin-3-yl)acetic Acid A mixture of (S,E)-isopropyl 2-(tert-butoxy)-2-(4-(chroman-6-yl)-5-(4-(4-fluorophenethoxy)phenyl)-2-methyl-6-(3-(tetrahydro-2H-pyran-4-yl)prop-1-en-1-yl)pyridin-3-yl)acetate (0.01 g, 0.014 mmol) and palladium/C (0.005 g, 4.70 μmol) in ethanol (2 mL) was degassed and refilled with H₂. The reaction mixture was stirred under H₂ balloon pressure for 2 h. Filtered off the solid and sodium hydroxide (0.01 g, 0.250 mmol) was added to the filtrate. The mixture was heated at 85° C. for 2 h and purified by prep HPLC to afford (S)-2-(tert-butoxy)-2-(4-(chroman-6-yl)-5-(4-(4-fluorophenethoxy)phenyl)-2-methyl-6-(3-(tetrahydro-2H-pyran-4-yl)propyl)pyridin-3-yl)acetic acid (0.0029 g, 4.17 μmol, 30.7% yield). LCMS (M+H)=696.2.

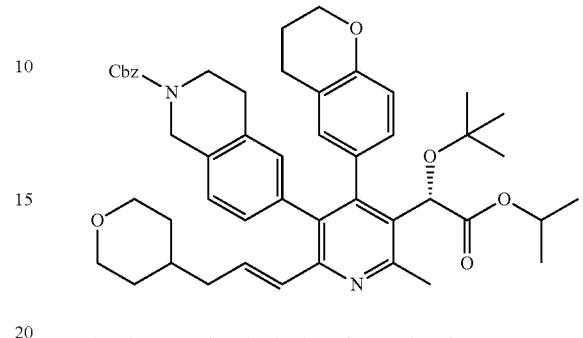

(S,E)-Benzyl 6-(5-(1-(tert-butoxy)-2-isopropoxy-2-oxoethyl)-4-(chroman-6-yl)-6-methyl-2-(3-(tetrahydro-2H-pyran-4-yl)prop-1-en-1-yl)pyridin-3-yl)-3,4-dihydroisoquinoline-2(1H)-carboxylate A mixture of (S,E)-isopropyl 2-(5-bromo-4-(chroman-6-yl)-2-methyl-6-(3-(tetrahydro-2H-pyran-4-yl)prop-1-en-1-yl)pyridin-3-yl)-2-(tert-butoxy)acetate (0.05 g, 0.083 mmol), benzyl 6-(6-methyl-4,8-dioxo-1,3,6,2-dioxazaborocan-2-yl)-3,4-dihydroisoquinoline-2(1H)-carboxylate (0.05 g, 0.118 mmol), 2-dicyclohexylphosphino-2',6'-dimethoxybiphenyl (0.007 g, 0.017 mmol) and 2M potassium phosphate tribasic (0.35 mL, 0.700 mmol) in 1,4-dioxane (1 mL) and water (0.200 mL) was degassed for 10 min. Then, Pd(OAc)₂ (2 mg, 8.33 μmol) was added, degassed for 5 min and mixture was heated at 80° C. for 3 h. After cooling to room temperature, water was added and the mixture was extracted with ethyl acetate, washed with brine, dried (Na₂SO₄), filtered and concentrated. The residue was then purified by silica gel chromatography (5-60% EtOAc/hexane) to afford (S,E)-benzyl 6-(5-(1-(tert-butoxy)-2-isopropoxy-2-oxoethyl)-4-(chroman-6-yl)-6-methyl-2-(3-(tetrahydro-2H-pyran-4-yl)prop-1-en-1-yl)pyridin-3-yl)-3,4-dihydroisoquinoline-2(1H)-carboxylate (0.026 g, 0.033 mmol, 39.7% yield) as white foam. LCMS (M+H)=787.7.

Example 67

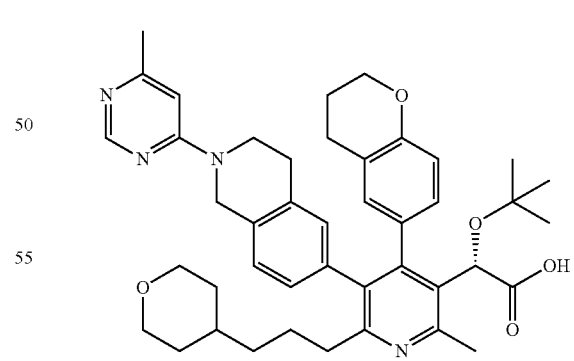

(S)-2-(tert-Butoxy)-2-(4-(chroman-6-yl)-2-methyl-5-(2-(6-methylpyrimidin-4-yl)-1,2,3,4-tetrahydroisoquinolin-6-yl)-6-(3-(tetrahydro-2H-pyran-4-yl)propyl)pyridin-3-yl)acetic Acid To a mixture of (S)-isopropyl 2-(tert-butoxy)-2-(4-(chroman-6-yl)-2-methyl-6-(3-(tetrahydro-2H-pyran-4-yl)propyl)-5-(1,2,3,4-tetrahydroisoquinolin-6-yl)pyridin-3-yl)acetate, 2 HCl (0.01 g, 0.014 mmol) and 4-chloro-6-methylpyrimidine (0.01 g, 0.078 mmol) in dioxane (0.5 mL) was added potassium carbonate (0.02 g, 0.145 mmol) and heated in a seal vial at 100° C. for 18 h. Then, filtered off the solid, removed the solvent, and residue was treated with EtOH (1 ml) and sodium hydroxide (0.550 mg, 0.014 mmol) at 85° C. for 2 h. Then, cooled and purified by prep HPLC to afford (S)-2-(tert-butoxy)-2-(4-(chroman-6-yl)-2-methyl-5-(2-(6-methylpyrimidin-4-yl)-1,2,3,4-tetrahydroisoquinolin-6-yl)-6-(3-(tetrahydro-2H-pyran-4-yl)propyl)pyridin-3-yl)acetic acid (0.0027 g, 3.64 µmol, 26.5% yield) LCMS (M+H)=705.3.

Example 68

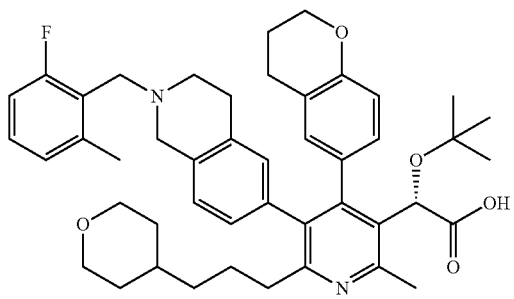 [SMILES: Cc1cccc(F)c1CN1CCc2cc(-c3c(CCCC4CCOCC4)nc(C)c([C@H](OC(C)(C)C)C(=O)O)c3-c3ccc4c(c3)CCCO4)ccc2C1]

(S)-2-(tert-Butoxy)-2-(4-(chroman-6-yl)-5-(2-(2-fluoro-6-methylbenzyl)-1,2,3,4-tetrahydroisoquinolin-6-yl)-2-methyl-6-(3-(tetrahydro-2H-pyran-4-yl)propyl)pyridin-3-yl)acetic Acid A solution of (S)-isopropyl 2-(tert-butoxy)-2-(4-(chroman-6-yl)-2-methyl-6-(3-(tetrahydro-2H-pyran-4-yl)propyl)-5-(1,2,3,4-tetrahydroisoquinolin-6-yl)pyridin-3-yl)acetate (0.01 g, 0.015 mmol), TEA (0.01 ml, 0.072 mmol) and 2-fluoro-6-methylbenzaldehyde (0.01 g, 0.072 mmol) in EtOH (0.5 ml) was stirred at rt for 2 h. Sodium triacetoxyborohydride (0.016 g, 0.075 mmol) was added and the mixture was stirred at rt for 2 h. Then, added sodium hydroxide (0.03 g, 0.750 mmol) and heated at 80° C. in a sealed vial for 4 h and purified by prep HPLC to afford (S)-2-(tert-butoxy)-2-(4-(chroman-6-yl)-5-(2-(2-fluoro-6-methylbenzyl)-1,2,3,4-tetrahydroisoquinolin-6-yl)-2-methyl-6-(3-(tetrahydro-2H-pyran-4-yl)propyl)pyridin-3-yl)acetic acid (0.0088 g, 0.012 mmol, 76% yield). LCMS=735.1.

Biological Methods

Inhibition of HIV Replication:
A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker BD. 71-76. New York: Stockton Press. 1990). Results are shown in Table 1. Activity equal to A refers to a compound having an $EC_{50}<100$ nM, while B and C denote compounds having an $EC_{50}$ between 100 nM and 1 uM (B) or >1 uM (C).

TABLE 1

| Example | Activity | $EC_{50}$ µM |
|---------|----------|--------------|
| 1 | C | 1.743 |
| 2 | A | 0.073 |
| 3 | B | 0.196 |
| 4 | B | |
| 5 | B | |
| 6 | A | |
| 7 | B | 0.545 |
| 8 | B | |
| 9 | A | |
| 10 | A | |
| 11 | A | |
| 12 | A | 0.007 |
| 13 | A | |
| 14 | A | |
| 15 | A | |
| 16 | A | |
| 17 | A | |
| 18 | A | |
| 19 | A | 0.069 |
| 20 | A | |
| 21 | C | 7.766 |
| 22 | B | 0.628 |
| 23 | A | |
| 24 | A | |
| 25 | A | |
| 26 | A | |
| 27 | A | 0.005 |
| 28 | A | |
| 29 | A | |
| 30 | A | |
| 31 | A | |
| 32 | B | |
| 33 | B | 0.282 |
| 34 | A | |
| 35 | A | |
| 36 | A | |
| 37 | A | |
| 38 | A | |
| 39 | A | 0.024 |
| 40 | A | |
| 41 | A | |
| 42 | A | |
| 43 | B | |
| 44 | A | |
| 45 | A | |
| 46 | A | 0.061 |
| 47 | A | |

TABLE 1-continued

| Example | Activity | EC$_{50}$ μM |
|---|---|---|
| 48 | A | |
| 49 | A | |
| 50 | A | |
| 51 | A | |
| 52 | A | |
| 53 | A | |
| 54 | A | 0.008 |
| 55 | A | |
| 56 | A | |
| 57 | A | |
| 58 | A | |
| 59 | A | |
| 60 | A | 0.003 |
| 61 | A | |
| 62 | A | |
| 63 | A | |
| 64 | A | |
| 65 | A | |
| 66 | A | 0.006 |
| 67 | A | |
| 68 | A | |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

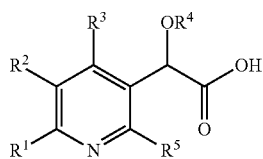

wherein:
$R^1$ is selected from hydrogen, alkyl, hydroxyalkyl, alkoxyalkyl, (alkoxy)alkoxyalkyl, ((alkoxy)alkoxy)alkoxyalkyl, (oxetanyl)alkyl, (tetrahydropyranyl)alkyl, ((oxetanyl)oxy)alkyl, ((tetrahydropyranyl)oxy)alkyl, ((oxetanyl)alkoxy)alkyl, ((tetrahydropyranyl)alkoxy)alkyl, ((R$^7$)(R$^8$)N)alkyl, or (R$^7$)(R$^8$)N;
$R^2$ is phenyl substituted with 0-1 (Ar$^1$)alkoxy substituents and also substituted with 0-3 substituents selected from halo, alkyl, haloalkyl, alkoxy, and haloalkoxy;
$R^3$ is selected from cycloalkyl, cycloalkenyl, phenyl, chromanyl, chromenyl, oxazinyl, or dihydropyranoquinolinyl, and is substituted with 0-3 substituents selected from halo, alkyl, haloalkyl, alkoxy, haloalkoxy, and (Ar$^1$)alkoxy;
$R^4$ is selected from alkyl or haloalkyl;
$R^5$ is alkyl;
$R^6$ is selected from hydrogen, alkyl, (Ar$^1$)alkyl, benzyloxycarbonyl, or Ar$^2$;
$R^7$ is selected from hydrogen, alkyl, alkoxyalkyl, or (tetrahydropyranyl)alkyl;
$R^8$ is selected from hydrogen, alkyl, or alkoxyalkyl;
Ar$^1$ is phenyl substituted with 0-3 substituents selected from halo, alkyl, haloalkyl, alkoxy, and haloalkoxy; and
Ar$^2$ is selected from pyridinyl, pyridazinyl, pyrimidinyl, pyridazinyl, or pyrazolopyrimidinyl, and is substituted with 0-3 substituents selected from halo, alkyl, haloalkyl, alkoxy, and haloalkoxy;
or a pharmaceutically acceptable salt thereof.

2. A compound of Formula I

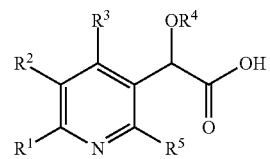

wherein:
$R^1$ is selected from hydrogen, alkyl, hydroxyalkyl, alkoxyalkyl, (alkoxy)alkoxyalkyl, ((alkoxy)alkoxy)alkoxyalkyl, (oxetanyl)alkyl, (tetrahydropyranyl)alkyl, ((oxetanyl)oxy)alkyl, ((tetrahydropyranyl)oxy)alkyl, ((oxetanyl)alkoxy)alkyl, ((tetrahydropyranyl)alkoxy)alkyl, ((R$^7$)(R$^8$)N)alkyl, or (R$^7$)(R$^8$)N;
$R^2$ is tetrahydroisoquinolinyl substituted with 1 R$^6$ substituent and also with 0-3 substituents selected from halo, alkyl, haloalkyl, alkoxy, and haloalkoxy;
$R^3$ is selected from cycloalkyl, cycloalkenyl, phenyl, chromanyl, chromenyl, oxazinyl, or dihydropyranoquinolinyl, and is substituted with 0-3 substituents selected from halo, alkyl, haloalkyl, alkoxy, haloalkoxy, and (Ar$^1$)alkoxy;
$R^4$ is selected from alkyl or haloalkyl;
$R^5$ is alkyl;
$R^6$ is selected from hydrogen, alkyl, (Ar$^1$)alkyl, benzyloxycarbonyl, or Ar$^2$;
$R^7$ is selected from hydrogen, alkyl, alkoxyalkyl, or (tetrahydropyranyl)alkyl;
$R^8$ is selected from hydrogen, alkyl, or alkoxyalkyl;
Ar$^1$ is phenyl substituted with 0-3 substituents selected from halo, alkyl, haloalkyl, alkoxy, and haloalkoxy; and
Ar$^2$ is selected from pyridinyl, pyridazinyl, pyrimidinyl, pyridazinyl, or pyrazolopyrimidinyl, and is substituted with 0-3 substituents selected from halo, alkyl, haloalkyl, alkoxy, and haloalkoxy;
or a pharmaceutically acceptable salt thereof.

3. A compound or salt of claim 1 wherein $R^1$ is alkyl.

4. A compound or salt of claim 1 wherein $R^1$ is selected from hydroxyalkyl, alkoxyalkyl, (alkoxy)alkoxyalkyl, ((alkoxy)alkoxy)alkoxyalkyl, (oxetanyl)alkyl, (tetrahydropyranyl)alkyl, ((oxetanyl)oxy)alkyl, ((tetrahydropyranyl)oxy)alkyl, ((oxetanyl)alkoxy)alkyl, ((tetrahydropyranyl)alkoxy)alkyl, (R$^7$)(R$^8$)N)alkyl, or (R$^7$)(R$^8$)N.

5. A compound or salt of claim 2 wherein $R^2$ is tetrahydroisoquinolinyl substituted with 1 R$^6$ substituent.

6. A compound or salt of claim 1 wherein R$^6$ is (Ar$^1$)alkyl or Ar$^2$.

7. A pharmaceutical composition comprising a compound or salt of claim 1.

8. The composition of claim 7 further comprising at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

9. The composition of claim 8 wherein the other agent is dolutegravir.

10. A method for treating HIV infection comprising administering a compound of claim 1, or a pharmaceutically acceptable salt thereof, to a patient in need thereof.

11. The method of claim 10 further comprising administering at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

12. The method of claim 11 wherein the other agent is dolutegravir.

13. A compound or salt of claim 2 wherein $R^1$ is alkyl.

14. A compound or salt of claim 2 wherein $R^1$ is selected from hydroxyalkyl, alkoxyalkyl, (alkoxy)alkoxyalkyl, ((alkoxy)alkoxy)alkoxyalkyl, (oxetanyl)alkyl, (tetrahydropyranyl)alkyl, ((oxetanyl)oxy)alkyl, ((tetrahydropyranyl)oxy)alkyl, ((oxetanyl)alkoxy)alkyl, ((tetrahydropyranyl)alkoxy)alkyl, $((R^7)(R^8)N)$alkyl, or $(R^7)(R^8)N$.

15. A compound or salt of claim 2 wherein $R^6$ is $(Ar^1)$alkyl or $Ar^2$.

16. A pharmaceutical composition comprising a compound or salt of claim 2.

17. The composition of claim 16 further comprising at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

18. The composition of claim 17 wherein the other agent is dolutegravir.

19. A method for treating HIV infection comprising administering a compound of claim 2, or a pharmaceutically acceptable salt thereof, to a patient in need thereof.

20. The method of claim 19 further comprising administering at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

21. The method of claim 20 wherein the other agent is dolutegravir.

* * * * *